United States Patent
Karmali et al.

(10) Patent No.: US 11,737,979 B2
(45) Date of Patent: Aug. 29, 2023

(54) METHOD OF MAKING LIPID-ENCAPSULATED RNA NANOPARTICLES

(71) Applicant: Arcturus Therapeutics, Inc., San Diego, CA (US)

(72) Inventors: Priya Karmali, San Diego, CA (US); Padmanabh Chivukula, San Diego, CA (US); Joseph E. Payne, San Diego, CA (US); Yanjie Bao, San Diego, CA (US)

(73) Assignee: Arcturus Therapeutics, Inc., San Diego, CA (US)

( * ) Notice: Subject to any disclaimer, the term of this patent is extended or adjusted under 35 U.S.C. 154(b) by 0 days.

(21) Appl. No.: 16/823,212

(22) Filed: Mar. 18, 2020

(65) Prior Publication Data

US 2020/0297634 A1    Sep. 24, 2020

Related U.S. Application Data

(60) Provisional application No. 62/820,496, filed on Mar. 19, 2019.

(51) Int. Cl.
| | |
|---|---|
| *A61K 47/69* | (2017.01) |
| *B82Y 5/00* | (2011.01) |
| *A61K 9/127* | (2006.01) |
| *A61K 9/14* | (2006.01) |
| *A61K 47/60* | (2017.01) |

(52) U.S. Cl.
CPC ............ *A61K 9/1277* (2013.01); *A61K 9/145* (2013.01); *A61K 47/60* (2017.08); *A61K 47/69* (2017.08); *B82Y 5/00* (2013.01)

(58) Field of Classification Search
CPC ...... A61K 9/1277; A61K 47/69; A61K 47/60; A61K 9/145; B82Y 5/00
See application file for complete search history.

(56) References Cited

U.S. PATENT DOCUMENTS

| | | | |
|---|---|---|---|
| 4,895,452 A | 1/1990 | Yiournas et al. | |
| 8,956,572 B2 * | 2/2015 | Knopov | B01J 13/04 |
| | | | 422/130 |
| 9,592,555 B2 * | 3/2017 | Schut | B22F 1/02 |
| 2004/0142025 A1 * | 7/2004 | MacLachlan | A61K 47/10 |
| | | | 424/450 |
| 2012/0021042 A1 | 1/2012 | Panzner et al. | |
| 2013/0037977 A1 * | 2/2013 | Burke | A61K 9/127 |
| | | | 264/4 |
| 2014/0248358 A1 * | 9/2014 | Figueiredo | A61K 31/404 |
| | | | 424/489 |
| 2016/0032320 A1 | 2/2016 | Yaworski | |
| 2016/0243255 A1 * | 8/2016 | Nechev | B01F 3/088 |
| 2017/0152516 A1 | 6/2017 | Knopov | |
| 2017/0196809 A1 | 7/2017 | Bowman et al. | |
| 2018/0170866 A1 * | 6/2018 | Payne | C07C 333/04 |
| 2018/0263918 A1 | 9/2018 | DeRosa et al. | |
| 2019/0029959 A1 | 1/2019 | Costa et al. | |

FOREIGN PATENT DOCUMENTS

| | | | |
|---|---|---|---|
| WO | WO 2001/005373 | 1/2001 | |
| WO | WO-0105373 A1 * | 1/2001 | ........... A61K 9/1278 |
| WO | WO-200105374 A1 | 1/2001 | |
| WO | WO 2010/078045 | 7/2010 | |
| WO | WO-2016081029 A1 | 5/2016 | |
| WO | WO-2018119163 A1 | 6/2018 | |

OTHER PUBLICATIONS

United States Patent and Trademark Office, International Search Report and Written Opinion for PCT/ US20/23442, dated Jun. 11, 2020, 7 pages.

Zhigaltsev et al. "Bottom-Up Design and Synthesis of Limit Size Lipid Nanoparticle Systems with Aqueous and Triglyceride Cores Using Millisecond Microfluidic Mixing" Langmuir, 2012, 28(7), 3633-3640.

* cited by examiner

*Primary Examiner* — Celeste A Roney

(74) *Attorney, Agent, or Firm* — Mintz Levin Cohn Ferris Glovsky and Popeo, P.C.

(57) ABSTRACT

A method of producing a lipid-encapsulated RNA nanoparticle, comprising the steps a) flowing an aqueous solution comprising an RNA through a $1^{st}$ tube having an inner diameter (ID) of between about 0.1" and 0.132"; b) flowing an ethanol solution comprising lipids through a $2^{nd}$ tube having an ID of between about 0.005" and 0.02" at one third the flow rate of the aqueous solution through the $1^{st}$ tube, wherein the lipids comprise a cationic lipid; and c) mixing the ethanol solution with the aqueous solution by flowing the ethanol solution and the aqueous solution into a mixing module consisting of the $2^{nd}$ tube perpendicularly joined to the $1^{st}$ tube; wherein the mixing produces an output solution flowing in the $1^{st}$ tube comprising a turbulent flow of the RNA and the lipids in between about 10% to 75% ethanol v/v, and wherein the lipid-encapsulated RNA nanoparticles have a bilayer structure.

19 Claims, 7 Drawing Sheets

FIG. 2

| Example # | mRNA Length (Number of Nucleotides) | mRNA MW | Lipids Mol % | | | | | mRNA/Lipid (wt/wt) | N/P | Particle Size (nm) | PDI | %Encap | mRNA purity (%) |
|---|---|---|---|---|---|---|---|---|---|---|---|---|---|
| | | | DOTAP | Lipid | DSPC | CHOL | PEG | | | | | | |
| 1 | 4867 | 1582818 | 25 | 25 | 10 | 38.5 | 1.5 | 0.09 | 3 | 99.7 | 0.1 | 97.6 | 75.0 |
| 2 | 4867 | 1582818 | 25 | 25 | 10 | 38.5 | 1.5 | 0.07 | 4 | 87.7 | 0.1 | 99.3 | 79.0 |
| 3 | 4867 | 1582818 | 25 | 25 | 10 | 38.5 | 1.5 | 0.05 | 5 | 85.9 | 0.1 | 99.7 | 80.0 |
| 4 | 4867 | 1582818 | 25 | 25 | 10 | 38.5 | 1.5 | 0.04 | 6 | 81.2 | 0.2 | 99.8 | 76.0 |
| 5 | 4867 | 1582818 | 25 | 25 | 10 | 37 | 3 | 0.06 | 4 | 72.9 | 0.2 | 99.5 | 82.0 |
| 6 | 4867 | 1582818 | 25 | 25 | 10 | 35 | 5 | 0.06 | 4 | 72.0 | 0.1 | 99.5 | 77.0 |
| 7 | 4867 | 1582818 | 25 | 25 | 10 | 38.5 | 1.5 | 0.06 | 4 | 82.4 | 0.1 | 99.2 | 78.0 |
| 8 | 4867 | 1582818 | 25 | 25 | 10 | 38.5 | 1.5 | 0.05 | 5 | 81.8 | 0.1 | 99.4 | 80.0 |
| 9 | 4867 | 1582818 | 20 | 20 | 7 | 51.5 | 1.5 | 0.06 | 4 | 80.3 | 0.1 | 99.5 | 77.0 |
| 10 | 4867 | 1582818 | 20 | 25 | 10 | 42 | 3 | 0.06 | 4 | 84.4 | 0.2 | 97.2 | 74.0 |
| 11 | 4867 | 1582818 | 20 | 30 | 13 | 32 | 5 | 0.06 | 4 | 80.8 | 0.1 | 94.7 | 64.0 |
| 12 | 4867 | 1582818 | 25 | 20 | 10 | 40 | 5 | 0.05 | 4 | 70.2 | 0.1 | 99.7 | 74.0 |
| 13 | 4867 | 1582818 | 25 | 25 | 13 | 35.5 | 1.5 | 0.06 | 4 | 87.7 | 0.1 | 98.8 | 78.0 |
| 14 | 4867 | 1582818 | 25 | 30 | 7 | 35 | 3 | 0.07 | 4 | 81.2 | 0.1 | 95.8 | 72.0 |
| 15 | 4867 | 1582818 | 30 | 20 | 13 | 34 | 3 | 0.06 | 4 | 70.2 | 0.2 | 99.5 | 76.0 |
| 16 | 4867 | 1582818 | 30 | 25 | 7 | 33 | 3 | 0.06 | 4 | 71.7 | 0.2 | 97.9 | 72.0 |
| 17 | 4867 | 1582818 | 30 | 30 | 10 | 25.8 | 1.5 | 0.07 | 4 | 85.9 | 0.1 | 99.2 | 76.0 |
| 18 | 4867 | 1582818 | 20 | 15 | 13 | 49 | 3 | 0.05 | 4 | 68.8 | 0.2 | 98.6 | 76.9 |
| 19 | 4867 | 1582818 | 20 | 20 | 13 | 44 | 3 | 0.05 | 4 | 73.5 | 0.1 | 99.4 | 78.9 |
| 20 | 4867 | 1582818 | 20 | 25 | 13 | 39 | 3 | 0.06 | 4 | 78.6 | 0.1 | 98.9 | 76.2 |
| 21 | 4867 | 1582818 | 25 | 15 | 13 | 44 | 3 | 0.05 | 4 | 67.2 | 0.1 | 98.5 | 73.5 |
| 22 | 4867 | 1582818 | 25 | 20 | 13 | 39 | 3 | 0.06 | 4 | 71.2 | 0.2 | 99.5 | 78.8 |
| 23 | 4867 | 1582818 | 25 | 25 | 13 | 34 | 3 | 0.06 | 4 | 75.2 | 0.1 | 99.3 | 79.1 |
| 24 | 4867 | 1582818 | 30 | 20 | 13 | 34 | 3 | 0.06 | 4 | 72.7 | 0.2 | 99.4 | 78.0 |
| 25 | 4867 | 1582818 | 30 | 30 | 13 | 29 | 3 | 0.07 | 4 | 78.2 | 0.2 | 99.4 | 79.0 |

FIG. 3

| Batch Size (mRNA in g) | mRNA size (# of Nucleotides) | mRNA MW | Lipid Composition | Lipid Mol% | Particle size (nm) | PDI | %Encap | %Yield |
|---|---|---|---|---|---|---|---|---|
| 0.10 | 1331 | 435111 | Lipid:DSPC: Cholesterol: PEG2000-DMG | 50:7:41.5:1.5 | 64.9 | 0.16 | 97.3 | 78% |
| 0.25 | 1331 | 435111 | Lipid:DSPC: Cholesterol: PEG2000-DMG | 50:7:41.5:1.5 | 67.5 | 0.11 | 97.8 | 84% |
| 1.00 | 1331 | 435111 | Lipid:DSPC: Cholesterol: PEG2000-DMG | 50:7:41.5:1.5 | 64 | 0.07 | 95.5 | 88% |
| 3.00 | 1331 | 435111 | Lipid:DSPC: Cholesterol: PEG2000-DMG | 50:7:41.5:1.5 | 64.4 | 0.08 | 97.5 | 82% |
| 10.00 | 1331 | 435111 | Lipid:DSPC: Cholesterol: PEG2000-DMG | 50:7:41.5:1.5 | 63.2 | 0.10 | 96.4 | 88% |

METHOD OF MAKING LIPID-ENCAPSULATED RNA NANOPARTICLES

CROSS-REFERENCE TO RELATED APPLICATIONS

This application claims priority to U.S. Provisional Application No. 62/820,496, filed Mar. 19, 2019, which is incorporated herein by reference in its entirety.

BACKGROUND

Lipids are used as materials for ribonucleic acid (RNA) delivery owing to their ability to form lipid nanoparticles that encapsulate RNA for delivery to target cells upon parenteral administration. (Zimmermann, 2006, Nature, doi: 10.1038/nature04688).

Different methods of producing lipid-encapsulated RNA nanoparticles are known. For example, WO 2001/005373 discloses techniques for preparing lipid-encapsulated RNA nanoparticles using an ethanol injection-type process with a static mixer that provides a turbulent environment, which after vesicle formation are combined with a therapeutic molecule. US 2004/0142025 discloses techniques for forming lipid-encapsulated RNA nanoparticles using non-turbulent mixing and a series of sequential stepwise dilutions. U.S. Pat. No. 6,843,942 discloses a non-turbulent mixing method of forming the particles by spraying lipids in an organic solution pipe through an orifice into nucleic acids in an aqueous solution flowing past the orifice. U.S. Pat. No. 9,005,654 discloses encapsulating siRNA in a lipid nanoparticle (LNP) using turbulent mixing, whereby lipids and RNA as opposing flows enter a T-shaped mixing chamber from opposite arms at about equal rates to produce a 45-60% ethanol solution comprising vesicles, which are collected and then further diluted (direct dilution method). U.S. Pat. No. 9,404,127 discloses that a majority of the LNPs produced by the direct dilution method have non-lamellar morphology, i.e., a non-bilayer structure.

A need exists to improve the process and apparatus for formulating lipid-encapsulated RNA nanoparticles, including the ability to reliably scale up to large amounts of production while optimizing for particle size and homogeneity.

SUMMARY

Disclosed herein is a method of producing a lipid-encapsulated RNA nanoparticle, comprising the steps a) flowing an aqueous solution comprising an RNA through a $1^{st}$ tube having an inner diameter (ID) of between about 0.1" and 0.132"; b) flowing an ethanol solution comprising lipids through a $2^{nd}$ tube having an ID of between about 0.005" and 0.02" at one third the flow rate of the aqueous solution through the $1^{st}$ tube, wherein the lipids comprise a cationic lipid; and c) mixing the ethanol solution with the aqueous solution by flowing the ethanol solution and the aqueous solution into a mixing module consisting of the $2^{nd}$ tube perpendicularly joined to the $1^{st}$ tube; wherein the mixing produces an output solution flowing in the $1^{st}$ tube comprising a turbulent flow of the RNA and the lipids in between about 10% to 75% ethanol v/v, and wherein the lipid-encapsulated RNA nanoparticles have a bilayer structure.

In some embodiments, the output flow rate is at least 200 ml/min. In another embodiment, the combined flow has a Reynolds number of at least 2,000.

In some embodiments, aqueous solution is pumped through the $1^{st}$ tube by a $1^{st}$ HPLC pump, preferably with a back pressure of at least 10 psi, 25 psi, 50 psi, 75 psi, or 100 psi. Preferably, the $1^{st}$ tube has an ID of 0.132", and the aqueous solution is pumped at a flow rate of at least 30 ml/min, 45 ml/min, 60 ml/min, 75 ml/min, 90 ml/min, 105 ml/min, 120 ml/min, 150 ml/min, 225 ml/min, 262.5 ml/min, 300 ml/min, or 450 ml/min.

In some embodiments, the ethanol solution is pumped through the $2^{nd}$ tube by a $2^{nd}$ HPLC pump, preferably with a back pressure of at least 40 psi, 80 psi, 150 psi, 300 psi, or 400 psi. Preferably, the $2^{nd}$ tube has an ID of 0.007", 0.01", or 0.02"; and the ethanol solution is pumped at a flow rate of at least 10 ml/min, 15 ml/min, 20 ml/min, 25 ml/min, 30 ml/min, 35 ml/min, 40 ml/min, 50 ml/min, 60 ml/min, or 75 ml/min, 87.5 ml/min, 100 ml/min, or 150 ml/min.

Preferably, the aqueous and ethanol solutions are maintained at 15-20° C.

In some embodiments, the mixing module consists of the $2^{nd}$ tube mounted perpendicularly on the $1^{st}$ tube, wherein the $1^{st}$ tube has an opening through a wall, wherein the opening is the size of the outside diameter of the $2^{nd}$ tube, and wherein the $2^{nd}$ tube is fitted over the opening to permit continuous movement of the $2^{nd}$ solution in the $2^{nd}$ tube into the $1^{st}$ solution in the $1^{st}$ tube. The mixing module preferably consists of stainless steel tubing.

In some embodiments, the method disclosed herein further comprises pumping a dilution buffer through a $3^{rd}$ tube, and mixing the dilution buffer with the output solution by introducing the dilution buffer to the output solution in the region of a Y-connector to produce a diluted output solution. Preferably, the dilution buffer comprises 15 mM Tris, 50 mM NaCl, 9% sucrose, pH 7.5; 10 mM Tris, 50 mM NaCl, 9% sucrose, pH 7.5; 50 mM phosphate, pH 6.0; 20 mM HEPES, 50 mM NaCl, 9% sucrose, pH 7.4; or 50 mM HEPES, 50 mM NaCl, 9% sucrose, pH 7.4. Preferably, the diluted output solution comprises 6.25% ethanol; 8.25% ethanol; or 12.5% ethanol.

In some embodiments, the Y-connector is at an angle of about 45°. Preferably, the Y-connector consists of polyether ether ketone (PEEK).

In some embodiments, the dilution buffer is pumped through the $3^{rd}$ tube at a flow rate of 400-900 mL/min, and the $3^{rd}$ tube has an ID of 0.25".

In another aspect, disclosed herein are lipid-encapsulated RNA nanoparticles produced by the method disclosed herein.

In another aspect, disclosed is a lipid-encapsulated RNA nanoparticle comprising a RNA, produced by a process comprising the steps of a) flowing an aqueous solution comprising an RNA through a $1^{st}$ tube having an inner diameter (ID) of between about 0.1" and 0.132"; b) flowing an ethanol solution comprising lipids through a $2^{nd}$ tube having an ID of between about 0.005" and 0.02" at one third the flow rate of the aqueous solution through the $1^{st}$ tube, wherein the lipids comprise a cationic lipid; and c) mixing the ethanol solution with the aqueous solution by flowing the ethanol solution and the aqueous solution into a mixing module consisting of the $2^{nd}$ tube perpendicularly joined to the $1^{st}$ tube; wherein the mixing produces an output solution flowing in the $1^{st}$ tube comprising a turbulent flow of the RNA and the lipids in between about 10% to 75% ethanol v/v in a turbulent flow. The lipid-encapsulated RNA nanoparticles produced by the process disclosed herein has a bilayer structure, i.e., a lamellar morphology. Preferably, the lipid-encapsulated RNA nanoparticles have an average particle size less than 70 nm, 80 nm, 90 nm, or 100 nm; a polydispersity index (PDI) less than 0.09, 0.07, or 0.05; and encapsulation is greater than 94%, 96%, or 98% RNA. Preferably, the batch size is 0.05 to at least 30 g RNA, and the variability of average particle size between batches is less than 10%.

In yet another aspect, disclosed herein is an apparatus for producing lipid nanoparticles comprising a RNA, comprising a $1^{st}$ tube having an ID of between about 0.1" and 0.132"; connected at one end to a $1^{st}$ HPLC pump and at the other end to a mixing module, wherein the $1^{st}$ HPLC pump is configured to pump an aqueous solution comprising RNA through the $1^{st}$ tube at a flow rate of at least 150 ml/min; a $1^{st}$ reservoir connected to the $1^{st}$ HPLC pump, wherein the $1^{st}$ reservoir contains the aqueous solution; a $2^{nd}$ tube having an ID of between about 0.005" and 0.02" connected at one end to a $2^{nd}$ HPLC pump and at the other end to the mixing module, wherein the $2^{nd}$ HPLC pump is configured to pump an ethanol solution comprising lipid through the $2^{nd}$ tube at a flow rate greater than 50 ml/min, and wherein the $2^{nd}$ tube is perpendicularly joined to the $1^{st}$ tube at the mixing module; a $2^{nd}$ reservoir connected to the $2^{nd}$ HPLC pump, wherein the $2^{nd}$ reservoir contains the ethanol solution, wherein the apparatus is configured to mix the ethanol solution with the aqueous solution by introducing the ethanol solution into the aqueous solution in a region within the mixing module to produce an output solution; and wherein the flow of the output solution produces turbulence.

In some embodiments, apparatus disclosed herein preferably has the mixing module where the $2^{nd}$ tube extends through a wall of the $1^{st}$ tube and partly into the interior of the $1^{st}$ tube; or the $2^{nd}$ tube extends up to a wall of the $1^{st}$ tube and joins the $1^{st}$ tube.

DESCRIPTION OF THE DRAWINGS

FIG. 2 shows a table of exemplary lipid RNA formulations, including particle size.

FIG. 3 shows a table of exemplary lipid RNA formulations, including particle size and batch size.

The aqueous solution comprising RNA is transported by an HPLC pump through tubing comprising regions of 0.03" ID PEEK tubing, 0.05" ID PEEK connector, 0.0625" silicon tubing, and 0.122" ID silicon tubing, and 0.132" ID stainless steel. The organic solution comprising lipids is transported by an HPLC pump through tubing, e.g., comprising regions of 0.03" ID PEEK tubing, 0.02" ID PEEK connector, 0.01" ID stainless steel. The organic solution is pumped into the aqueous solution at a 90 degree angle in the mixing area. The 0.122" ID silicon tubing transports the mixed lipid-RNA outlet to a 0.25" ID polypropylene tubing which merges at a 45 degree angle with dilution buffer in the dilution area. The tubing which merges at a 45 degree angle with dilution buffer in the dilution area can be diluted in series to include 1, 2, 3 or 4 dilution areas of tubing at a 45 degree angle for the dilution process. After the dilution process, the diluted particles are collected in a stainless steel-jacketed vessel maintained at 15-20° C. The particles are further processed by tangential flow filtration using a peristaltic, diaphragm or centrifugal pump.

Figure 5:
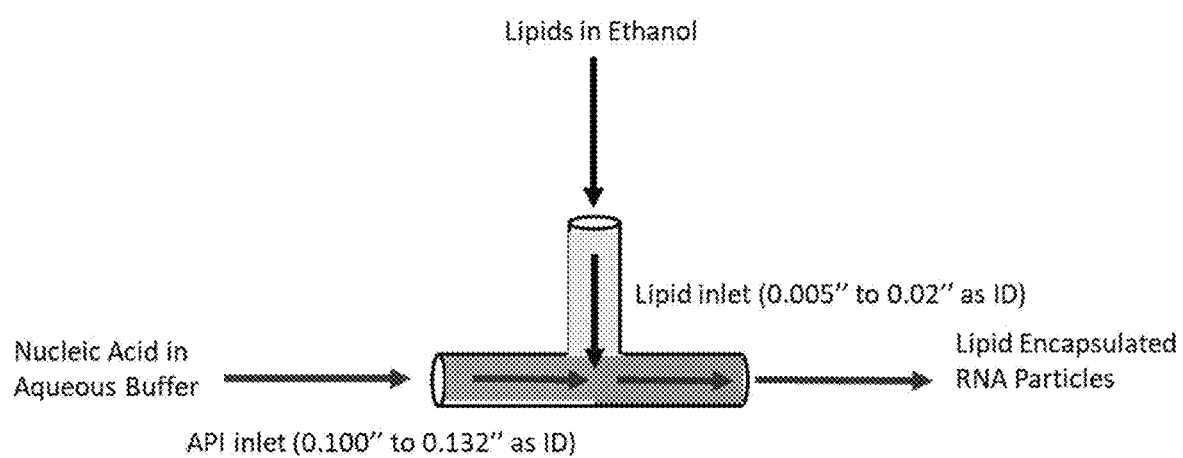

FIG. 5 shows the mixing module in more detail. The nucleic acids in buffer are transported through an input arm of a $1^{st}$ (e.g., 0.100-0.132" ID) stainless steel tube. The lipids in ethanol are transported through a $2^{nd}$ (e.g., 0.005-0.010" ID) stainless steel tube that is perpendicularly attached to the $1^{st}$ tube. A hole in the wall of the first tube allows transport of liquid from the $2^{nd}$ tube to the interior of the $1^{st}$ tube. Lipid-encapsulated RNA nanoparticles resulting from mixing exit through an output arm of the $1^{st}$ tube.

Figure 6A:
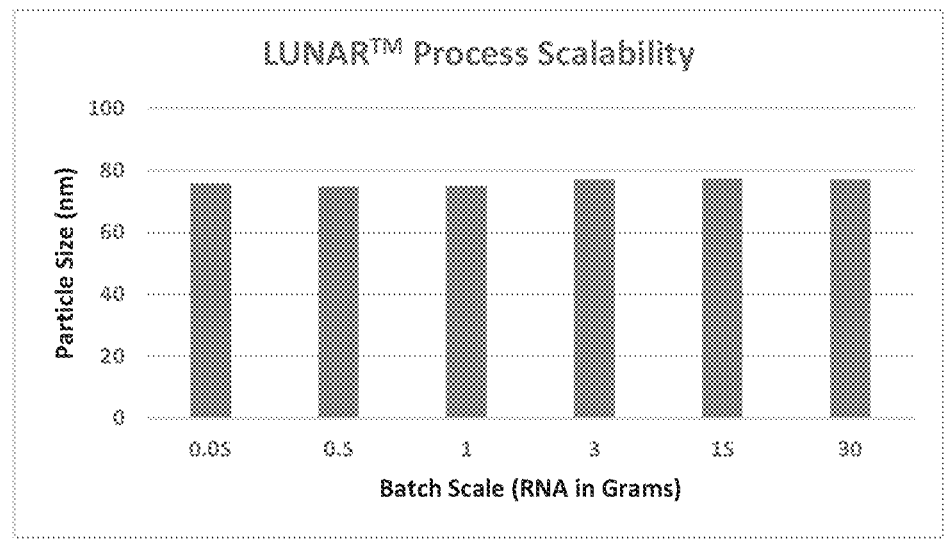

FIG. 6A shows the scalability of the process described in Example 1. Particle size remained at no more than 80 nm for batches of 0.05 g, 0.5 g, 1 g, 3 g, 15 g, and 30 g RNA.

Figure 6B:
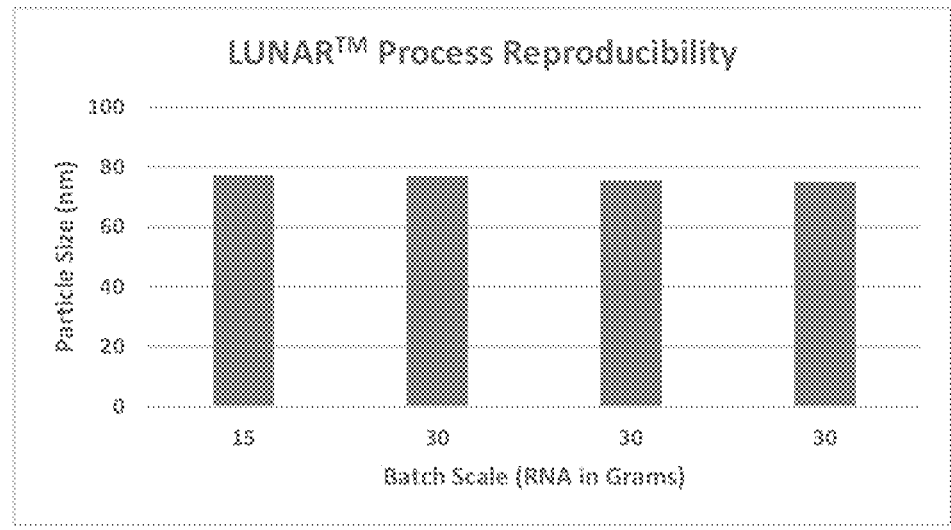

FIG. 6B shows the reproducibility of the lipid nanoparticles produced by the process described in Example 1. Particle size remained less than 80 nm for a 15 g batch and three 30 g batches.

Figure 7:
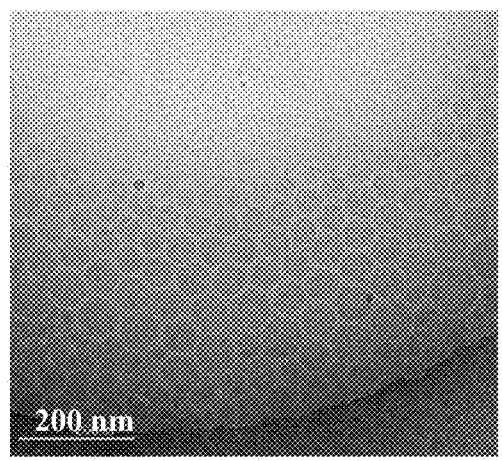
Figure 7:
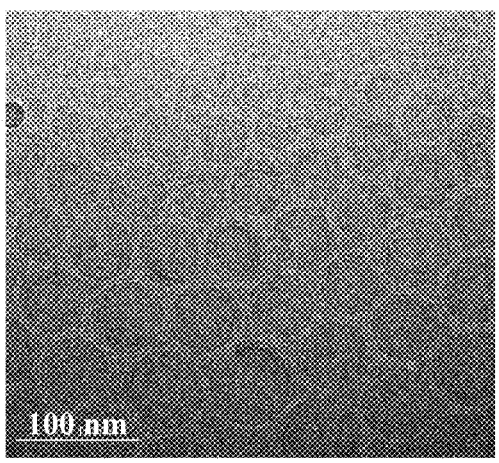

FIG. 7 shows cryo-TEM images of lipid encapsulated RNA nanoparticles. The left image shows RNA loaded nanoparticles, the majority of which are spherical unilamellar structures. Magnification 52000×, scale bar 200 nm. The right image shows high magnification 110,000×, scale bar 100 nm.

DETAILED DESCRIPTION

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, figures and detailed description are to be regarded as illustrative in nature and not as restrictive.

Applicants have discovered a process of mixing lipid and single stranded or double stranded ribonucleic acid (ssRNA or dsRNA) using turbulent flow to produce lipid-encapsulated RNA nanoparticles that provides near monodisperse particles of less than 100 nm having a lamellar morphology, i.e., including a bilayer structure. The process is scalable to more than 30 g RNA. The lipid-encapsulated RNA nanoparticles comprising RNA produced by the processes described herein are useful for delivering RNA in vivo and have improved safety and efficacy upon intravenous administration in animal models.

In one aspect, disclosed herein is a method of producing a lipid-encapsulated RNA nanoparticle, comprising the steps a) flowing an aqueous solution comprising an RNA through a $1^{st}$ tube having an inner diameter (ID) of between about 0.1" and 0.132"; b) flowing an ethanol solution comprising lipids through a $2^{nd}$ tube having an ID of between about 0.005" and 0.02" at one third the flow rate of the aqueous solution through the $1^{st}$ tube, wherein the lipids comprise a cationic lipid; and c) mixing the ethanol solution with the aqueous solution by flowing the ethanol solution and the aqueous solution into a mixing module consisting of the $2^{nd}$ tube perpendicularly joined to the $1^{st}$ tube; wherein the mixing produces an output solution flowing in the $1^{st}$ tube comprising a turbulent flow of the RNA and the lipids in between about 10% to 75% ethanol v/v, and wherein the lipid-encapsulated RNA nanoparticles have a bilayer structure and the lipids comprises a cationic lipid of Formula I:

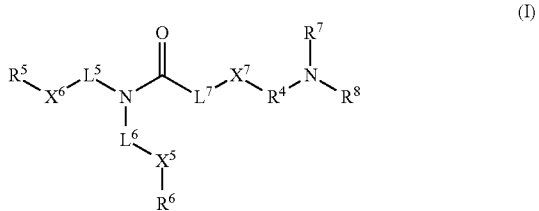

or a pharmaceutically acceptable salt or solvate thereof, wherein $R^5$ and $R^6$ are each independently selected from the group consisting of a linear or branched $C_1$-$C_{31}$ alkyl, $C_2$-$C_{31}$ alkenyl or $C_2$-$C_{31}$ alkynyl and cholesteryl; $L^5$ and $L^6$ are each independently selected from the group consisting of a linear $C_1$-$C_{20}$ alkyl and $C_2$-$C_{20}$ alkenyl; $X^5$ is —C(O)O— or —OC(O)—; $X^6$ is —C(O)O— or —OC(O)—; $X^7$ is S or O; $L^7$ is absent or lower alkyl; $R^4$ is a linear or branched $C_1$-$C_6$ alkyl; and $R^7$ and $R^8$ are each independently selected from the group consisting of a hydrogen and a linear or branched $C_1$-$C_6$ alkyl.

In another aspect, disclosed herein is a lipid-encapsulated RNA nanoparticle produced by the method as presented herein.

In yet another aspect, disclosed herein is a lipid-encapsulated RNA nanoparticle produced by a process, wherein the process comprises the steps of a) flowing an aqueous solution comprising an RNA through a $1^{st}$ tube having an inner diameter (ID) of between about 0.1" and 0.132"; b) flowing an ethanol solution comprising lipids through a $2^{nd}$ tube having an ID of between about 0.005" and 0.02" at one third the flow rate of the aqueous solution through the $1^{st}$ tube, wherein the lipids comprise a cationic lipid; and c) mixing the ethanol solution with the aqueous solution by flowing the ethanol solution and the aqueous solution into a mixing module consisting of the $2^{nd}$ tube perpendicularly joined to the $1^{st}$ tube; wherein the mixing produces an output solution flowing in the $1^{st}$ tube comprising a turbulent flow of the RNA and the lipids in between about 10% to 75% ethanol v/v, and wherein the lipid-encapsulated RNA nanoparticles have a bilayer structure, and wherein the lipid-encapsulated RNA nanoparticles have a bilayer structure and the lipid comprises a cationic lipid of Formula I.

In some embodiments, the output solution flowing in the $1^{st}$ tube comprises a turbulent flow of the RNA and the lipids in about 10% to about 50% ethanol v/v.

In some embodiments, the output solution flowing in the $1^{st}$ tube comprises a turbulent flow of the RNA and the lipids in about 16% to about 50% ethanol v/v.

In some embodiments, the output solution flowing in the $1^{st}$ tube comprises a turbulent flow of the RNA and the lipids in about 10%, 15%, 20%, 25%, 30%, 35%, 40%, 44%, 50%, 55%, 60%, 70% or 75% ethanol v/v.

In some embodiments, the output has a flow rate of at least 200 ml/min.

In some embodiments, the flow rate of the output has a Reynolds number of at least 2,000.

In some embodiments, the aqueous solution is pumped through the $1^{st}$ tube by a 1st HPLC pump.

In some embodiments, the aqueous solution is pumped with a back pressure of at least 10 psi, 25 psi, 50 psi, 75 psi, or 100 psi.

In some embodiments, the $1^{st}$ tube has an ID of 0.132".

In some embodiments, the aqueous solution is pumped at a flow rate of at least 30 ml/min, 45 ml/min, 60 ml/min, 75 ml/min, 90 ml/min, 105 ml/min, 120 ml/min, 150 ml/min, 225 ml/min, 262.5 ml/min, 300 ml/min, or 450 ml/min.

In some embodiments, the aqueous solution comprising the RNA comprises between about 2 mM and 50 mM citrate buffer, at a pH of between about 3.0 and 4.5.

In some embodiments, the aqueous solution comprising the RNA further comprises between about 10 mM and 200 mM NaCl.

In some embodiments, the ethanol solution is pumped through the $2^{nd}$ tube by a $2^{nd}$ HPLC pump.

In some embodiments, the ethanol solution is pumped with a back pressure of at least 40 psi, 80 psi, 150 psi, 300 psi, or 400 psi.

In some embodiments, the $2^{nd}$ tube has an ID of 0.007", 0.01", or 0.02".

In some embodiments, the ethanol solution is pumped at a flow rate of at least 10 ml/min, 15 ml/min, 20 ml/min, 25 ml/min, 30 ml/min, 35 ml/min, 40 ml/min, 50 ml/min, 60 ml/min, or 75 ml/min, 87.5 ml/min, 100 ml/min, or 150 ml/min.

In some embodiments, the $1^{st}$ and $2^{nd}$ mixtures are maintained at 15-20° C.

In some embodiments, the mixing module consists of the $2^{nd}$ tube mounted perpendicularly on the $1^{st}$ tube, wherein the $1^{st}$ tube has an opening through a wall, wherein the opening is about the size of the outside diameter of the $2^{nd}$ tube, and wherein the $2^{nd}$ tube is fitted over the opening to permit continuous movement of the $2^{nd}$ solution in the $2^{nd}$ tube into the $1^{st}$ solution in the $1^{st}$ tube.

In some embodiments, the mixing module consists of stainless steel tubing.

In some embodiments, the method further comprises pumping a dilution buffer through a $3^{rd}$ tube, and mixing the dilution buffer with the output solution by introducing the dilution buffer to the output solution in the region of a Y-connector to produce a diluted output solution.

In some embodiments, the method further comprises pumping a $1^{st}$ dilution buffer through a $3^{rd}$ tube and mixing the $1^{st}$ dilution buffer with the output solution by introducing the $1^{st}$ dilution buffer to the output solution in the region of a $1^{st}$ Y-connector to produce a $1^{st}$ diluted output solution.

In some embodiments, the $1^{st}$ dilution buffer comprises between about 10 mM and 20 mM Tris buffer, between about 45 mM and 55 mM NaCl, and between about 8% and 10% sucrose, at a pH between about 7.4 and 8.5.

In some embodiments, the $1^{st}$ dilution buffer comprises between about 10 mM and 20 mM Tris buffer, between about 45 mM and 55 mM NaCl, and between about 8% and 10% sucrose, at a pH between about 7.4 and 8.5 and the RNA is siRNA.

In some embodiments, the method further comprises pumping a $2^{nd}$ dilution buffer through a $4^t$ tube, and mixing the $2^{nd}$ dilution buffer with the $1^{st}$ diluted output solution by introducing the $2^{nd}$ dilution buffer to the $1^{st}$ diluted output solution in the region of a $2^{nd}$ Y-connector to produce a $2^{nd}$ diluted output solution.

In some embodiments, the $1^{st}$ dilution buffer comprises between about 40 mM and 90 mM phosphate buffer, at a pH between about 6.0 and 6.5; and the $2^{nd}$ dilution buffer comprises between about 20 mM and 50 mM HEPES buffer, between about 50 mM and 300 mM NaCl, between about 0% and 15% sucrose, at a pH between about 7.4 and 8.5.

In some embodiments, the $2^{nd}$ dilution buffer comprises between about 20 mM and 50 mM HEPES buffer, between about 50 mM and 300 mM NaCl, between about 0% and 15% sucrose, at a pH between about 7.4 and 8.5.

In some embodiments, the $2^{nd}$ dilution buffer further comprises between about 25 mM and 100 mM NaCl.

In some embodiments, the $1^{st}$ dilution buffer comprises between about 40 mM and 90 mM phosphate buffer, at a pH between about 6.0 and 6.5 and the RNA is mRNA.

In some embodiments, the $1^{st}$ dilution buffer comprises between about 40 mM and 90 mM phosphate buffer, at a pH between about 6.0 and 6.5; and the $2^{nd}$ dilution buffer comprises between about 20 mM and 50 mM HEPES buffer, between about 50 mM and 300 mM NaCl, between about 0% and 15% sucrose, at a pH between about 7.4 and 8.5 and the RNA is mRNA.

In some embodiments, a dilution buffer comprises between about 5 and 25 mM Tris, between 15 and 75 mM NaCl, between about 3 and 12% sucrose at a pH between about 7.0 and 8.5; between about 5 and 20 mM Tris, between about 20 and 70 mM NaCl, between about 3 and 12% sucrose at a pH between about 7.0 and 8.5; between about 20 and 65 mM phosphate at a pH between about 5.5 and 8.0; between about 10 and 30 mM HEPES, between about 25 and 75 mM NaCl, between about 5 and 12% sucrose at a pH between about 7.0 and 8.5; or between about 25 and 65 mM HEPES, between about 25 and 65 mM NaCl, between about 3 and 12% sucrose at a pH between about 7.0 and 8.5. In some embodiments, the dilution buffer comprises 15 mM Tris, 50 mM NaCl, 9% sucrose, pH 7.5; 10 mM Tris, 50 mM NaCl, 9% sucrose at a pH 7.5; 45 mM phosphate, pH 6.0; 20 mM HEPES, 50 mM NaCl, 9% sucrose at a pH between about 7.4 and 8.0; or 50 mM HEPES, 50 mM NaCl, 9% sucrose at a pH between about 7.4 and 8.0. In some embodiments, the dilution buffer comprises 15 mM Tris, 50 mM NaCl, 9% sucrose, pH 7.5; 10 mM Tris, 50 mM NaCl, 9% sucrose at a pH of 7.5; 45 mM phosphate, pH 6.0; 20 mM HEPES, 50 mM NaCl, 9% sucrose at a pH of 7.4 to 8.0; or 50 mM HEPES, 50 mM NaCl, 9% sucrose at a pH of 7.4 to 8.0.

In some embodiments, the diluted output solution comprises 6.25% ethanol; 8.25% ethanol; 8.3% ethanol; or 12.5% ethanol.

In some embodiments, the Y-connector is joined at an angle of about 45°.

In some embodiments, the Y-connector consists of polyether ether ketone.

In some embodiments, the dilution buffer is pumped through the $3^{rd}$ tube at a flow rate of 400-900 mL/min.

In some embodiments, the $3^{rd}$ tube has an ID of 0.25".

In some embodiments, the RNA encapsulated by the lipid nanoparticle is at least 70%, 75%, 80%, or 85% of the RNA mixed with the lipid.

In some embodiments, lipid in the lipid-encapsulated RNA nanoparticle is at least 70%, 75%, 80%, or 85% of the lipid mixed with the RNA.

In some embodiments, $X^7$ is S.

In some embodiments, $R^7$ and $R^8$ are each independently selected from the group consisting of methyl, ethyl and isopropyl.

In some embodiments, $L^5$ and $L^6$ are each independently a $C_1$-$C_{10}$ alkyl. In some embodiments, $L^5$ is $C_1$-$C_3$ alkyl, and $L^6$ is $C_1$-$C_5$ alkyl. In some embodiments, $L^6$ is $C_1$-$C_2$ alkyl. In some embodiments, $L^5$ and $L^6$ are each a linear $C_7$ alkyl. In some embodiments, $L^5$ and $L^6$ are each a linear $C_9$ alkyl.

In some embodiments, $R^5$ and $R^6$ are each independently an alkenyl. In some embodiments, $R^6$ is alkenyl. In some embodiments, $R^6$ is $C_2$-$C_9$ alkenyl. In some embodiments, the alkenyl of $R^5$ and $R^6$ each independently comprise a single double bond. In some embodiments, $R^5$ and $R^6$ are each alkyl. In some embodiments, $R^5$ is a branched alkane. In some embodiments, $R^5$ and $R^6$ are each independently selected from the group consisting of a $C_9$ alkyl, $C_9$ alkenyl and $C_9$ alkynyl. In some embodiments, $R^5$ and $R^6$ are each independently selected from the group consisting of a $C_{11}$ alkyl, $C_{11}$ alkenyl, and $C_{11}$ alkynyl. In some embodiments, $R^5$ and $R^6$ are each independently selected from the group consisting of a $C_7$ alkyl, $C_7$ alkenyl, and $C_7$ alkynyl. In some embodiments, $R^5$ is $-CH((CH_2)_pCH_3)_2$ or $-CH((CH_2)_pCH_3)((CH_2)_{p-1}CH_3)$, wherein p is 4-8. In some embodiments, p is 5 and $L^5$ is a $C_1$-$C_3$ alkyl. In some embodiments, p is 6 and $L^5$ is a $C_3$ alkyl.

In some embodiments, p is 7. In some embodiments, p is 8 and $L^5$ is a $C_1$-$C_3$ alkyl. In some embodiments, $R^5$ consists of $-CH((CH_2)_pCH_3)((CH_2)_{p-1}CH_3)$, wherein p is 7 or 8.

In some embodiments, $R^4$ is ethylene or propylene. In some embodiments, $R^4$ is n-propylene or isobutylene.

In some embodiments, $L^7$ is absent, $R^4$ is ethylene, $X^7$ is S and $R^7$ and $R^8$ are each methyl. In some embodiments, $L^7$ is absent, $R^4$ is n-propylene, $X^7$ is S and $R^7$ and $R^8$ are each methyl. In some embodiments, $L^7$ is absent, $R^4$ is ethylene, $X^7$ is S and $R^7$ and $R^8$ are each ethyl.

In some embodiments, the cationic lipid is selected from the group consisting of

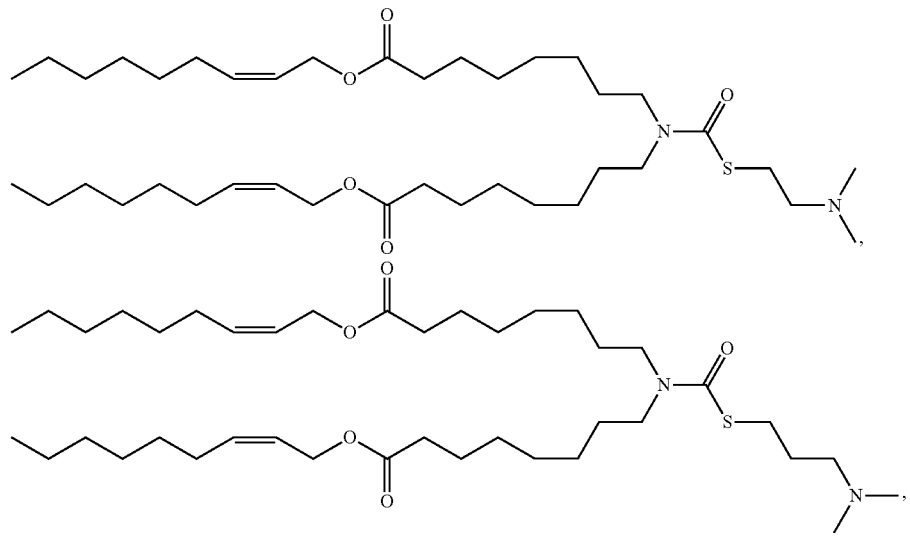

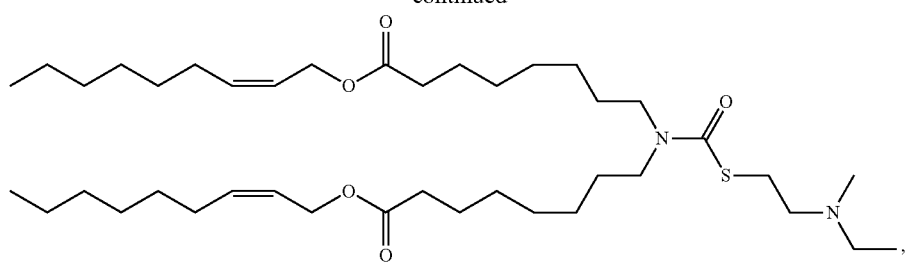
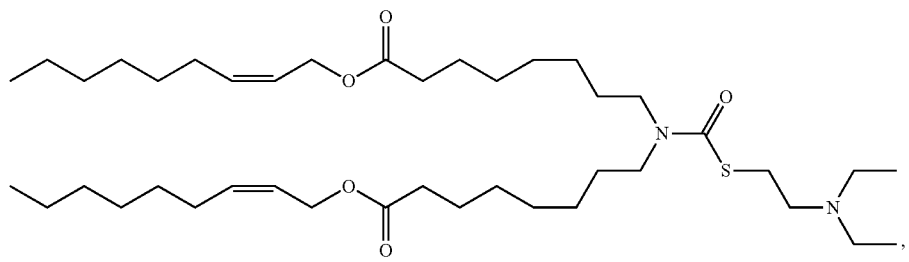
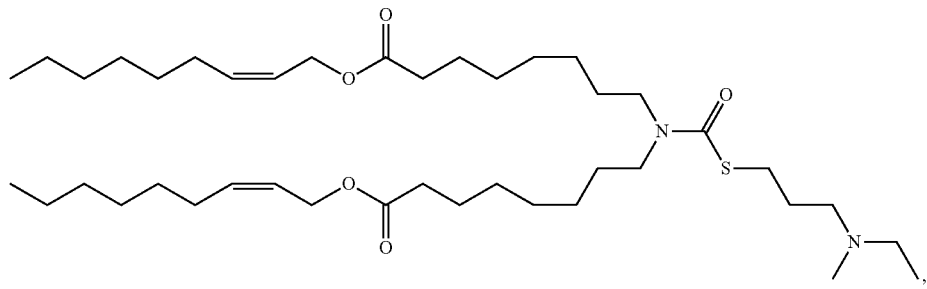
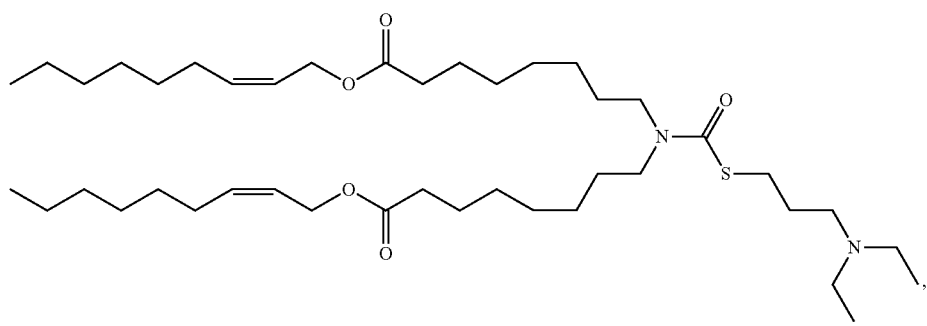
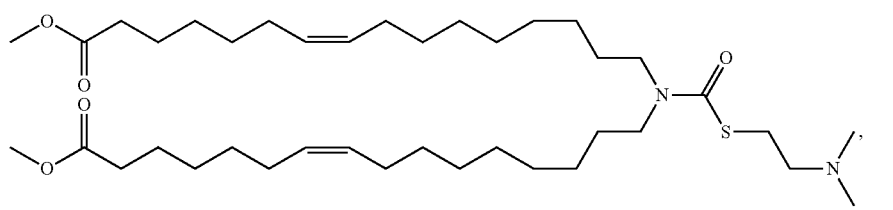
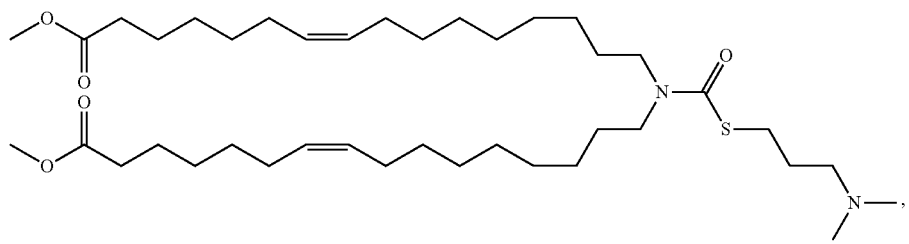

-continued
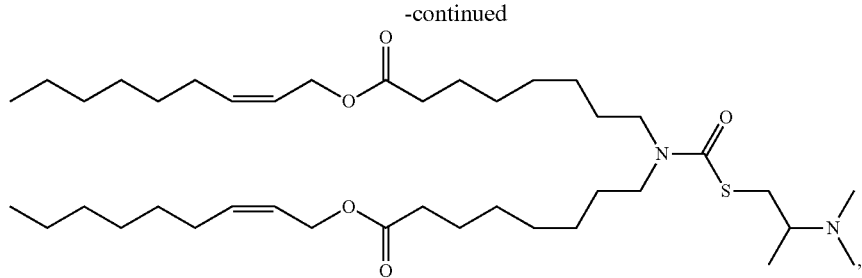
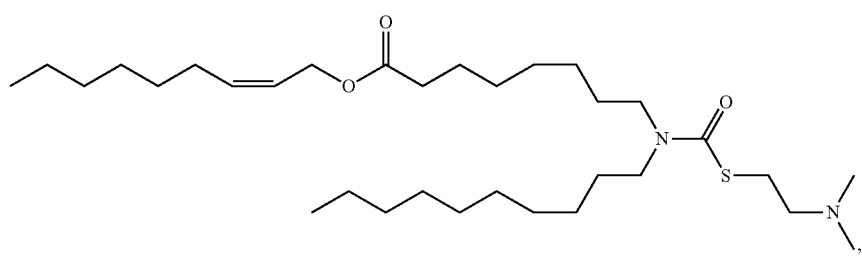
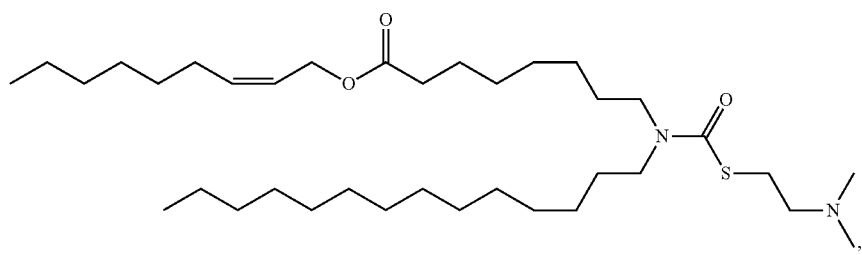
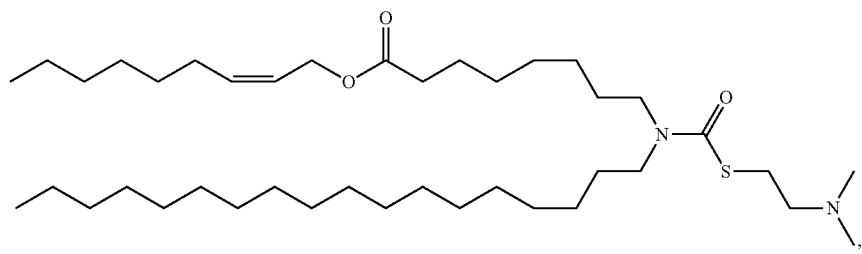
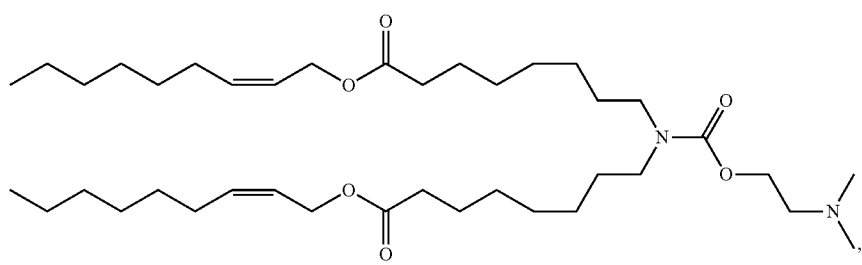

-continued
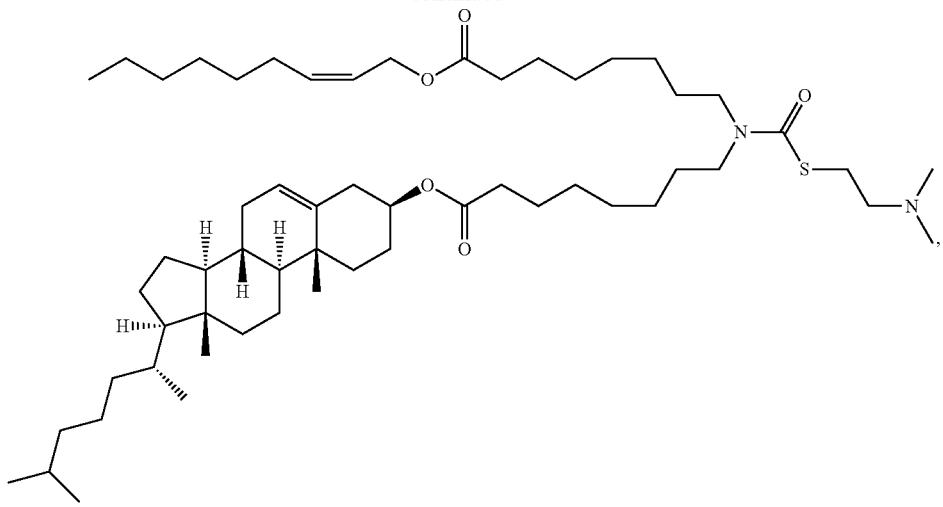
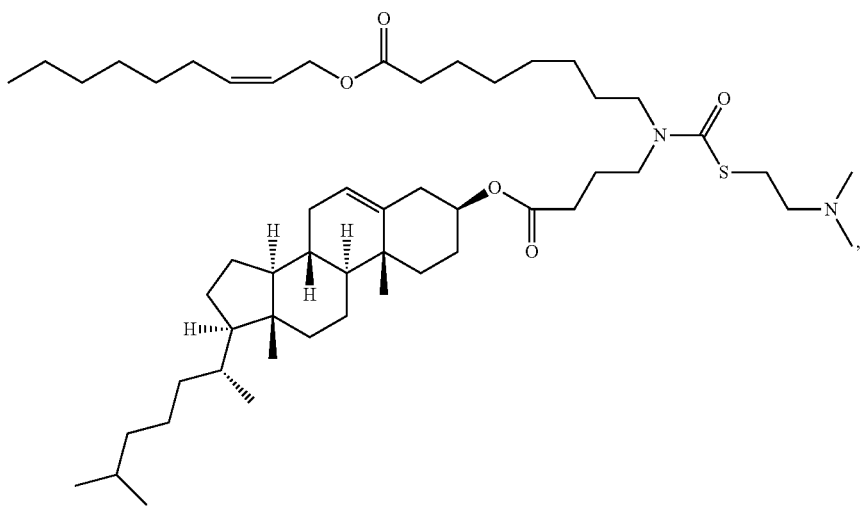
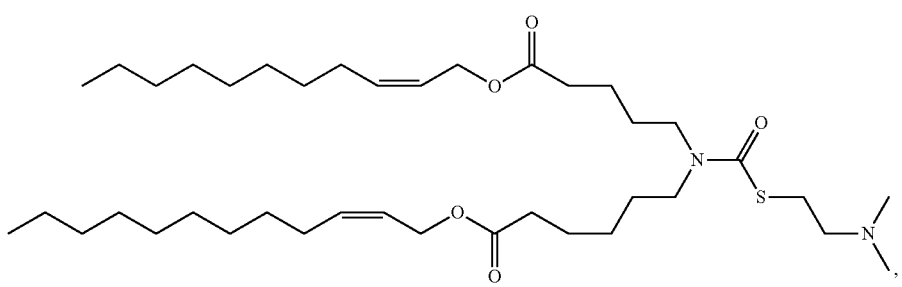
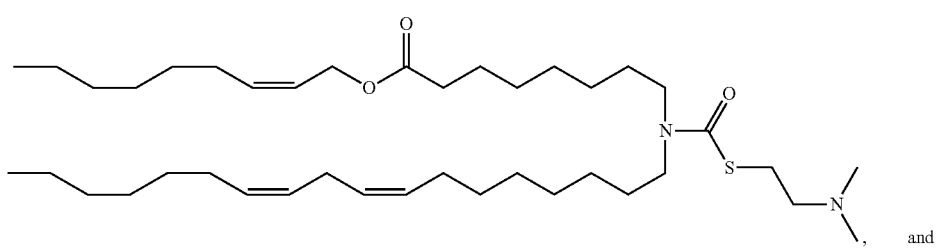
and

-continued
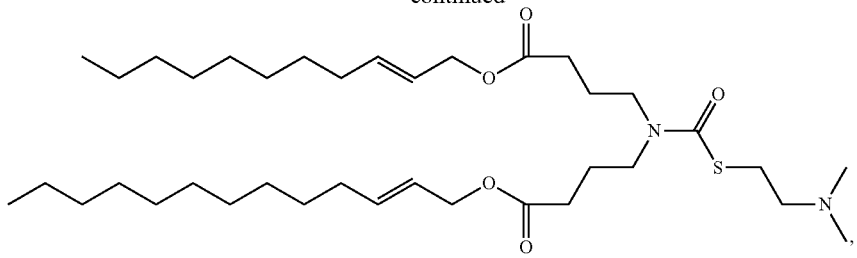
or a pharmaceutically acceptable salt or solvate thereof.
In some embodiments, the cationic lipid is
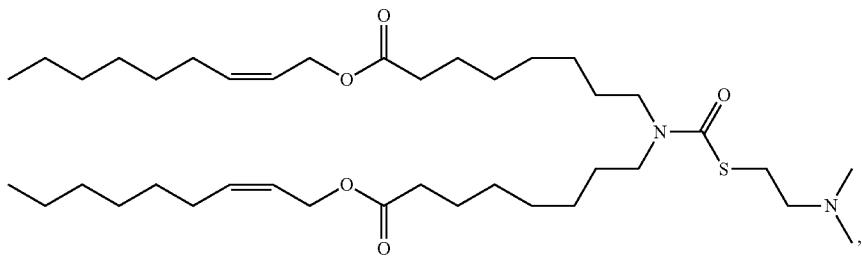 [SMILES: CCCCCC/C=C\COC(=O)CCCCCCCN(CCCCCCCC(=O)OC/C=C\CCCCCC)C(=O)SCCN(C)C]
or a pharmaceutically acceptable salt or solvate thereof.
In some embodiments, the cationic lipid is
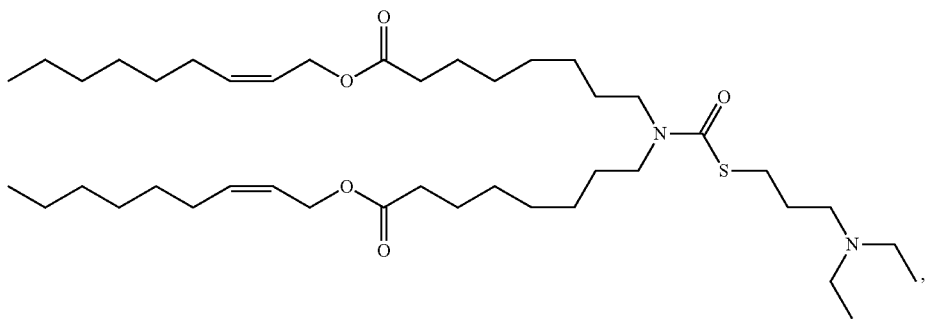 [SMILES: CCCCCC/C=C\COC(=O)CCCCCCCN(CCCCCCCC(=O)OC/C=C\CCCCCC)C(=O)SCCCN(CC)CC]
or a pharmaceutically acceptable salt or solvate thereof.
In some embodiments, the lipid is selected from the group consisting of
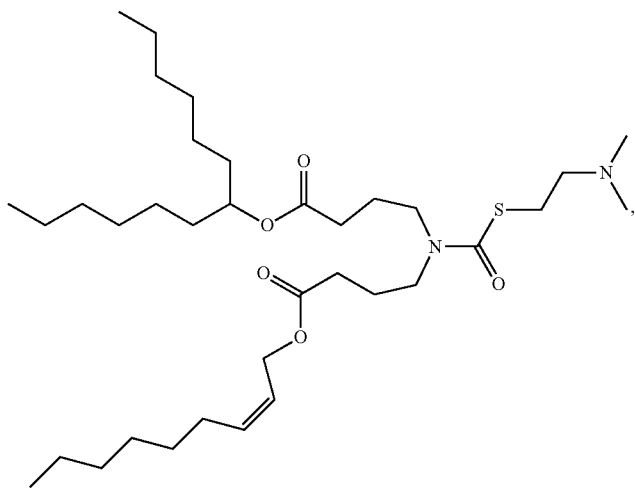

-continued
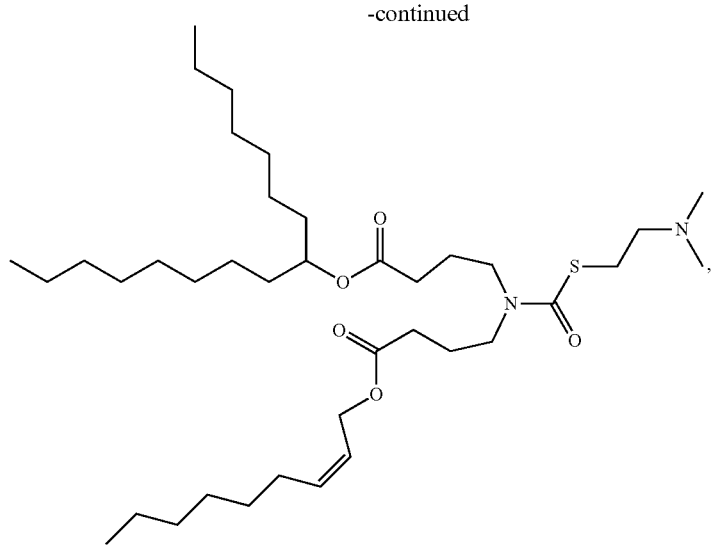
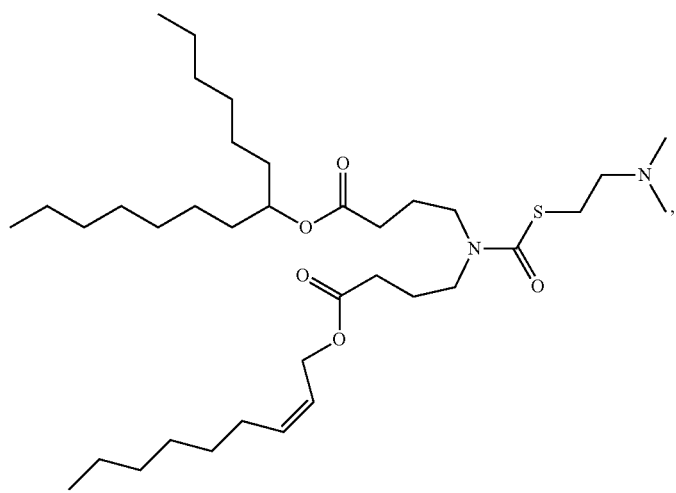
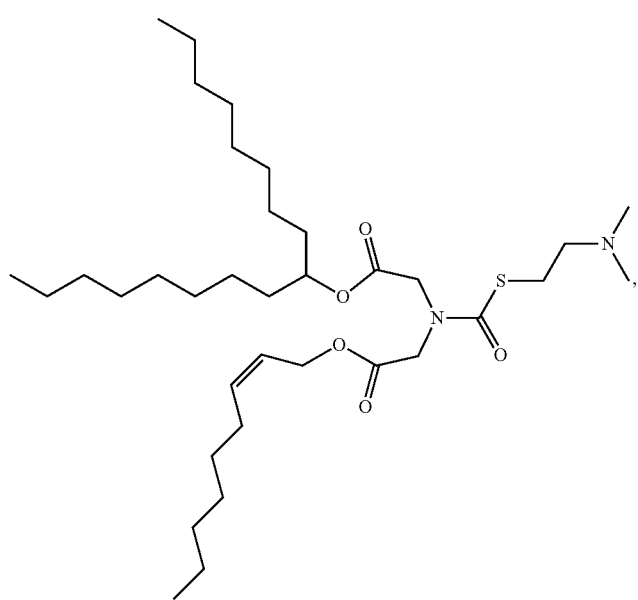

-continued
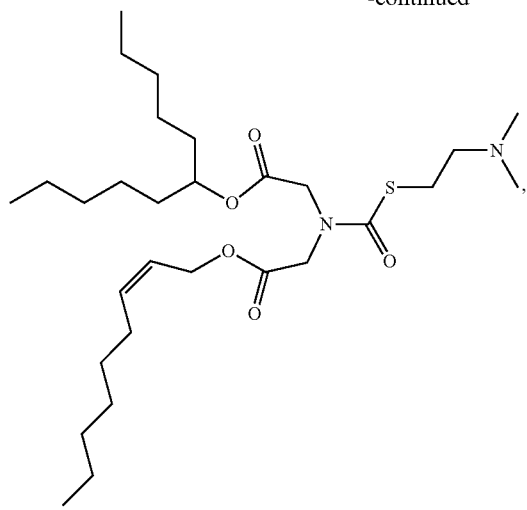
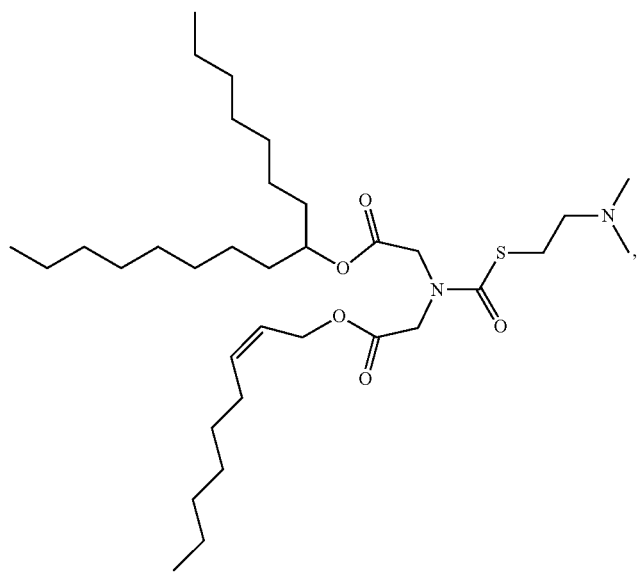
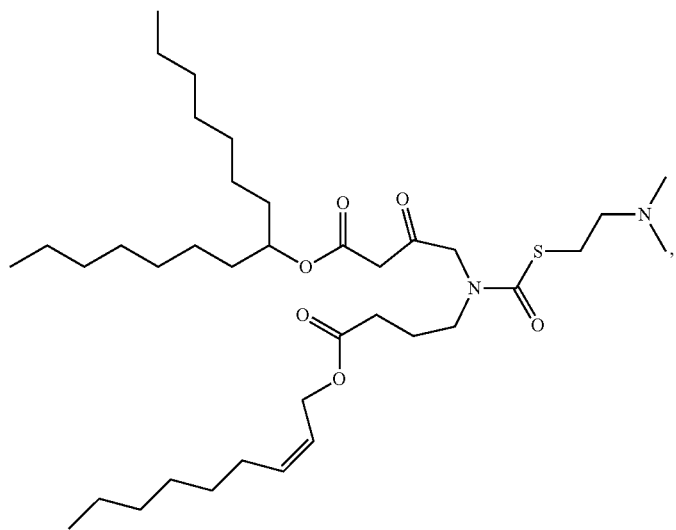

-continued
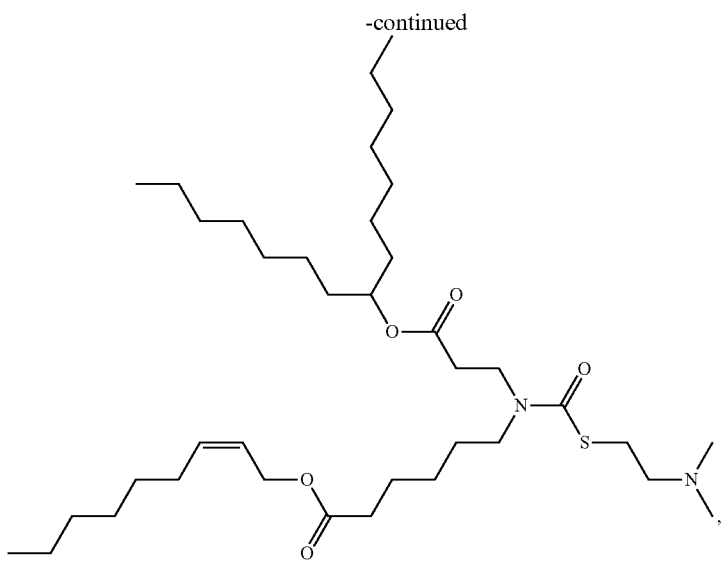
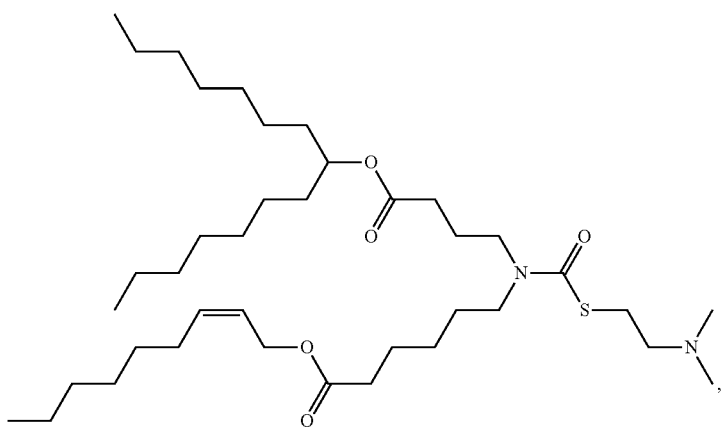
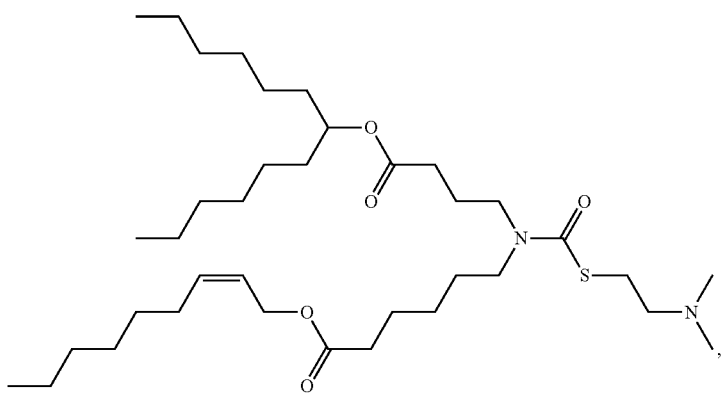

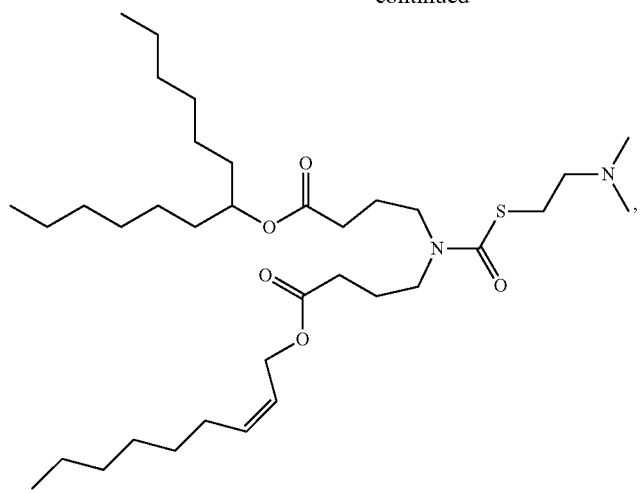
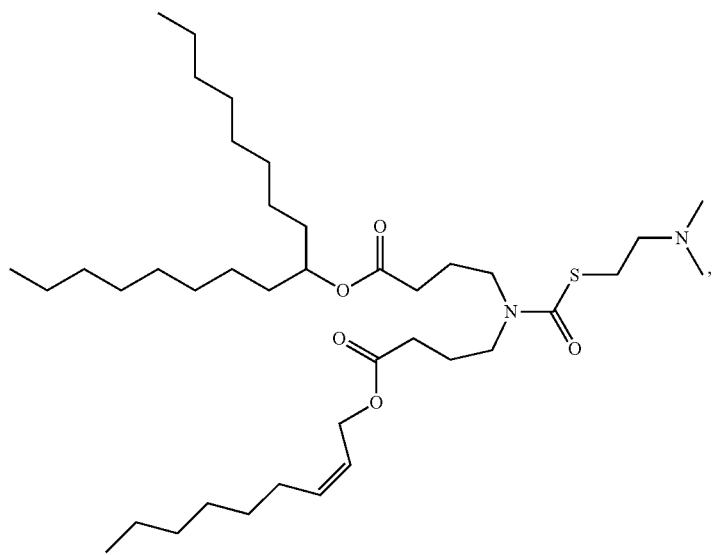
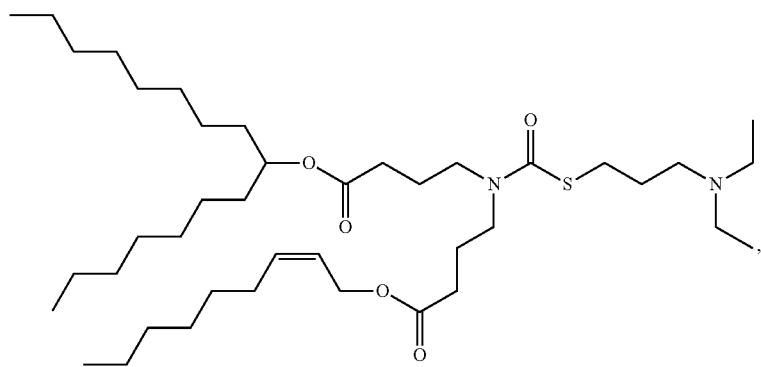

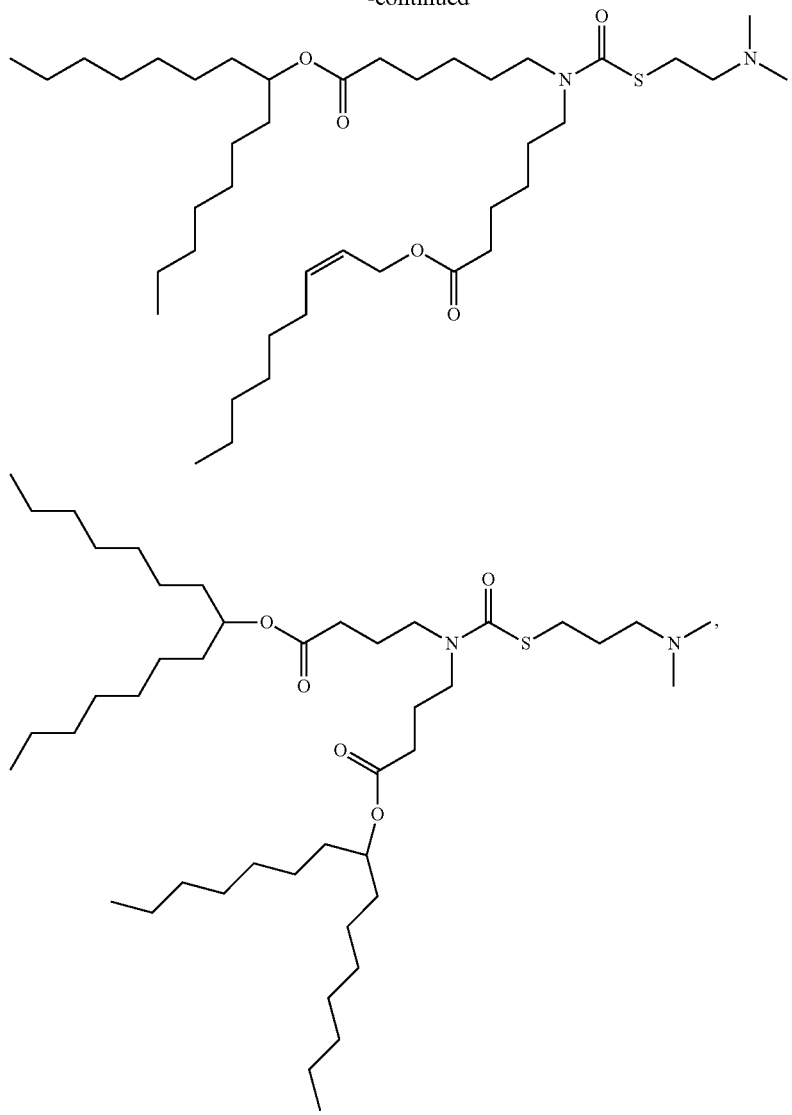
or a pharmaceutically acceptable salt or solvate thereof.
In some embodiments, the cationic lipid is
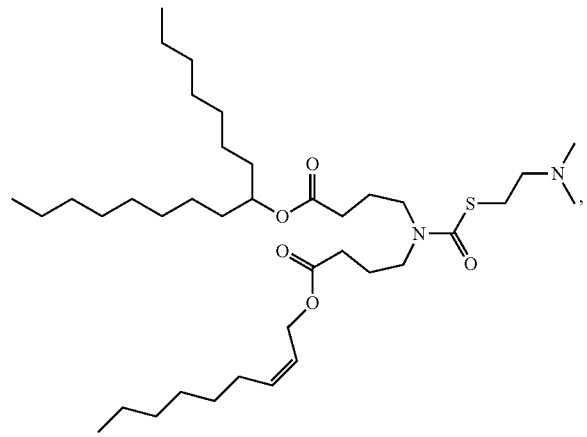 [SMILES: CCCCCC/C=C\COC(=O)CCCN(CCCC(=O)OC(CCCCCCC)CCCCCCCC)C(=O)SCCN(C)C]
or a pharmaceutically acceptable salt or solvate thereof.
In some embodiments, the cationic lipid is
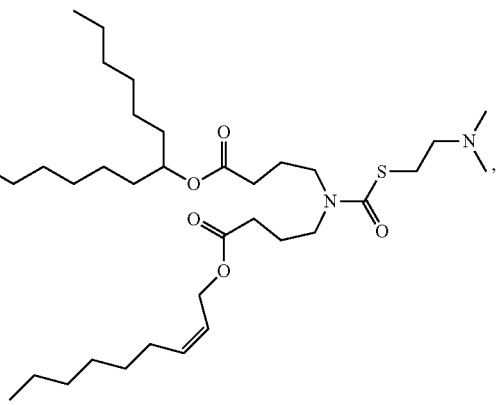
or a pharmaceutically acceptable salt or solvate thereof.

In some embodiments, the cationic lipid is

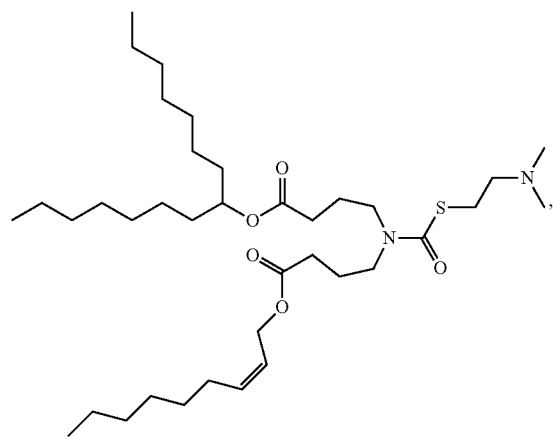 [SMILES: CCCCCC/C=C\COC(=O)CCCN(CCCC(=O)OC(CCCCCCC)CCCCCCC)C(=O)SCCN(C)C]

or a pharmaceutically acceptable salt or solvate thereof.

In some embodiments, the cationic lipid is

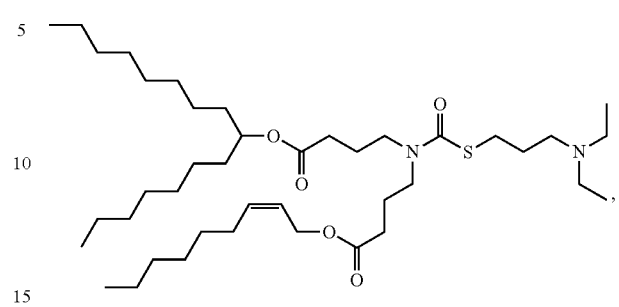

or a pharmaceutically acceptable salt or solvate thereof.

In some embodiments, the cationic lipid is

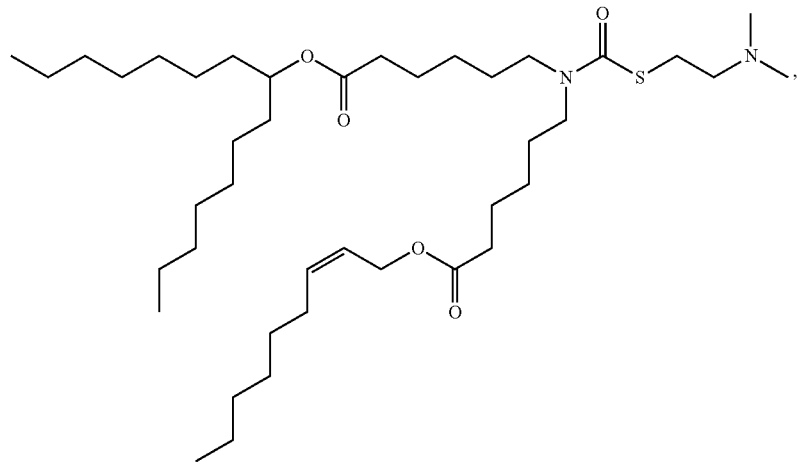 [SMILES: CCCCCC/C=C\COC(=O)CCCCCN(CCCCCC(=O)OC(CCCCCCC)CCCCCCC)C(=O)SCCN(C)C]

or a pharmaceutically acceptable salt or solvate thereof.

In some embodiments, the cationic lipid is

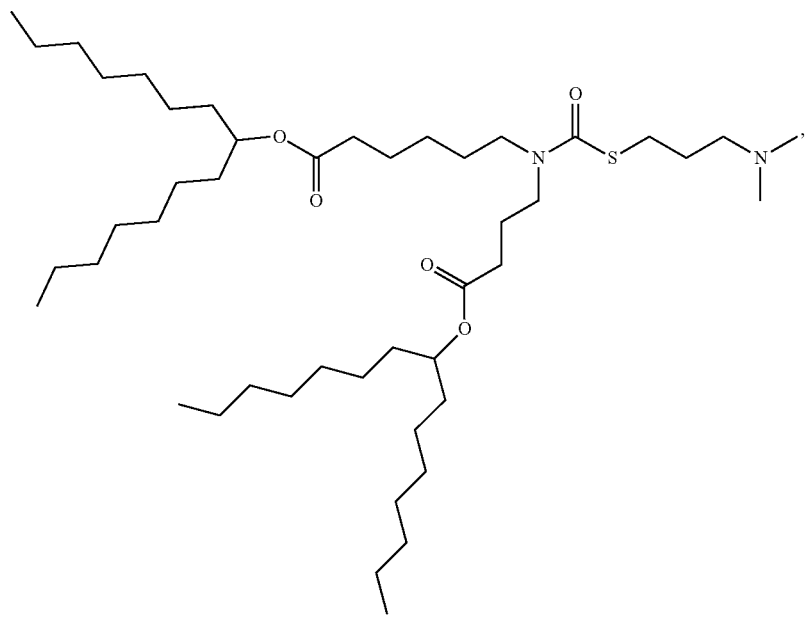 [SMILES: CCCCCCCC(CCCCCCC)OC(=O)CCCCCN(CCCC(=O)OC(CCCCCCC)CCCCCCC)C(=O)SCCCN(C)C]

or a pharmaceutically acceptable salt or solvate thereof.

In some embodiments, the lipid-encapsulated RNA nanoparticle has an average particle size of less than about 100 nm. In some embodiments, the lipid-encapsulated RNA nanoparticle has an average particles size of about 55 nm to about 85 nm.

In some embodiments, the lipid-encapsulated RNA nanoparticle encapsulates at least about 50% of the RNA. In some embodiments, the lipid-encapsulated RNA nanoparticle encapsulates at least about 85% of the RNA.

In some embodiments, the lipid-encapsulated RNA nanoparticle further comprises a helper lipid selected from the group consisting of dioleoylphosphatidyl ethanolamine (DOPE), dimyristoylphosphatidyl choline (DMPC), distearoylphosphatidyl choline (DSPC), dimyristoylphosphatidyl glycerol (DMPG), dipalmitoyl phosphatidylcholine (DPPC), and phosphatidylcholine (PC). In some embodiments, the helper lipid is distearoylphosphatidylcholine (DSPC).

In some embodiments, the lipid-encapsulated RNA nanoparticle further comprises cholesterol.

In some embodiments, the lipid-encapsulated RNA nanoparticle further comprises a polyethylene glycol (PEG)-lipid conjugate. In some embodiments, the PEG-lipid conjugate is PEG-DMG. In some embodiments, the PEG-DMG is PEG2000-DMG (Dimyristoyl glycerol).

In some embodiments, the lipid portion of the lipid-encapsulated RNA nanoparticle comprises about 48 mol % to about 66 mol % of an ionizable cationic lipid, about 2 mol % to about 12 mol % DSPC, about 25 mol % to about 42 mol % cholesterol, and about 0.5 mol % to about 3 mol % PEG2000-DMG. In some embodiments, the lipid portion of the lipid-encapsulated RNA nanoparticle comprises about 50 mol % to about 61 mol % of an ionizable cationic lipid, about 5 mol % to about 9 mol % DSPC, about 29 mol % to about 38 mol % cholesterol, and about 1 mol % to about 2 mol % PEG2000-DMG. In some embodiments, the lipid portion of the lipid-encapsulated RNA nanoparticle comprises about 56 mol % to about 58 mol % of an ionizable cationic lipid, about 6 mol % to about 8 mol % DSPC, about 31 mol % to about 34 mol % cholesterol, and about 1.25 mol % to about 1.75 mol % PEG2000-DMG.

In some embodiments, the lipid-encapsulated RNA nanoparticle has a total lipid:RNA weight ratio of about 50:1 to about 3:1. In some embodiments, the lipid-encapsulated RNA nanoparticle has a total lipid:RNA weight ratio of about 50:1 to about 5:1. In some embodiments, the lipid-encapsulated RNA nanoparticle has a total lipid:RNA weight ratio of about 50:1 to about 10:1. In some embodiments, the lipid-encapsulated RNA nanoparticle has a total lipid:RNA weight ratio of about 40:1 to about 20:1. In some embodiments, the lipid-encapsulated RNA nanoparticle has a total lipid:RNA weight ratio of about 35:1 to about 25:1. In some embodiments, the lipid-encapsulated RNA nanoparticle has a total lipid:RNA weight ratio of about 28:1 to about 32:1. In some embodiments, the lipid-encapsulated RNA nanoparticle has a total lipid:RNA weight ratio of about 29:1 to about 31:1.

In some embodiments, the lipid-encapsulated RNA nanoparticle comprises a cationic lipid:DOTAP:DSPC:Cholesterol:PEG at molar percentages of 25:25:10:38.5:1.5, 25:25:10:37:3, 25:25:10:35:5, 20:20:7:51.5:1.5, 25:20:10:42:3, 20:30:13:32:5, 25:20:10:40:5, 25:25:13:35.5:1.5, 25:30:7:35:3, 30:20:13:34:3, 30:25:7:33:3, 30:30:10:25.8:1.5, 15:20:13:49:3, 20:20:13:44:3, 20:25:13:39:3, 15:25:13:44:3, 20:25:13:39:3, 25:25:13:34:3, 30:20:13:34:3, or 30:30:13:29:3.

In some embodiments, the lipid-encapsulated RNA nanoparticle comprises between about 20 w/w % and 60 w/w % of the cationic lipid. In some embodiments, the lipid-encapsulated RNA nanoparticle comprises less than about 90 w/w % of the cationic lipid.

In some embodiments, the lipid-encapsulated RNA nanoparticle comprises between about 5 w/w % and 30 w/w % of a helper lipid.

In some embodiments, the lipid-encapsulated RNA nanoparticle comprises between about 0 w/w % and 60 w/w % of a cholesterol.

In some embodiments, the lipid-encapsulated RNA nanoparticle comprises between about 0.5 w/w % and 15 w/w % of a polyethylene glycol (PEG).

In some embodiments, the lipid-encapsulated RNA nanoparticle comprises between about 5 w/w % and 25 w/w % of a neutral lipid.

In some embodiments, the lipid-encapsulated RNA nanoparticle comprises between about 0 w/w % and 30 w/w % of a phospholipid.

In some embodiments, the lipid-encapsulated RNA nanoparticle comprises a molar ratio of between about 1.5:1 and 9:1 of cholesterol:RNA.

In some embodiments, the lipid-encapsulated RNA nanoparticle comprises a molar ratio of between about 0.5:1 and 5:1 of PEG:mRNA.

In some embodiments, the lipid-encapsulated RNA nanoparticle comprises a molar ratio of between about 0.25:1 and 4:1 of helper lipid:RNA.

In some embodiments, the lipid-encapsulated RNA nanoparticle comprises a molar ratio of between about 1:1 and 7:1 of a cationic lipid:RNA. In some embodiments, the lipid-encapsulated RNA nanoparticle comprises between about 10 w/w % and 98 w/w % of a cationic lipid of Formula I. In some embodiments, the lipid-encapsulated RNA nanoparticle comprises a molar ratio of between about 5.4:1 and 15.4:1 of a cationic lipid:RNA. In some embodiments, the lipid-encapsulated RNA nanoparticle comprises a cationic lipid Mol % and/or a ratio of cationic lipid:RNA as presented in FIG. 2. In some embodiments, the lipid-encapsulated RNA nanoparticle comprises a cationic lipid composition and/or a lipid Mol % as presented in FIG. 3.

In some embodiments, the RNA is selected from the group consisting of a tRNA (transfer RNA), snRNA (small nuclear RNA), rRNA (ribosomal RNA), mRNA (messenger RNA), antisense RNA, siRNA (small interfering RNA) and self-replicating RNA.

In some embodiments, a average particle size is less than 70 nm, 80 nm, 90 nm, or 100 nm.

In some embodiments, a polydispersity index is less than 0.05, 0.07, or 0.09.

In some embodiments, a percentage of encapsulated RNA is greater than 90%, 94%, 96%, or 98%.

In some embodiments, a batch size is 0.05 to 100 g RNA. In some embodiments, a batch size is 0.05 to 30 g RNA.

In some embodiments, a variability of average particle size between batches is less than 10%.

Natural and Modified Nucleotides

Preferably an mRNA described herein comprises one or more chemically modified nucleotides. Examples of nucleic acid monomers include non-natural, modified, and chemically-modified nucleotides, including any such nucleotides known in the art. Nucleotides can be artificially modified at either the base portion or the sugar portion. In nature, most polynucleotides comprise nucleotides that are "unmodified" or "natural" nucleotides, which include the purine bases adenine (A) and guanine (G), and the pyrimidine bases thymine (T), cytosine (C) and uracil (U). These bases are typically fixed to a ribose or deoxy ribose at the 1' position. The use of mRNA polynucleotides comprising chemically modified nucleotides have been shown to improve mRNA expression, expression rates, half-life and/or expressed protein concentrations. mRNA polynucleotides comprising chemically modified nucleotides have also been useful in optimizing protein localization thereby avoiding deleterious bio-responses such as immune responses and/or degradation pathways.

Examples of modified or chemically-modified nucleotides include 5-hydroxycytidines, 5-alkylcytidines, 5-hydroxyalkylcytidines, 5-carboxycytidines, 5-formylcytidines, 5-alkoxycytidines, 5-alkynylcytidines, 5-halocytidines, 2-thiocytidines, N4-alkylcytidines, $N^4$-aminocytidines, $N^4$-acetylcytidines, and $N^4,N^4$-dialkylcytidines.

Examples of modified or chemically-modified nucleotides include 5-hydroxycytidine, 5-methylcytidine, 5-hydroxymethylcytidine, 5-carboxycytidine, 5-formylcytidine, 5-methoxycytidine, 5-propynylcytidine, 5-bromocytidine, 5-iodocytidine, 2-thiocytidine; $N^4$-methylcytidine, $N^4$-aminocytidine, $N^4$-acetylcytidine, and $N^4,N^4$-dimethylcytidine.

Examples of modified or chemically-modified nucleotides include 5-hydroxyuridines, 5-alkyluridines, 5-hydroxyalkyluridines, 5-carboxyuridines, 5-carboxyalkylesteruridines, 5-formyluridines, 5-alkoxyuridines, 5-alkynyluridines, 5-halouridines, 2-thiouridines, and 6-alkyluridines.

Examples of modified or chemically-modified nucleotides include 5-hydroxyuridine, 5-methyluridine, 5-hydroxymethyluridine, 5-carboxyuridine, 5-carboxymethylesteruridine, 5-formyluridine, 5-methoxyuridine (also referred to herein as "5MeOU"), 5-propynyluridine, 5-bromouridine, 5-fluorouridine, 5-iodouridine, 2-thiouridine, and 6-methyluridine.

Examples of modified or chemically-modified nucleotides include 5-methoxycarbonylmethyl-2-thiouridine, 5-methylaminomethyl-2-thiouridine, 5-carbamoylmethyluridine, 5-carbamoylmethyl-2'-O-methyluridine, 1-methyl-3-(3-amino-3-carboxypropy)pseudouridine, 5-methylaminomethyl-2-selenouridine, 5-carboxymethyluridine, 5-methyldihydrouridine, 5-taurinomethyluridine, 5-taurinomethyl-2-thiouridine, 5-(isopentenylaminomethyl)uridine, 2'-O-methylpseudouridine, 2-thio-2'O-methyluridine, and 3,2'-O-dimethyluridine.

Examples of modified or chemically-modified nucleotides include $N^6$-methyladenosine, 2-aminoadenosine, 3-methyladenosine, 8-azaadenosine, 7-deazaadenosine, 8-oxoadenosine, 8-bromoadenosine, 2-methylthio-$N^6$-methyladenosine, $N^6$-isopentenyladenosine, 2-methylthio-$N^6$-isopentenyladenosine, $N^6$-(cis-hydroxyisopentenyl) adenosine, 2-methylthio-$N^6$-(cis-hydroxyisopentenyl) adenosine, $N^6$-glycinylcarbamoyladenosine, $N^6$-threonylcarbamoyl-adenosine, $N^6$-methyl-$N^6$-threonylcarbamoyl-adenosine, 2-methylthio-$N^6$-threonylcarbamoyl-adenosine, $N^6,N^6$-dimethyladenosine, $N^6$-hydroxynorvalylcarbamoyladenosine, 2-methylthio-$N^6$-hydroxynorvalylcarbamoyl-adenosine, $N^6$-acetyl-adenosine, 7-methyl-adenine, 2-methylthio-adenine, 2-methoxy-adenine, alpha-thio-adenosine, 2'-O-methyl-adenosine, $N^6$,2'-O-dimethyl-adenosine, $N^6,N^6$,2'-O-trimethyl-adenosine, 1,2'-O-dimethyl-adenosine, 2'-O-ribosyladenosine, 2-amino-$N^6$-methyl-purine, 1-thio-adenosine, 2'-F-ara-adenosine, 2'-F-adenosine, 2'-OH-ara-adenosine, and $N^6$-(19-amino-pentaoxanonadecyl)-adenosine.

Examples of modified or chemically-modified nucleotides include N'-alkylguanosines, $N^2$-alkylguanosines, thienoguanosines, 7-deazaguanosines, 8-oxoguanosines, 8-bromoguanosines, 06-alkylguanosines, xanthosines, inosines, and N'-alkylinosines.

Examples of modified or chemically-modified nucleotides include N'-methylguanosine, $N^2$-methylguanosine, thienoguanosine, 7-deazaguanosine, 8-oxoguanosine, 8-bromoguanosine, 06-methylguanosine, xanthosine, inosine, and N'-methylinosine.

Examples of modified or chemically-modified nucleotides include pseudouridines. Examples of pseudouridines include N'-alkylpseudouridines, N'-cycloalkylpseudouridines, $N^1$-hydroxypseudouridines, $N^1$-hydroxyalkylpseudouridines, N'-phenylpseudouridines, N'-phenylalkylpseudouridines, N'-aminoalkylpseudouridines, $N^3$-alkylpseudouridines, $N^6$-alkylpseudouridines, $N^6$-alkoxypseudouridines, $N^6$-hydroxypseudouridines, $N^6$-hydroxyalkylpseudouridines, $N^6$-morpholinopseudouridines, $N^6$-phenylpseudouridines, and $N^6$-halopseudouridines. Examples of pseudouridines include N'-alkyl-$N^6$-alkylpseudouridines, N'-alkyl-$N^6$-alkoxypseudouridines, N'-alkyl-$N^6$-hydroxypseudouridines, N'-alkyl-$N^6$-hydroxyalkylpseudouridines, N'-alkyl-$N^6$-morpholinopseudouridines, N'-alkyl-$N^6$-phenylpseudouridines, and N'-alkyl-$N^6$-halopseudouridines. In these examples, the alkyl, cycloalkyl, and phenyl substituents may be unsubstituted, or further substituted with alkyl, halo, haloalkyl, amino, or nitro substituents.

Examples of pseudouridines include N'-methylpseudouridine (also referred to herein as "N1MPU"), N'-ethylpseudouridine, N'-propylpseudouridine, N'-cyclopropylpseudouridine, N'-phenylpseudouridine, N1-aminomethylpseudouridine, $N^3$-methylpseudouridine, $N^1$-hydroxypseudouridine, and $N^1$-hydroxymethylpseudouridine.

Examples of nucleic acid monomers include modified and chemically-modified nucleotides, including any such nucleotides known in the art.

Examples of modified and chemically-modified nucleotide monomers include any such nucleotides known in the art, for example, 2'-O-methyl ribonucleotides, 2'-O-methyl purine nucleotides, 2'-deoxy-2'-fluoro ribonucleotides, 2'-deoxy-2'-fluoro pyrimidine nucleotides, 2'-deoxy ribonucleotides, 2'-deoxy purine nucleotides, universal base nucleotides, 5-C-methyl-nucleotides, and inverted deoxyabasic monomer residues.

Examples of modified and chemically-modified nucleotide monomers include 3'-end stabilized nucleotides, 3'-glyceryl nucleotides, 3'-inverted abasic nucleotides, and 3'-inverted thymidine.

Examples of modified and chemically-modified nucleotide monomers include locked nucleic acid nucleotides (LNA), 2'-O,4'-C-methylene-(D-ribofuranosyl) nucleotides, 2'-methoxyethoxy (MOE) nucleotides, 2'-methyl-thio-ethyl, 2'-deoxy-2'-fluoro nucleotides, and 2'-O-methyl nucleotides. In an exemplary embodiment, the modified monomer is a locked nucleic acid nucleotide (LNA).

Examples of modified and chemically-modified nucleotide monomers include 2',4'-constrained 2'-O-methoxyethyl (cMOE) and 2'-O-Ethyl (cEt) modified DNAs.

Examples of modified and chemically-modified nucleotide monomers include 2'-amino nucleotides, 2'-O-amino nucleotides, 2'-C-allyl nucleotides, and 2'-O-allyl nucleotides.

Examples of modified and chemically-modified nucleotide monomers include $N^6$-methyladenosine nucleotides.

Examples of modified and chemically-modified nucleotide monomers include nucleotide monomers with modified bases 5-(3-amino)propyluridine, 5-(2-mercapto)ethyluridine, 5-bromouridine; 8-bromoguanosine, or 7-deazaadenosine.

Examples of modified and chemically-modified nucleotide monomers include 2'-O-aminopropyl substituted nucleotides.

Examples of modified and chemically-modified nucleotide monomers include replacing the 2'-OH group of a nucleotide with a 2'-R, a 2'-OR, a 2'-halogen, a 2'-SR, or a 2'-amino, where R can be H, alkyl, alkenyl, or alkynyl.

Example of base modifications described above can be combined with additional modifications of nucleoside or nucleotide structure, including sugar modifications and linkage modifications. Certain modified or chemically-modified nucleotide monomers may be found in nature.

Preferred nucleotide modifications include N'-methylpseudouridine and 5-methoxyuridine.

5' Cap

A Cap structure on the 5'-end of mRNAs (or self-replication RNA), which is present in all eukaryotic organisms (and some viruses) is important for stabilizing mRNAs in vivo. Naturally occurring Cap structures comprise a riboguanosine residue that is methylated at position N7 of the guanine base. This 7-methylguanosine ($m^7G$) is linked via a 5'- to 5'-triphosphate chain at the 5'-end of the mRNA molecule. The presence of the $m^7Gppp$ fragment on the 5'-end is essential for mRNA maturation as it protects the mRNAs from degradation by exonucleases, facilitates transport of mRNAs from the nucleus to the cytoplasm and plays a key role in assembly of the translation initiation complex (Cell 9:645-653, (1976); Nature 266:235, (1977); Federation of Experimental Biologists Society Letter 96:1-11, (1978); Cell 40:223-24, (1985); Prog. Nuc. Acid Res. 35:173-207, (1988); Ann. Rev. Biochem. 68:913-963, (1999); and J Biol. Chem. 274:30337-3040, (1999)).

Only those mRNAs that carry the Cap structure are active in Cap dependent translation; "decapitation" of mRNA results in an almost complete loss of their template activity for protein synthesis (Nature, 255:33-37, (1975); J. Biol. Chem., vol. 253:5228-5231, (1978); and Proc. Natl. Acad. Sci. USA, 72:1189-1193, (1975)).

Another element of eukaryotic mRNA is the presence of 2'-O-methyl nucleoside residues at transcript position 1 (Cap 1), and in some cases, at transcript positions 1 and 2 (Cap 2). The 2'-O-methylation of mRNA provides higher efficacy of mRNA translation in vivo (Proc. Natl. Acad. Sci. USA, 77:3952-3956 (1980)) and further improves nuclease stability of the 5'-capped mRNA. The mRNA with Cap 1 (and Cap 2) is a distinctive mark that allows cells to recognize the bona fide mRNA 5' end, and in some instances, to discriminate against transcripts emanating from infectious genetic elements (Nucleic Acid Research 43: 482-492 (2015)).

Some examples of 5' cap structures and methods for preparing mRNAs comprising the same are given in WO 2015/051169A2, WO 2015/061491, US 2018/0273576, and U.S. Pat. Nos. 8,093,367, 8,304,529, and 10,487,105. In some embodiments, the 5' cap is $m^7GpppAmpG$, which is known in the art. In some embodiments, the 5' cap is $m^7GpppG$ or $m^7GpppGm$, which are known in the art. Structural formulas for embodiments of 5' cap structures are provided below.

In some embodiments, an mRNA described herein comprises a 5' cap having the structure of Formula (Cap I).

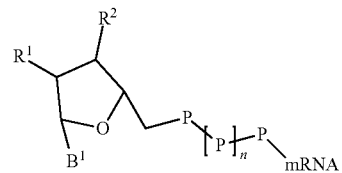

(Cap I)

wherein $B^1$ is a natural or modified nucleobase; $R^1$ and $R^2$ are each independently selected from a halogen, OH, and $OCH_3$; each P is independently selected from the group consisting of phosphate, phophorothioate, and boranophosphate; n is 0, 1, 2 or 3; mRNA represents an mRNA of the present disclosure linked at its 5' end. In some embodiments $B^1$ is G, $m^7G$, or A. In some embodiments, n is 0. In some embodiments, $B^1$ is A or $m^6A$ and $R^1$ is $OCH_3$; wherein G is guanine, $m^7G$ is 7-methylguanine, A is adenine, and $m^6A$ is $N^6$-methyladenine.

In some embodiments, an mRNA described herein comprises a 5' cap having the structure of Formula (Cap II).

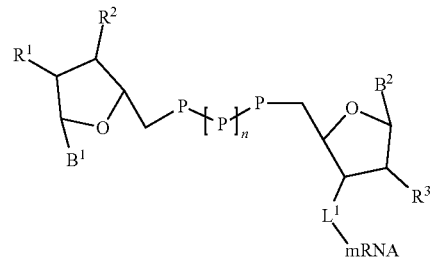

(Cap II)

wherein $B^1$ and $B^2$ are each independently a natural or modified nucleobase; $R^1$, $R^2$, and $R^3$ are each independently selected from a halogen, OH, and $OCH_3$; each P is independently selected from the group consisting of phosphate, phophorothioate, and boranophosphate; mRNA represents an mRNA of the present disclosure linked at its 5' end; n is 0, 1, 2 or 3; and $L^1$ is a phosphate, a phosphorothioate, or a boranophospate, wherein at least one of $R^1$, $R^2$, and $R^3$ is OH. In some embodiments $B^1$ is G, $m^7G$, or A. In some embodiments, n is 0. In some embodiments, $B^1$ is A or $m^6A$ and $R^1$ is $OCH_3$; wherein G is guanine, $m^7G$ is 7-methylguanine, A is adenine, and $m^6A$ is $N^6$-methyladenine.

In some embodiments, an mRNA described herein comprises a 5' cap having the structure of Formula (Cap III).

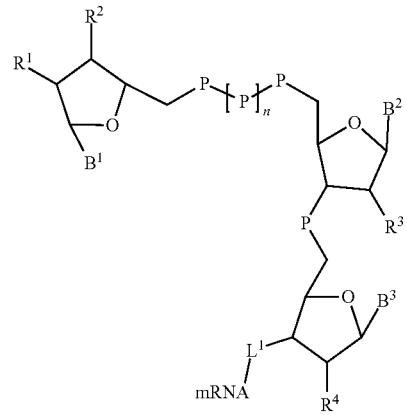

(Cap III)

wherein B¹, B², and B³ are each independently a natural or modified nucleobase; R¹, R², R³, and R⁴ are each independently selected from a halogen, OH, and OCH₃; each P is independently selected from the group consisting of phosphate, phosphorothioate, and boranophosphate; mRNA represents an mRNA of the present disclosure linked at its 5' end; n is 0, 1, 2 or 3; and L¹ is a phosphate, a phosphorothioate, or a boranophospate, wherein at least one of R¹, R², R³, and R⁴ is OH. In some embodiments B¹ is G, m⁷G, or A. In some embodiments, B¹ is A or m⁶A and R¹ is OCH₃; wherein G is guanine, m⁷G is 7-methylguanine, A is adenine, and m⁶A is N⁶-methyladenine. In some embodiments, n is 1.

In some embodiments, an mRNA described herein comprises a m⁷GppppG 5' cap analog having the structure of Formula (Cap IV).

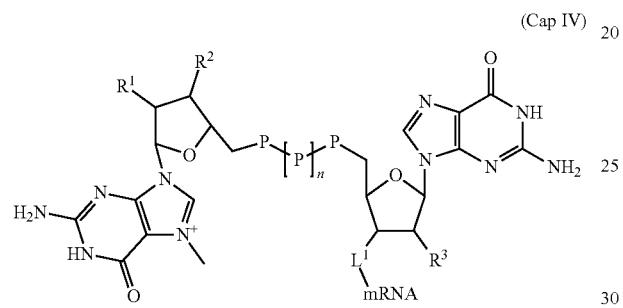

(Cap IV)

wherein, R¹, R², and R³ are each independently selected from a halogen, OH, and OCH₃; each P is independently selected from the group consisting of phosphate, phosphorothioate, and boranophosphate; mRNA represents an mRNA of the present disclosure linked at its 5' end; n is 0, 1, 2 or 3; and L¹ is a phosphate, a phosphorothioate, or a boranophospate, wherein at least one of R¹, R², and R³ is OH. In some embodiments, the 5' cap is m⁷GpppG wherein R¹, R², and R³ are each OH, n is 1, and L¹ is phosphate. In some embodiments, n is 1. In some embodiments, R¹ and R² are each OH, R³ is OCH₃, each P is a phosphate whereby phosphodiester bonds are formed, mRNA is an mRNA of the present disclosure linked at its 5' end, n is 1, and L¹ is a phosphate.

In some embodiments, an mRNA described herein comprises a m⁷Gpppm⁷G 5' cap analog having the structure of Formula (Cap V).

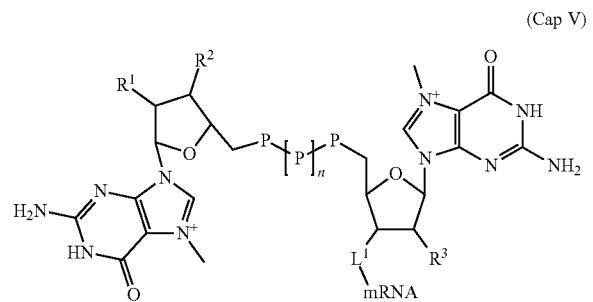

(Cap V)

wherein, R¹, R², and R³ are each independently selected from a halogen, OH, and OCH₃; each P is independently selected from the group consisting of phosphate, phosphorothioate, and boranophosphate; mRNA represents an mRNA of the present disclosure linked at its 5' end; n is 0, 1, 2 or 3; and L¹ is a phosphate, a phosphorothioate, or a boranophospate, wherein at least one of R¹, R², and R³ is OH. In some embodiments, n is 0.

In some embodiments, an mRNA described herein comprises a m⁷Gpppm⁷GpN, 5' cap analog, wherein N is a natural or modified nucleotide, the 5' cap analog having the structure of Formula (Cap VI).

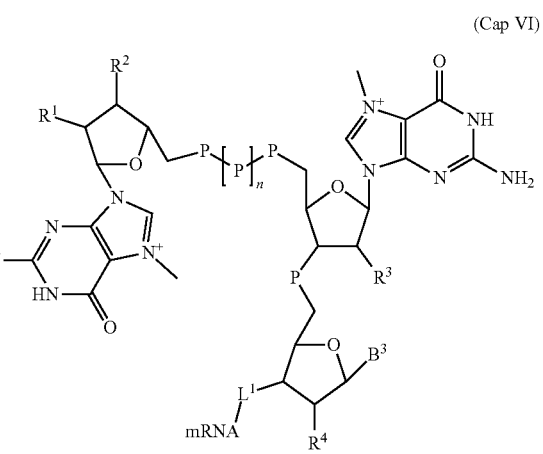

(Cap VI)

wherein B³ is a natural or modified nucleobase; R¹, R², R³, and R⁴ are each independently selected from a halogen, OH, and OCH₃; each P is independently selected from the group consisting of phosphate, phosphorothioate, and boranophosphate; mRNA represents an mRNA of the present disclosure linked at its 5' end; n is 0, 1, 2 or 3; and L¹ is a phosphate, a phosphorothioate, or a boranophospate, wherein at least one of R¹, R², R³, and R⁴ is OH. In some embodiments B¹ is G, m⁷G, or A. In some embodiments, B¹ is A or m⁶A and R¹ is OCH₃; wherein G is guanine, m⁷G is 7-methylguanine, A is adenine, and m⁶A is N⁶-methyladenine. In some embodiments, n is 1.

In some embodiments, an mRNA described herein comprises a m⁷Gpppm⁷GpG 5' cap analog having the structure of Formula (Cap VII).

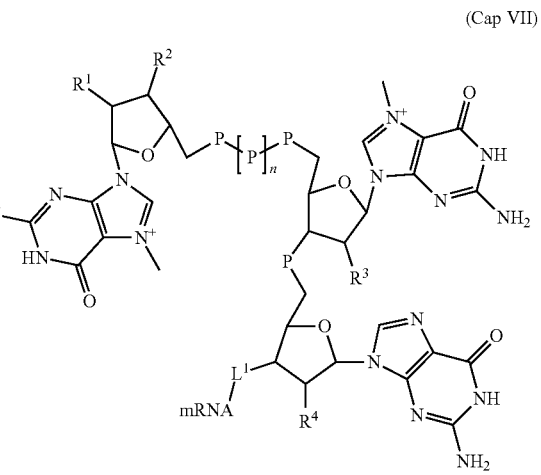

(Cap VII)

wherein, R¹, R², R³, and R⁴ are each independently selected from a halogen, OH, and OCH₃; each P is independently selected from the group consisting of phosphate, phosphorothioate, and boranophosphate; mRNA represents an mRNA of the present disclosure linked at its 5' end; n is 0, 1, 2 or 3; and L¹ is a phosphate, a phosphorothioate, or a boranophospate, wherein at least one of R¹, R², R³, and R⁴ is OH. In some embodiments, n is 1.

In some embodiments, an mRNA described herein comprises a m⁷Gpppm⁷Gpm⁷G 5' cap analog having the structure of Formula (Cap VIII).

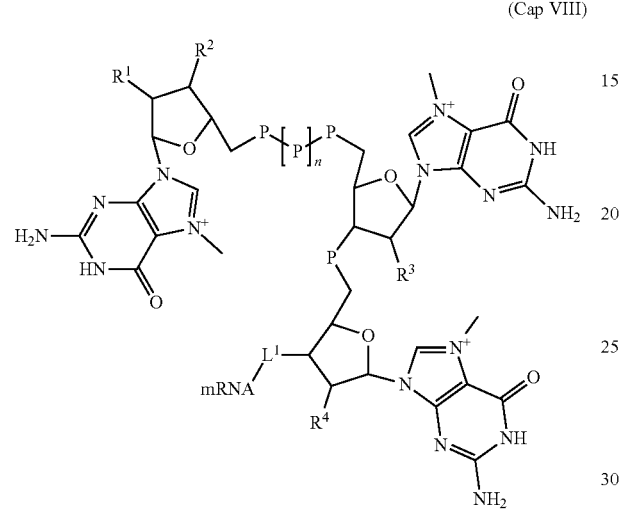

(Cap VIII)

wherein, R¹, R², R³, and R⁴ are each independently selected from a halogen, OH, and OCH₃; each P is independently selected from the group consisting of phosphate, phosphorothioate, and boranophosphate; mRNA represents an mRNA of the present disclosure linked at its 5' end; n is 0, 1, 2 or 3; and L¹ is a phosphate, a phosphorothioate, or a boranophospate, wherein at least one of R¹, R², R³, and R⁴ is OH. In some embodiments, n is 1.

In some embodiments, an mRNA described herein comprises a m⁷GpppA 5' cap analog having the structure of Formula (Cap IX).

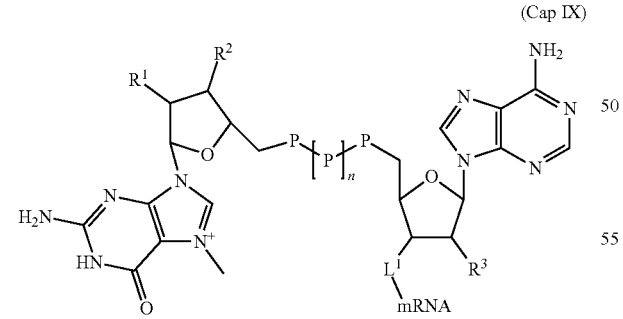

(Cap IX)

wherein, R¹, R², and R³ are each independently selected from a halogen, OH, and OCH₃; each P is independently selected from the group consisting of phosphate, phosphorothioate, and boranophosphate; mRNA represents an mRNA of the present disclosure linked at its 5' end; n is 0, 1, 2 or 3; and L¹ is a phosphate, a phosphorothioate, or a boranophospate, wherein at least one of R¹, R², and R³ is OH. In some embodiments, n is 1.

In some embodiments, an mRNA described herein comprises a m⁷GpppApN 5' cap analog, wherein N is a natural or modified nucleotide, and the 5' cap has the structure of Formula (Cap X).

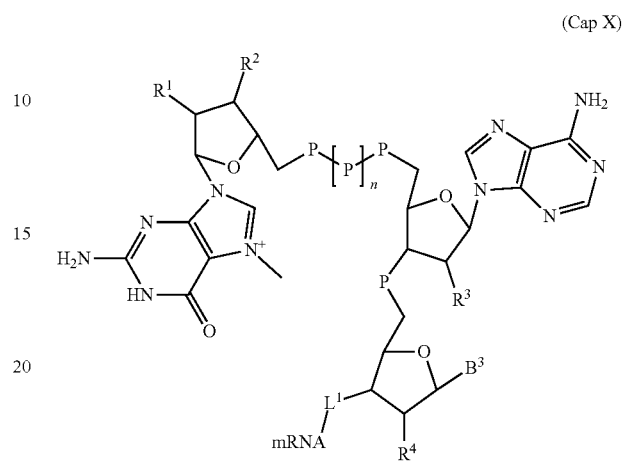

(Cap X)

wherein B³ is a natural or modified nucleobase; R¹, R², R³, and R⁴ are each independently selected from a halogen, OH, and OCH₃; each P is independently selected from the group consisting of phosphate, phosphorothioate, and boranophosphate; mRNA represents an mRNA of the present disclosure linked at its 5' end; n is 0, 1, 2 or 3; and L¹ is a phosphate, a phosphorothioate, or a boranophospate, wherein at least one of R¹, R², R³, and R⁴ is OH. In some embodiments B³ is G, m⁷G, A or m⁶A; wherein G is guanine, m⁷G is 7-methylguanine, A is adenine, and m⁶A is N⁶-methyladenine. In some embodiments, n is 1.

In some embodiments, an mRNA described herein comprises a m⁷GpppAmpG 5' cap analog having the structure of Formula (Cap XI).

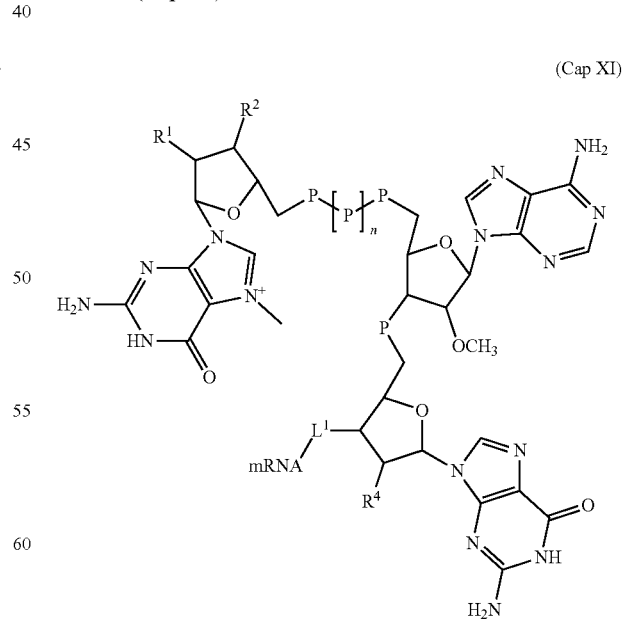

(Cap XI)

wherein, R¹, R², and R⁴ are each independently selected from a halogen, OH, and OCH₃; each P is independently selected from the group consisting of phosphate, phosphorothioate, and boranophosphate; mRNA represents an mRNA of the present disclosure linked at its 5' end; n is 0, 1, 2 or 3; and L¹ is a phosphate, a phosphorothioate, or a boranophospate, wherein at least one of R¹, R², and R⁴ is OH. In some embodiments, the compound of Formula Cap XI is m⁷GpppAmpG, wherein R¹, R², and R⁴ are each OH, n is 1, and L¹ is a phosphate linkage. In some embodiments, n is 1.

In some embodiments, an mRNA described herein comprises a m⁷GpppApm⁷G 5' cap analog having the structure of Formula (Cap XII).

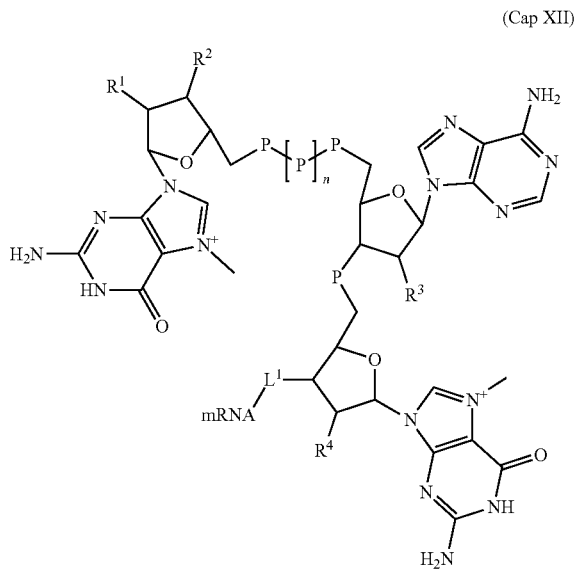

(Cap XII)

wherein, R¹, R², R³, and R⁴ are each independently selected from a halogen, OH, and OCH₃; each P is independently selected from the group consisting of phosphate, phosphorothioate, and boranophosphate; mRNA represents an mRNA of the present disclosure linked at its 5' end; n is 0, 1, 2 or 3; and L¹ is a phosphate, a phosphorothioate, or a boranophospate, wherein at least one of R¹, R², R³, and R⁴ is OH. In some embodiments, n is 1.

In some embodiments, an mRNA described herein comprises a m⁷GpppAmpm⁷G 5' cap analog having the structure of Formula (Cap XIII).

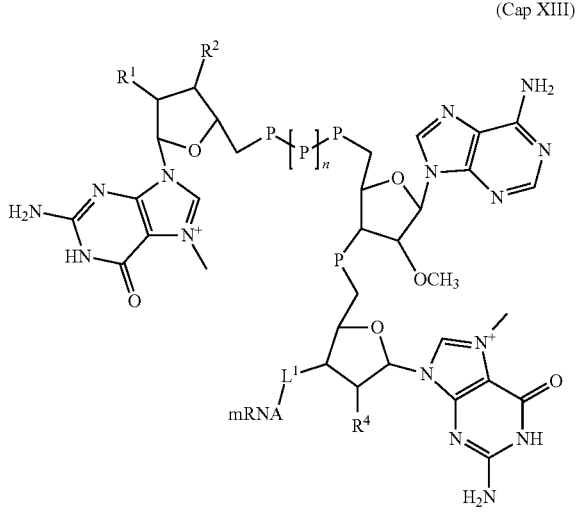

(Cap XIII)

wherein, R¹, R², and R⁴ are each independently selected from a halogen, OH, and OCH₃; each P is independently selected from the group consisting of phosphate, phosphorothioate, and boranophosphate; mRNA represents an mRNA of the present disclosure linked at its 5' end; n is 0, 1, 2 or 3; and L¹ is a phosphate, a phosphorothioate, or a boranophospate, wherein at least one of R¹, R², and R⁴ is OH. In some embodiments, n is 1.

The RNA can contain a 5' trinucleotide cap structure as described by US 2018/0105551A1, herein incorporated by reference in its entirety.

Natural RNA may have a phosphate backbone. RNA as described herein may contain other types of backbones and bases including peptide nucleic acids, phosphothionates, phosphoramidate, phosphorothioate, and/or methylphosphonate linkages.

Cationic Lipids

The lipid formulation preferably includes a cationic lipid suitable for forming a cationic liposome or lipid nanoparticle. Cationic lipids are widely studied for nucleic acid delivery because they can bind to negatively charged membranes and induce uptake. Generally, cationic lipids are amphiphiles containing a positive hydrophilic head group, two (or more) lipophilic tails, or a steroid portion and a connector between these two domains. Preferably, the cationic lipid carries a net positive charge at about physiological pH. Cationic liposomes have been traditionally the most commonly used non-viral delivery systems for oligonucleotides, including plasmid DNA, antisense oligos, and siRNA/small hairpin RNA-shRNA). Cationic lipids, such as DOTAP, (1,2-dioleoyl-3-trimethylammonium-propane) and DOTMA (N-[1-(2,3-dioleoyloxy)propyl]-N,N,N-trimethylammonium methyl sulfate) can form complexes or lipoplexes with negatively charged nucleic acids by electrostatic interaction, providing high in vitro transfection efficiency.

In the presently disclosed lipid formulations and methods of producing the same, the cationic lipid may be, for example, N,N-dioleyl-N,N-dimethylammonium chloride (DODAC), N,N-distearyl-N,N-dimethylammonium bromide (DDAB), 1,2-dioleoyltrimethylammoniumpropane chloride (DOTAP) (also known as N-(2,3-dioleoyloxy)propyl)-N,N,N-trimethylammonium chloride and 1,2-Dioleyloxy-3-trimethylaminopropane chloride salt), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-di-y-linolenyloxy-N,N-dimethylaminopropane (γ-DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanediol (DOAP), 1,2-Dilinoleyloxo-3-(2-N,N-dimethylamino)ethoxypropane (DLin-EG-DMA), 2,2-Dilinoleyl-4-dimethylaminomethyl-[1,3]-dioxolane (DLin-K-DMA) or analogs thereof, (3aR, 5s,6aS)—N,N-dimethyl-2,2-di((9Z,12Z)-octadeca-9,12-dienyl)tetrahydro-3 aH-cyclopenta[d][1,3]dioxol-5-amine, (6Z,9Z,28Z,31Z)-heptatriaconta-6,9,28,31-tetraen-19-yl4-(dimethylamino)butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (C12-200), 2,2-dilinoleyl-4-(2-dimethylaminoethyl)-[1,3]-dioxolane (DLin-K-C2-DMA), 2,2-dilinoleyl-4-dimethylaminomethyl-[1,3]-dioxolane (DLin-K-DMA), (6Z,9Z,28Z,31Z)-heptatriaconta-6,9,28,31-tetraen-19-yl 4-(dimethylamino) butanoate (DLin-M-C3-DMA), 3-((6Z,9Z,28Z,31Z)-heptatriaconta-6,9,28,31-tetraen-19-yloxy)-N,N-dimethylpropan-1-amine (MC3 Ether), 4-((6Z,9Z,28Z,31Z)-heptatriaconta-6,9,28,31-tetraen-19-yloxy)-N,N-dimethylbutan-1-amine (MC4 Ether), or any combination thereof. Other cationic lipids include, but are not limited to, N,N-distearyl-N,N-dimethylammonium bromide (DDAB), 3P-(N—(N',N'-dimethylaminoethane)-carbamoyl)cholesterol (DC-Choi), N-(1-(2,3-dioleyloxy)propyl)-N-2-(sperminecarboxamido)ethyl)-N,N-dimethylammonium trifluoroacetate (DOSPA), dioctadecylamidoglycyl carboxyspermine (DOGS), 1,2-dileoyl-sn-3-phosphoethanolamine (DOPE), 1,2-dioleoyl-3-dimethylammonium propane (DODAP), N-(1,2-dimyristyloxyprop-3-yl)-N,N-dimethyl-N-hydroxyethyl ammonium bromide (DMRIE), and 2,2-Dilinoleyl-4-dimethylaminoethyl-[1,3]-dioxolane (XTC). Additionally, commercial preparations of cationic lipids can be used, such as, e.g., LIPOFECTIN (including DOTMA and DOPE, available from GIBCO/BRL), and Lipofectamine (comprising DOSPA and DOPE, available from GIBCO/BRL).

Other suitable cationic lipids are disclosed in International Publication Nos. WO 09/086558, WO 09/127060, WO 10/048536, WO 10/054406, WO 10/088537, WO 10/129709, and WO 2011/153493; U.S. Patent Publication Nos. 2011/0256175, 2012/0128760, and 2012/0027803; U.S. Pat. No. 8,158,601; and Love et al., PNAS, 107(5), 1864-69, 2010, the contents of which are herein incorporated by reference.

Other suitable cationic lipids include those having alternative fatty acid groups and other dialkylamino groups, including those, in which the alkyl substituents are different (e.g., N-ethyl-N-methylamino-, and N-propyl-N-ethyl-amino-). These lipids are part of a subcategory of cationic lipids referred to as amino lipids. In some embodiments of the lipid formulations described herein, the cationic lipid is an amino lipid. In general, amino lipids having less saturated acyl chains are more easily sized, particularly when the complexes must be sized below about 0.3 microns, for purposes of filter sterilization. Amino lipids containing unsaturated fatty acids with carbon chain lengths in the range of C14 to C22 may be used. Other scaffolds can also be used to separate the amino group and the fatty acid or fatty alkyl portion of the amino lipid.

In some embodiments, the lipid formulation and methods of producing the same comprises the cationic lipid with Formula I according to the patent application PCT/EP2017/064066. In this context, the disclosure of PCT/EP2017/064066 is also incorporated herein by reference.

In some embodiments, amino or cationic lipids of the present disclosure are ionizable and have at least one protonatable or deprotonatable group ("ionizable cationic lipids"), such that the lipid is positively charged at a pH at or below physiological pH (e.g., pH 7.4), and neutral at a second pH, preferably at or above physiological pH. Of course, it will be understood that the addition or removal of protons as a function of pH is an equilibrium process, and that the reference to a charged or a neutral lipid refers to the nature of the predominant species and does not require that all of the lipid be present in the charged or neutral form.

Lipids that have more than one protonatable or deprotonatable group, or which are zwitterionic, are not excluded from use in the disclosure. In certain embodiments, the protonatable lipids have a pKa of the protonatable group in the range of about 4 to about 11. In some embodiments, the ionizable cationic lipid has a pKa of about 5 to about 7. In some embodiments, the pKa of an ionizable cationic lipid is about 6 to about 7.

In some embodiments, the lipid formulation and methods of producing the same comprises an ionizable cationic lipid of Formula I:

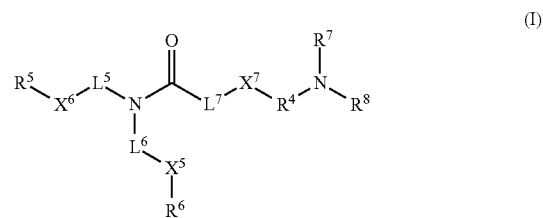

(I)

or a pharmaceutically acceptable salt or solvate thereof, wherein $R^5$ and $R^6$ are each independently selected from the group consisting of a linear or branched $C_1$-$C_{31}$ alkyl, $C_2$-$C_{31}$ alkenyl or $C_2$-$C_{31}$ alkynyl and cholesteryl; $L^5$ and $L^6$ are each independently selected from the group consisting of a linear $C_1$-$C_{20}$ alkyl and $C_2$-$C_{20}$ alkenyl; $X^5$ is —C(O)O—, whereby —C(O)O—$R^6$ is formed or —OC(O)— whereby —OC(O)—$R^6$ is formed; $X^6$ is —C(O)O— whereby —C(O)O—$R^5$ is formed or —OC(O)— whereby —OC(O)—$R^5$ is formed; $X^7$ is S or 0; $L^7$ is absent or lower alkyl; $R^4$ is a linear or branched $C_1$-$C_6$ alkyl; and $R^7$ and $R^8$ are each independently selected from the group consisting of a hydrogen and a linear or branched $C_1$-$C_6$ alkyl.

In some embodiments, $X^7$ is S.

In some embodiments, $X^5$ is —C(O)O—, whereby —C(O)O—$R^6$ is formed and $X^6$ is —C(O)O— whereby —C(O)O—$R^5$ is formed.

In some embodiments, $R^7$ and $R^8$ are each independently selected from the group consisting of methyl, ethyl and isopropyl.

In some embodiments, $L^5$ and $L^6$ are each independently a $C_1$-$C_{10}$ alkyl. In some embodiments, $L^5$ is $C_1$-$C_3$ alkyl, and $L^6$ is $C_1$-$C_5$ alkyl. In some embodiments, $L^6$ is $C_1$-$C_2$ alkyl. In some embodiments, $L^5$ and $L^6$ are each a linear $C_7$ alkyl. In some embodiments, $L^5$ and $L^6$ are each a linear $C_9$ alkyl.

In some embodiments, $R^5$ and $R^6$ are each independently an alkenyl. In some embodiments, $R^6$ is alkenyl. In some embodiments, $R^6$ is $C_2$-$C_9$ alkenyl. In some embodiments, the alkenyl comprises a single double bond. In some embodiments, $R^5$ and $R^6$ are each alkyl. In some embodiments, $R^5$ is a branched alkyl. In some embodiments, $R^5$ and $R^6$ are each independently selected from the group consisting of a $C_9$ alkyl, $C_9$ alkenyl and $C_9$ alkynyl. In some embodiments, $R^5$ and $R^6$ are each independently selected from the group consisting of a $C_{11}$ alkyl, $C_{11}$ alkenyl and $C_{11}$ alkynyl. In some embodiments, $R^5$ and $R^6$ are each independently selected from the group consisting of a $C_7$ alkyl, $C_7$ alkenyl and $C_7$ alkynyl. In some embodiments, $R^5$ is —CH(($CH_2)_p CH_3)_2$ or —CH(($CH_2)_p CH_3$)(($CH_2)_{p-1} CH_3$), wherein p is 4-8. In some embodiments, p is 5 and $L^5$ is a $C_1$-$C_3$ alkyl. In some embodiments, p is 6 and $L^5$ is a $C_3$ alkyl. In some embodiments, p is 7. In some embodiments, p is 8 and $L^5$ is a $C_1$-$C_3$ alkyl. In some embodiments, $R^5$ consists of —CH(($CH_2$)$_p$$CH_3$)(($CH_2$)$_{p-1}$$CH_3$), wherein p is 7 or 8.

In some embodiments, $R^4$ is ethylene or propylene. In some embodiments, $R^4$ is n-propylene or isobutylene.

In some embodiments, $L^7$ is absent, $R^4$ is ethylene, $X^7$ is S and $R^7$ and $R^8$ are each methyl. In some embodiments, $L^7$ is absent, $R^4$ is n-propylene, $X^7$ is S and $R^7$ and $R^8$ are each methyl. In some embodiments, $L^7$ is absent, $R^4$ is ethylene, $X^7$ is S and $R^7$ and $R^8$ are each ethyl.

In some embodiments, $X^7$ is S, $X^5$ is —C(O)O—, whereby —C(O)O—$R^6$ is formed, $X^6$ is —C(O)O— whereby —C(O)O—$R^5$ is formed, $L^5$ and $L^6$ are each independently a linear $C_3$-$C_7$ alkyl, $L^7$ is absent, $R^5$ is —CH(($CH_2$)$_p$$CH_3$)$_2$, and $R^6$ is $C_7$-$C_{12}$ alkenyl. In some further embodiments, p is 6 and $R^6$ is $C_9$ alkenyl.

In some embodiments, the lipid formulation and methods of producing the same comprises an ionizable cationic lipid selected from the group consisting of

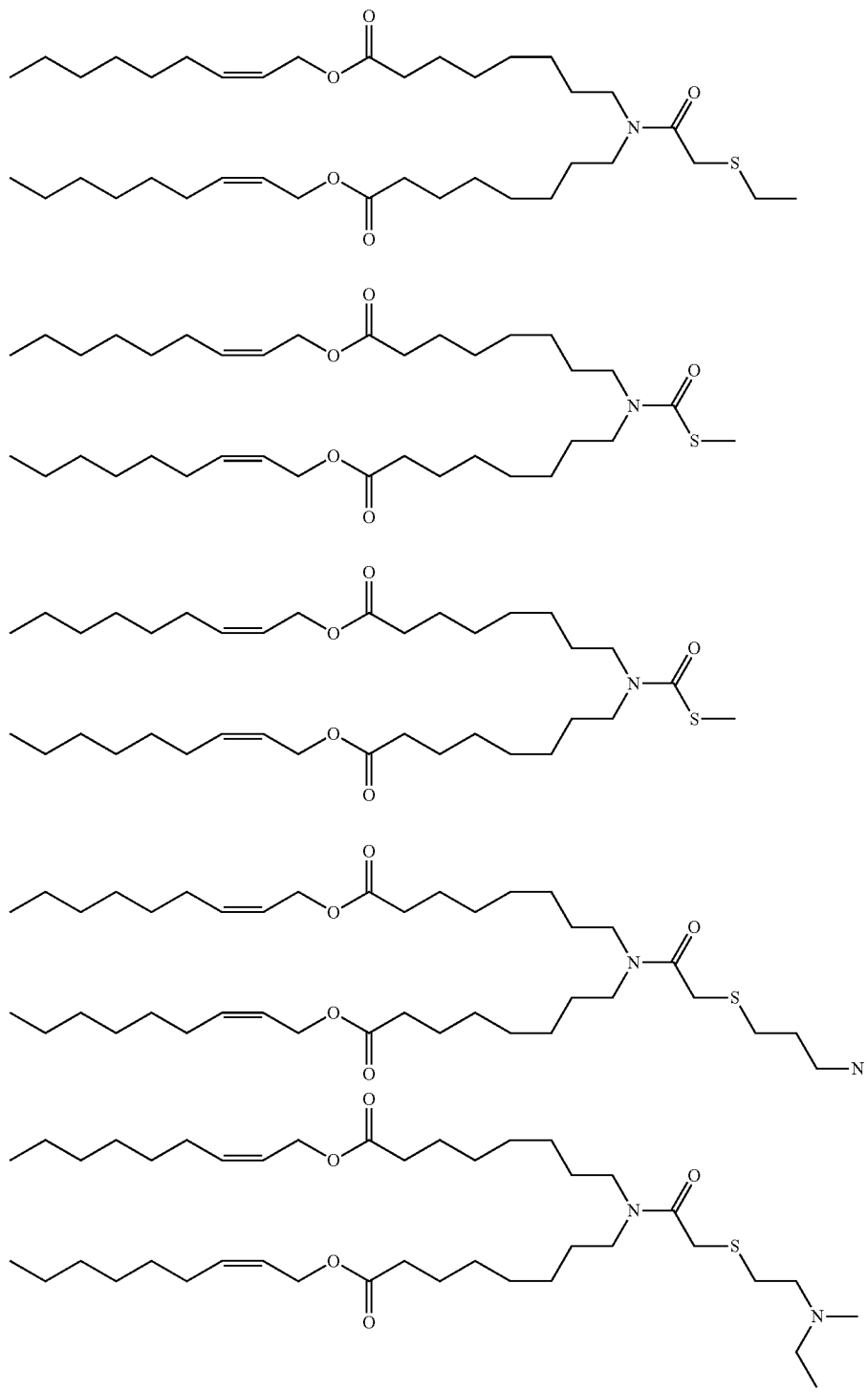

-continued
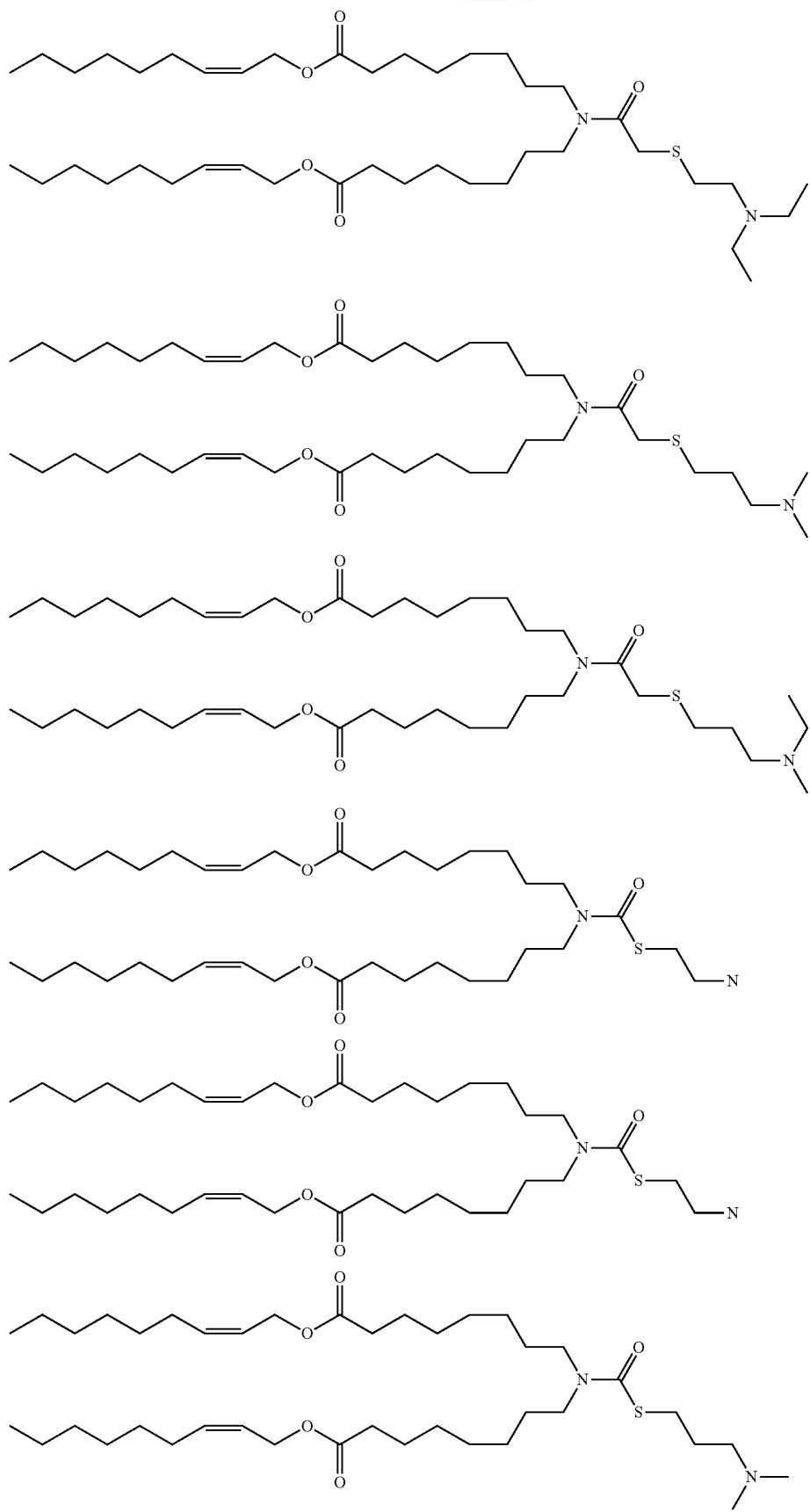

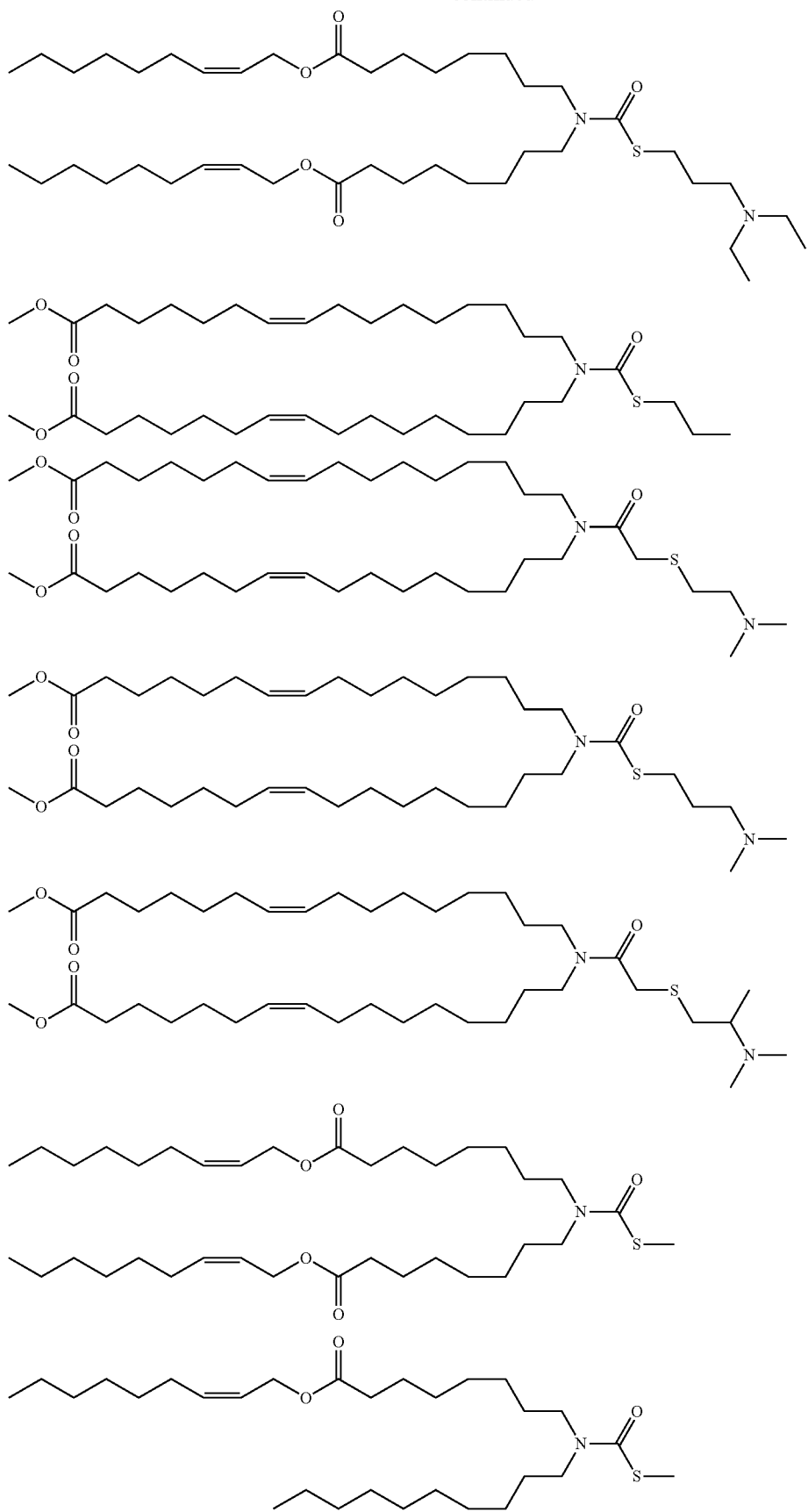

-continued
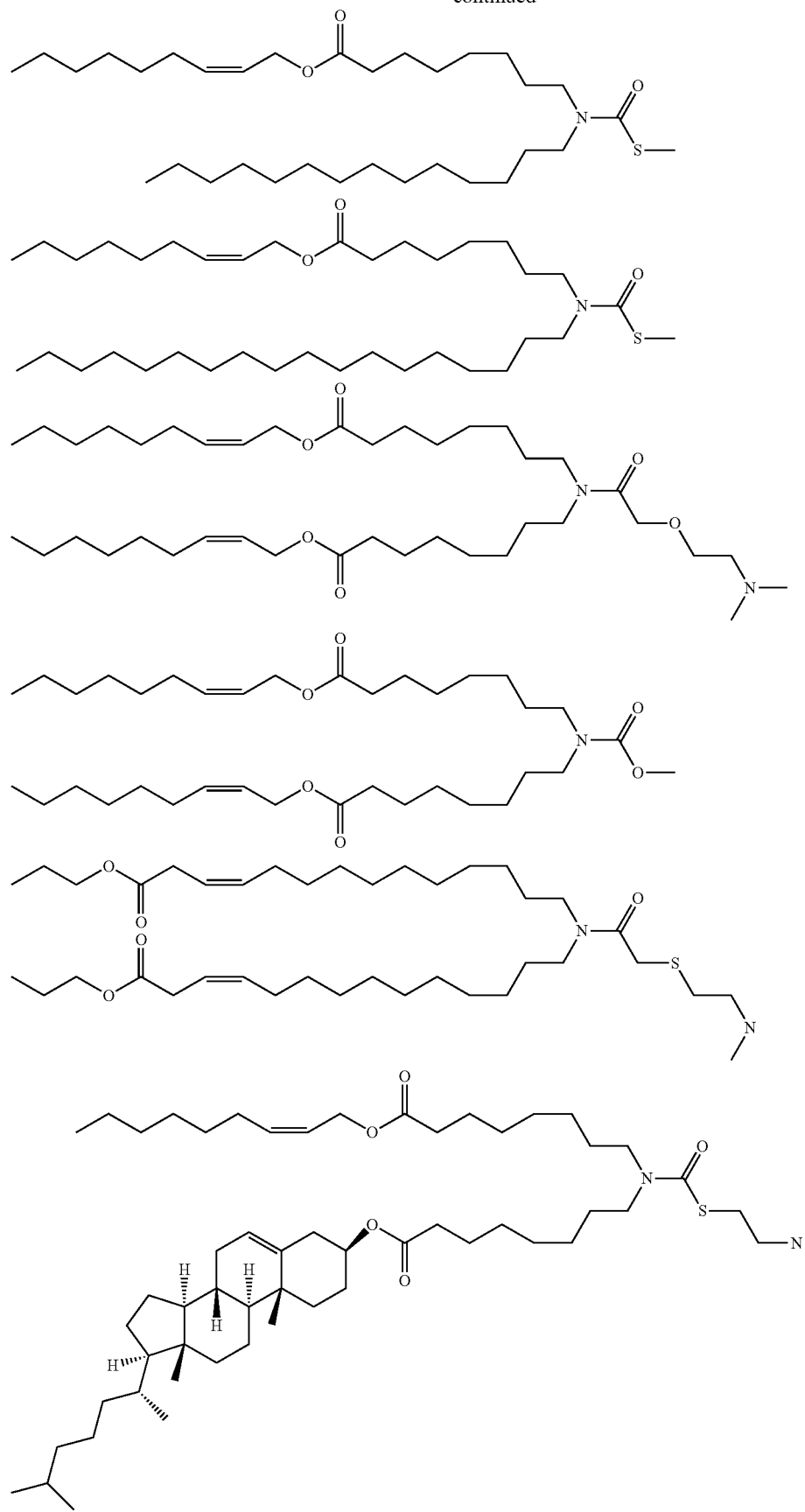

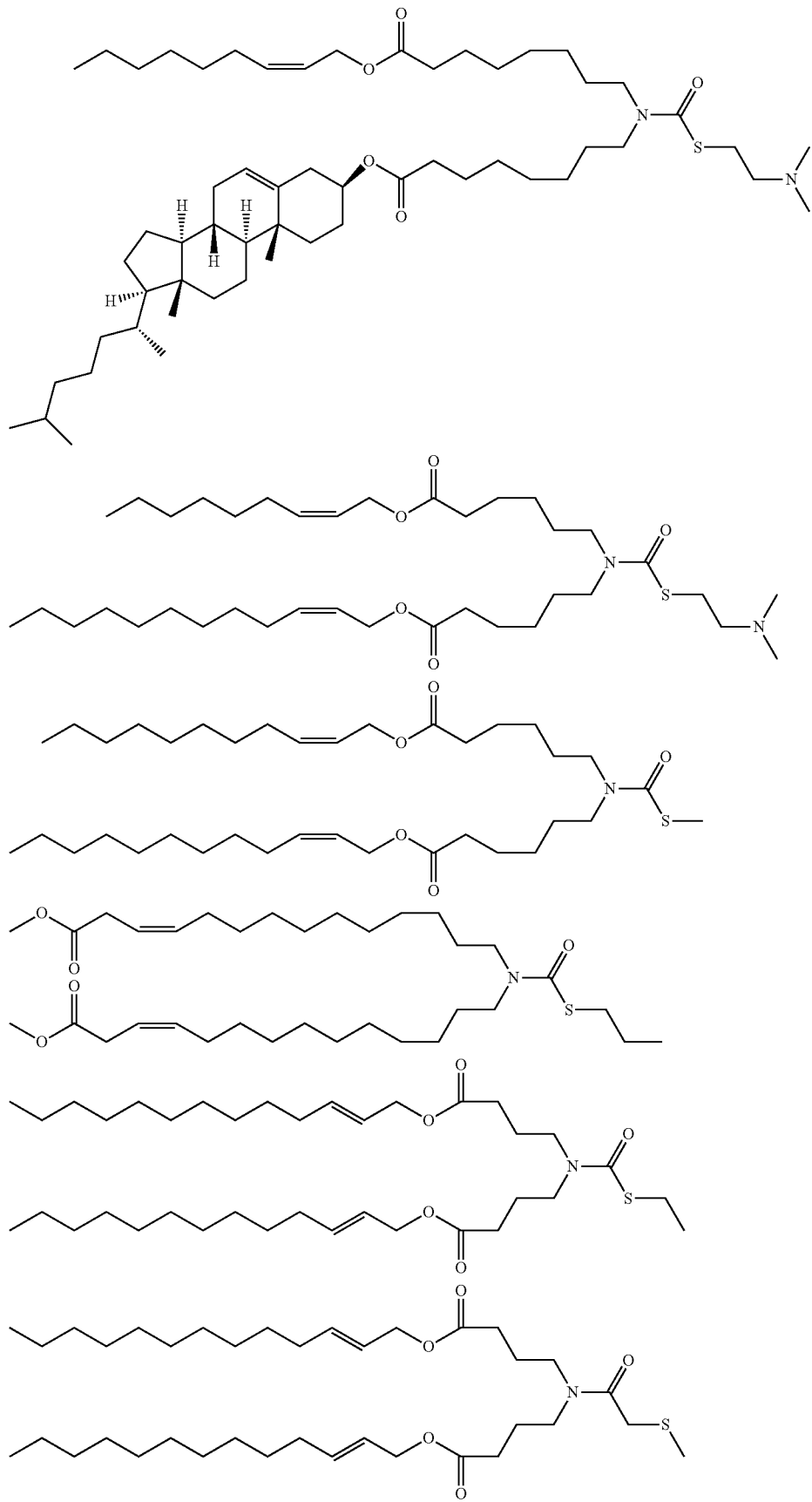

-continued
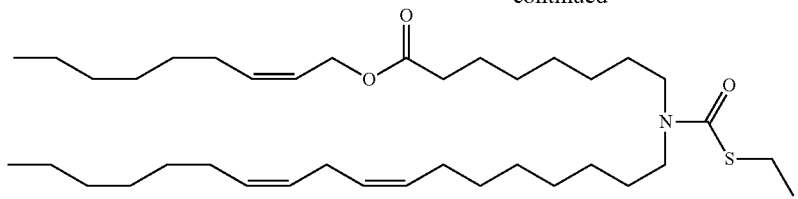
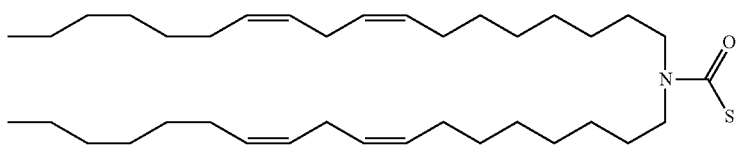
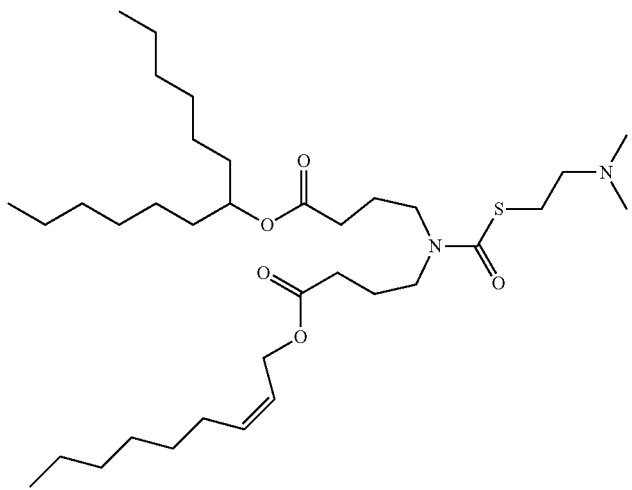
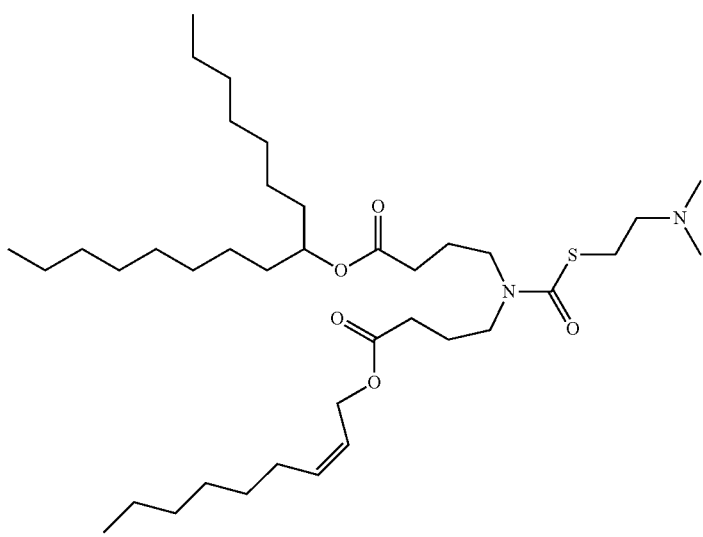

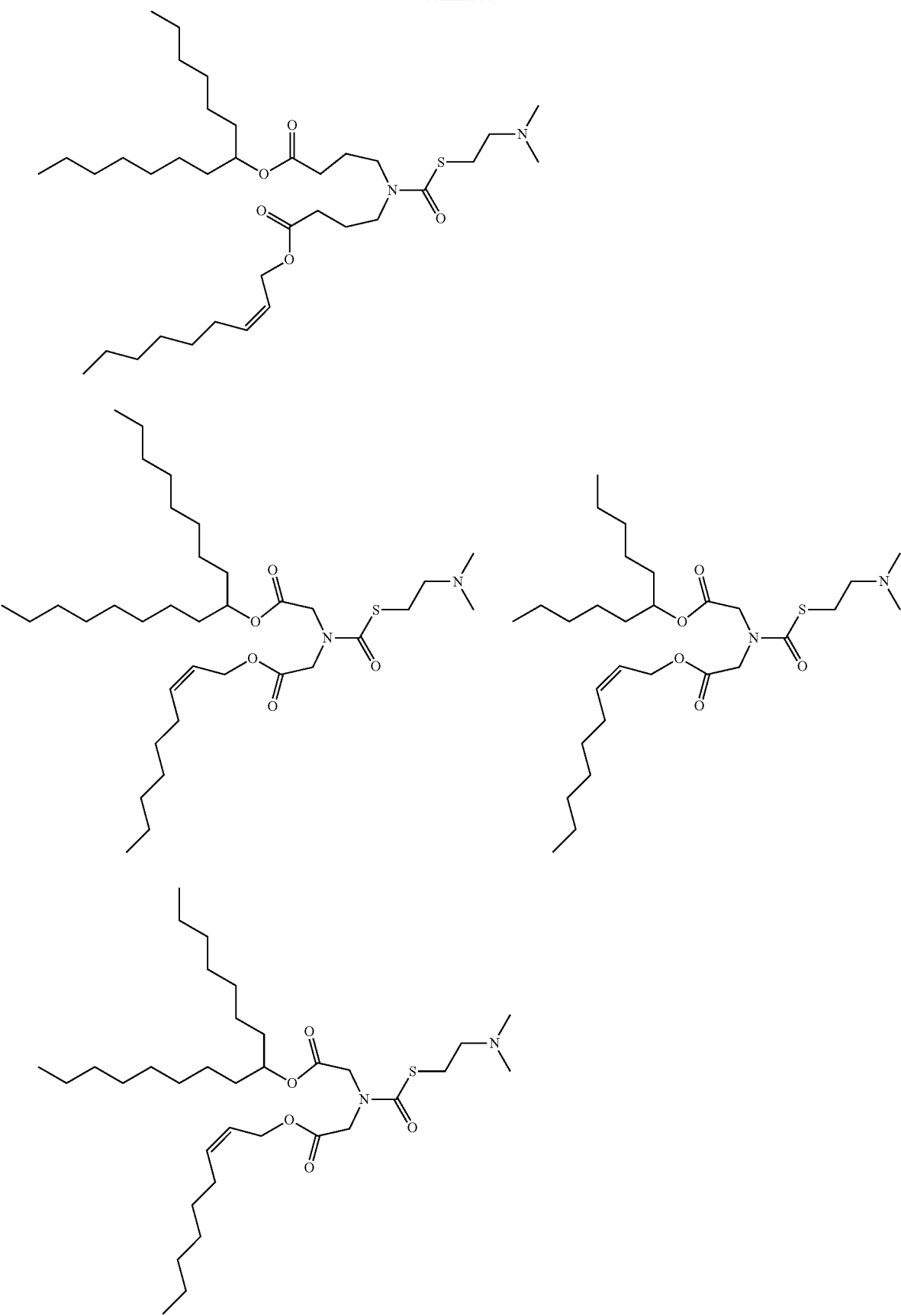

-continued
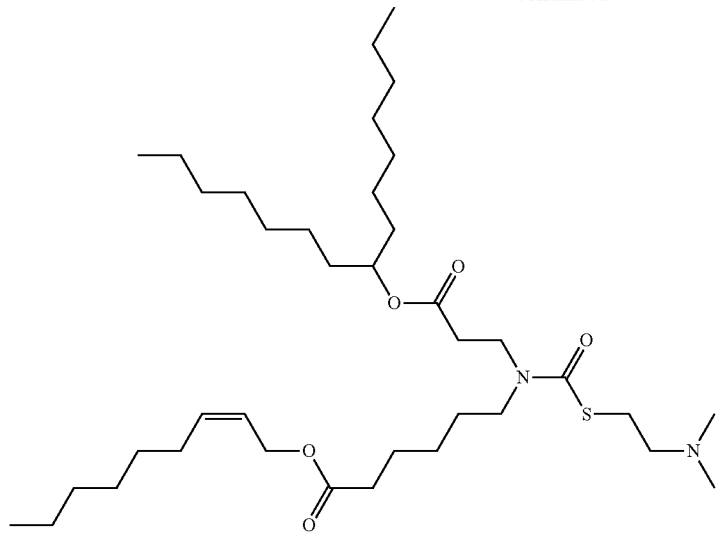
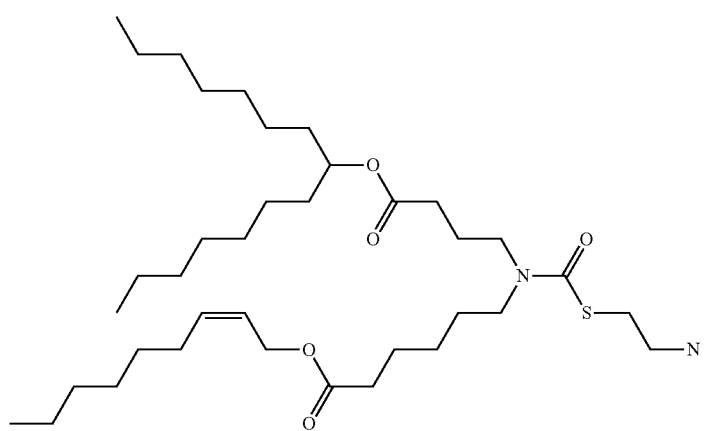
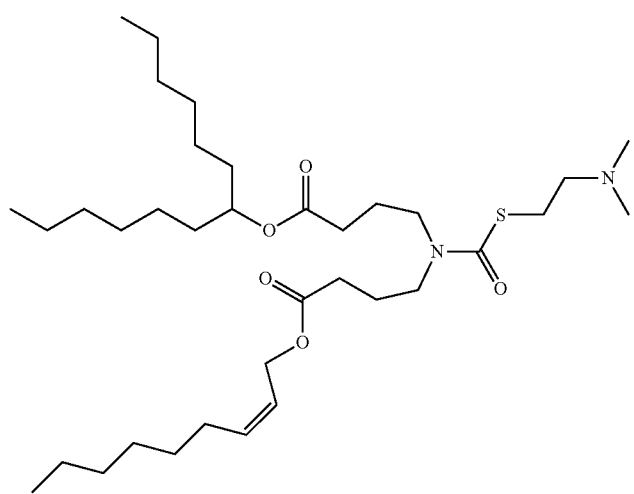

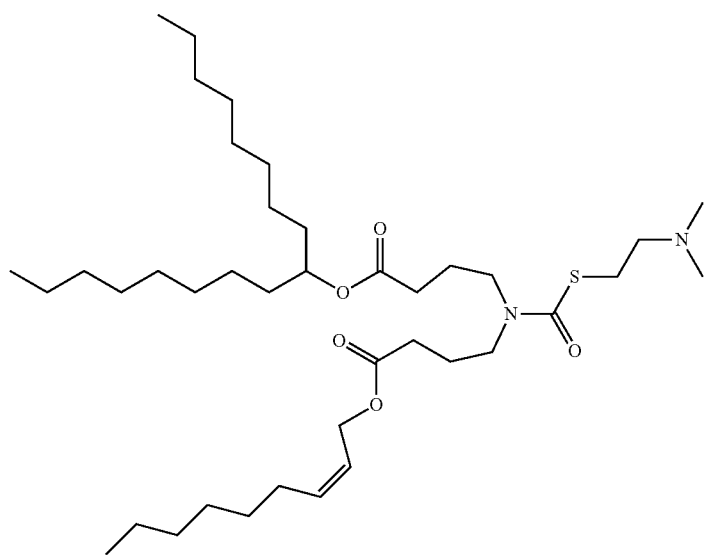
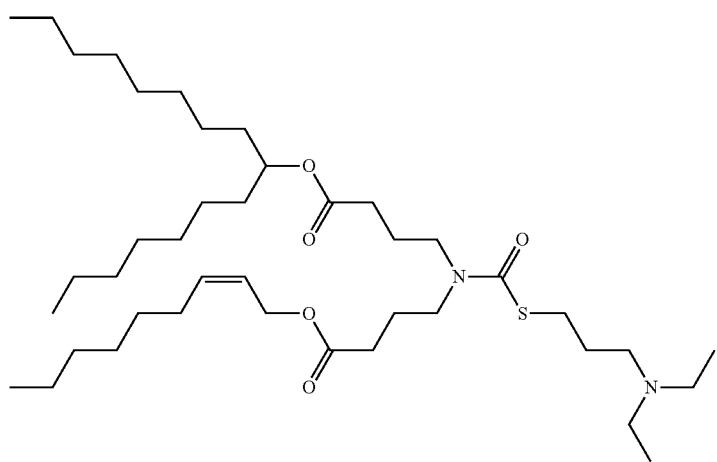
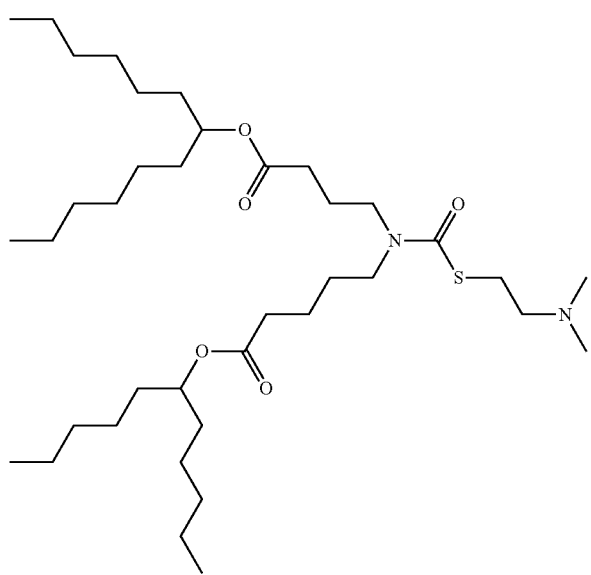

-continued
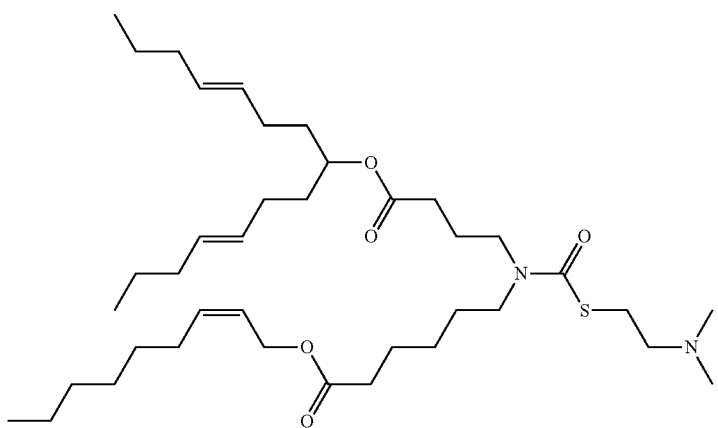
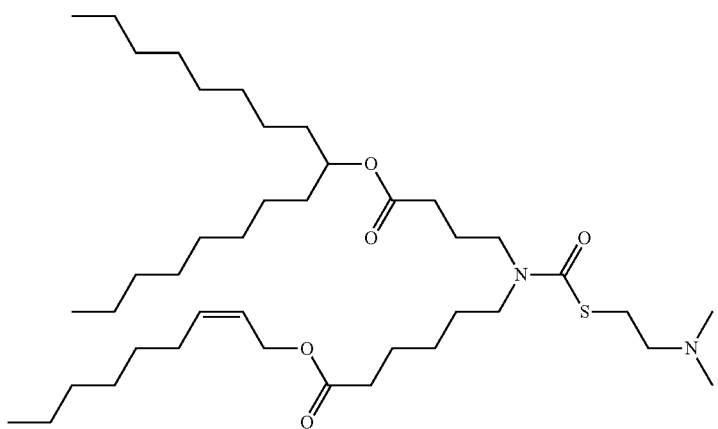
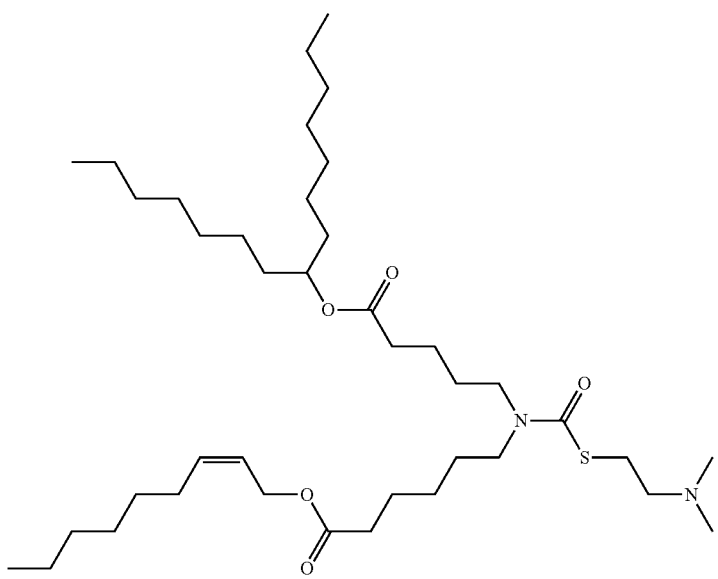

-continued
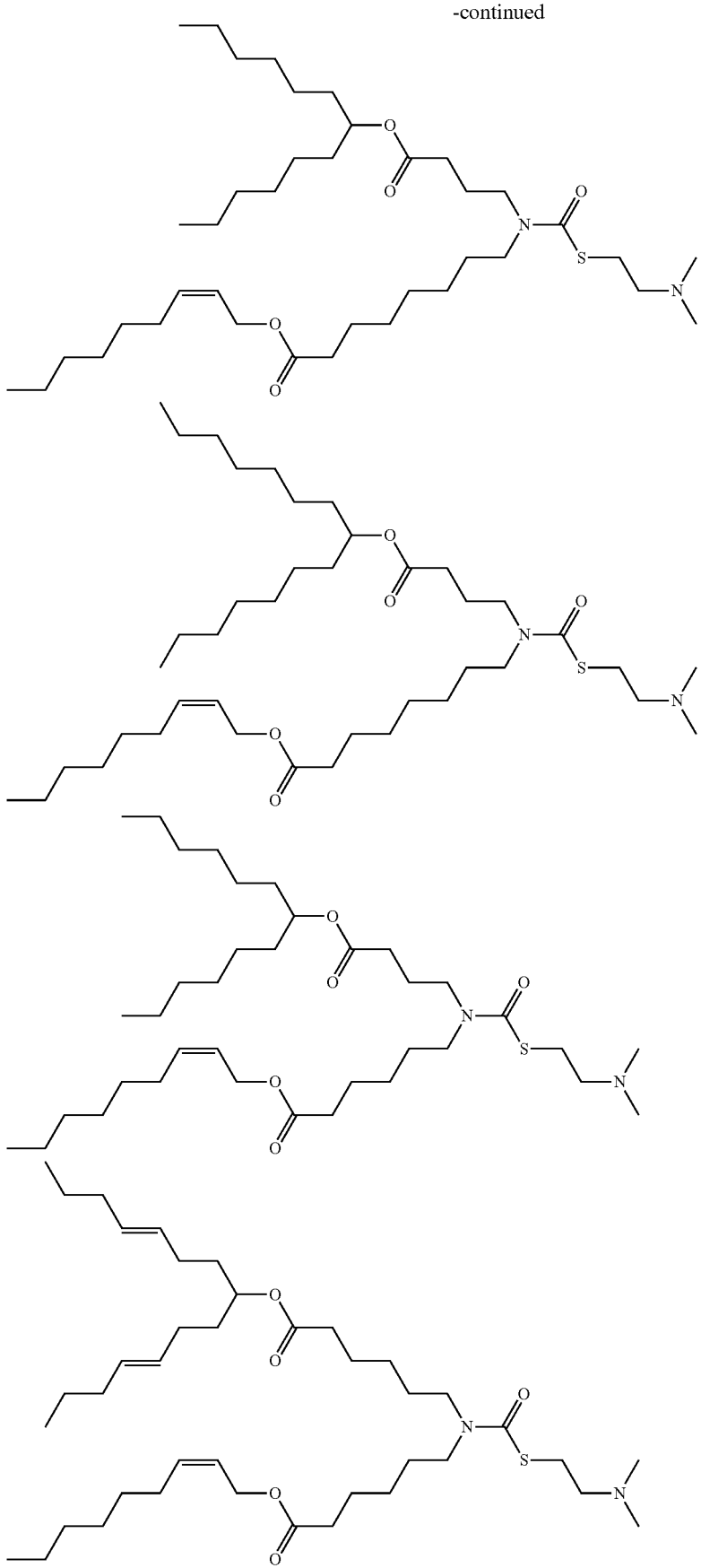

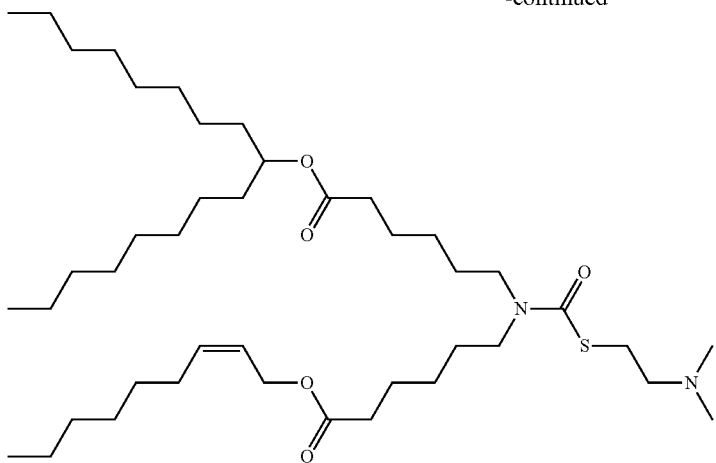
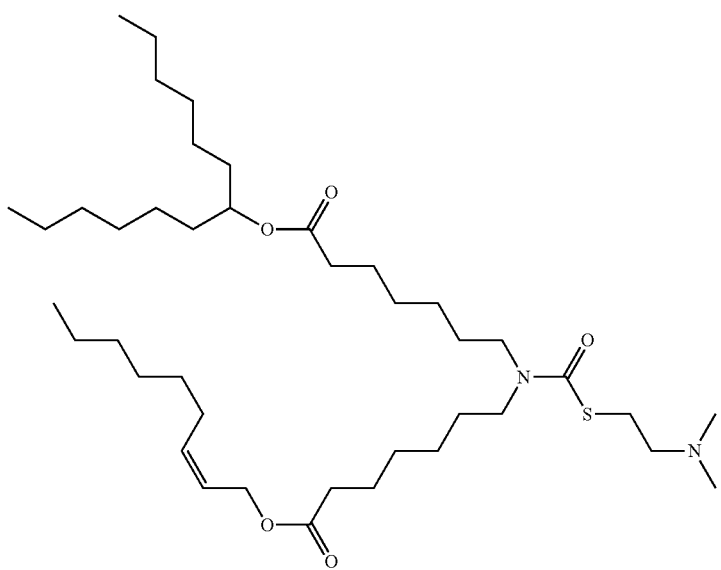
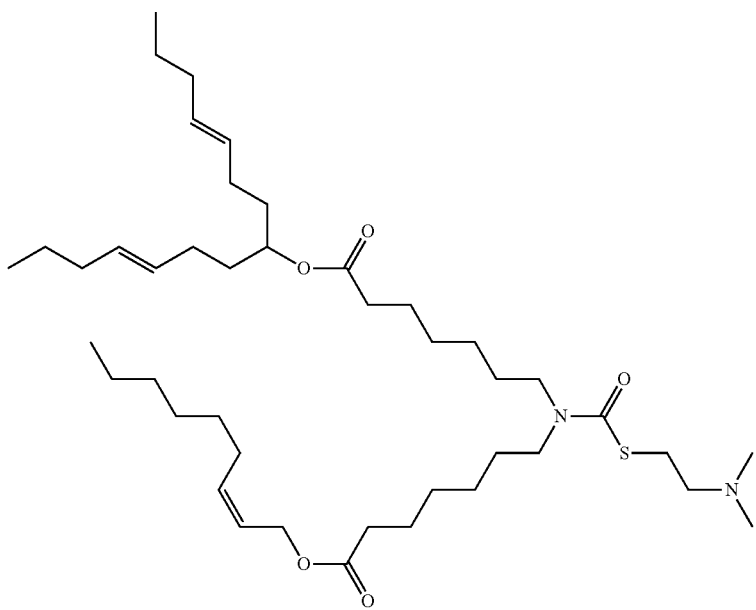

-continued
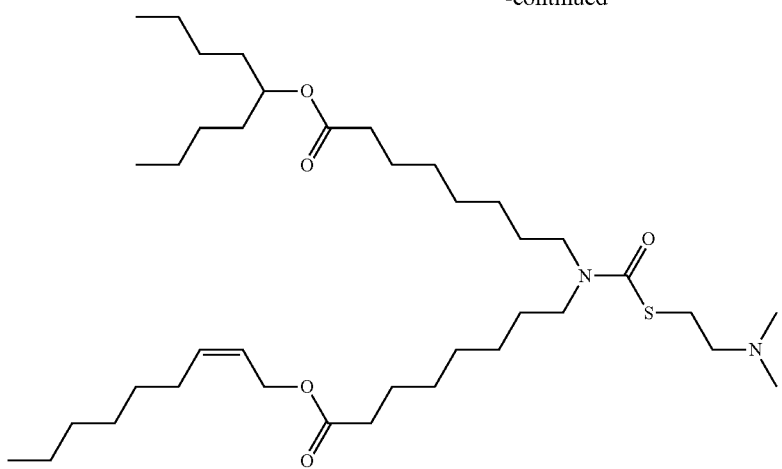
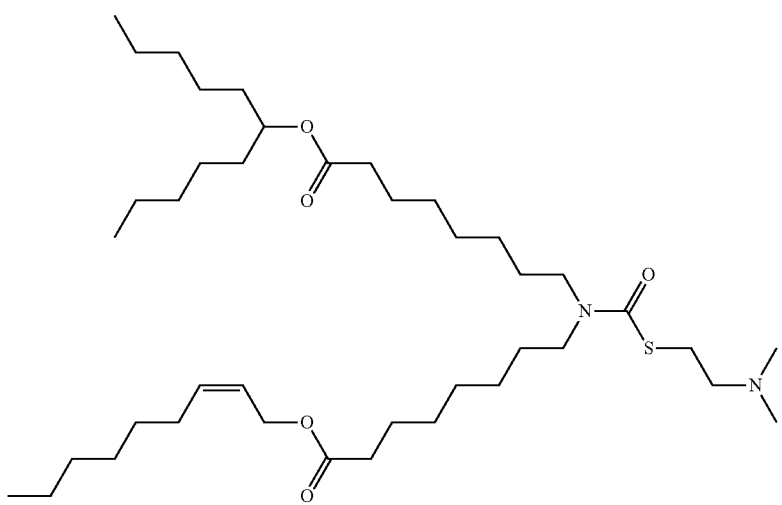
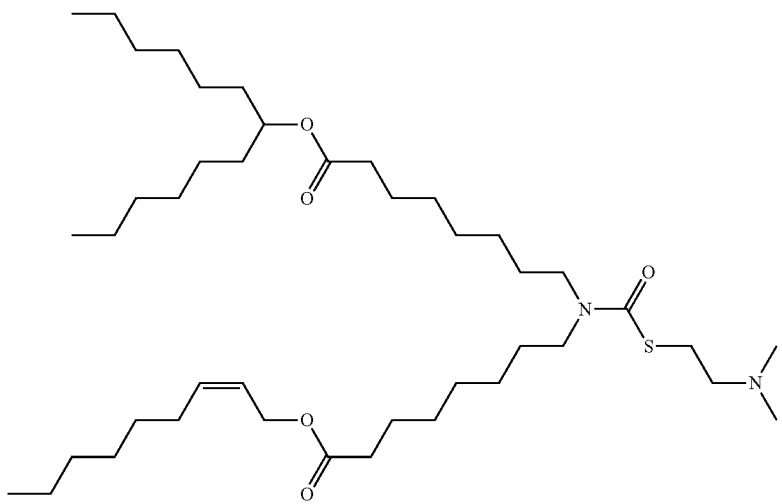

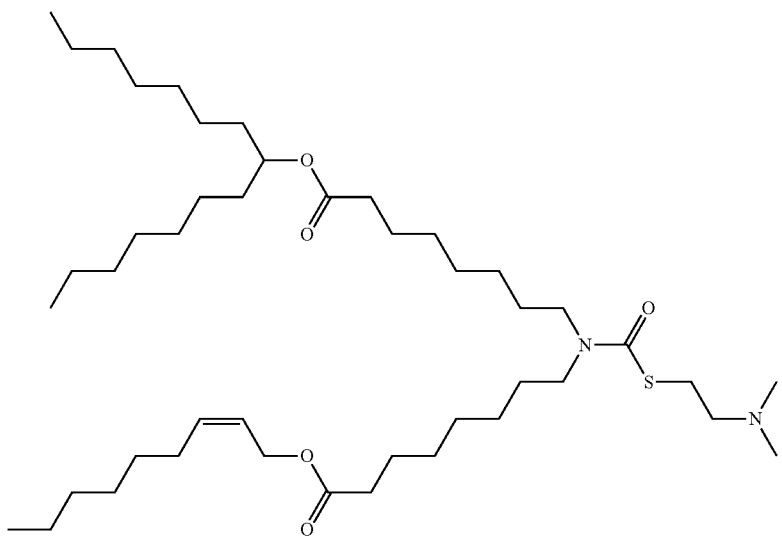
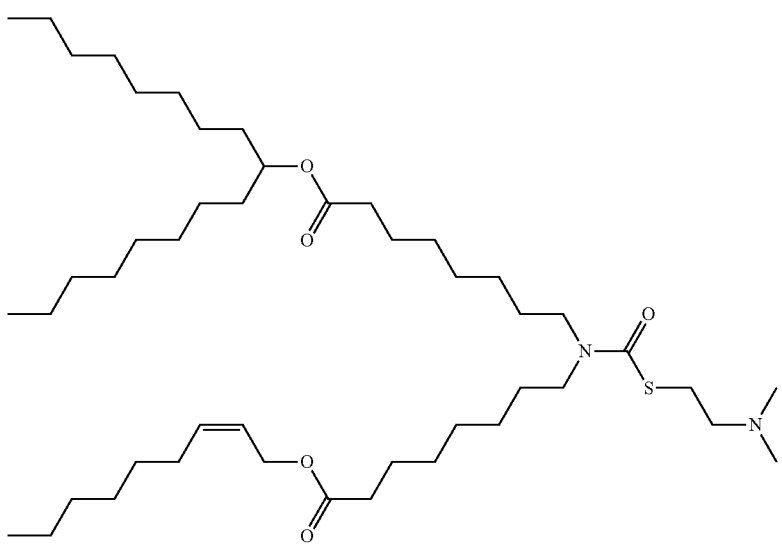
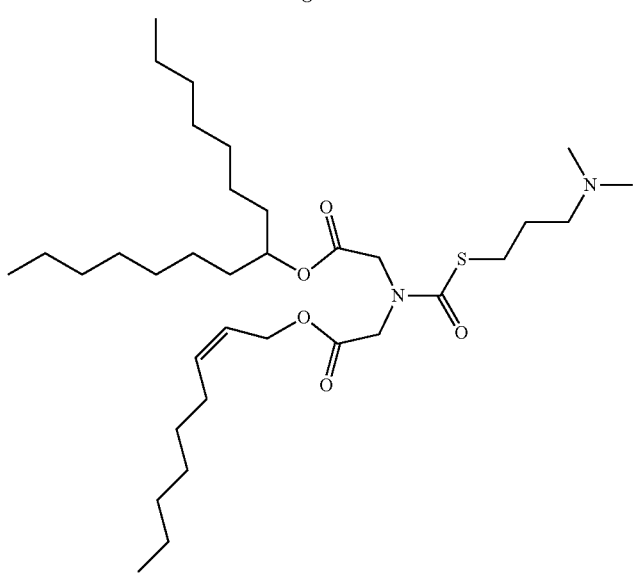

-continued
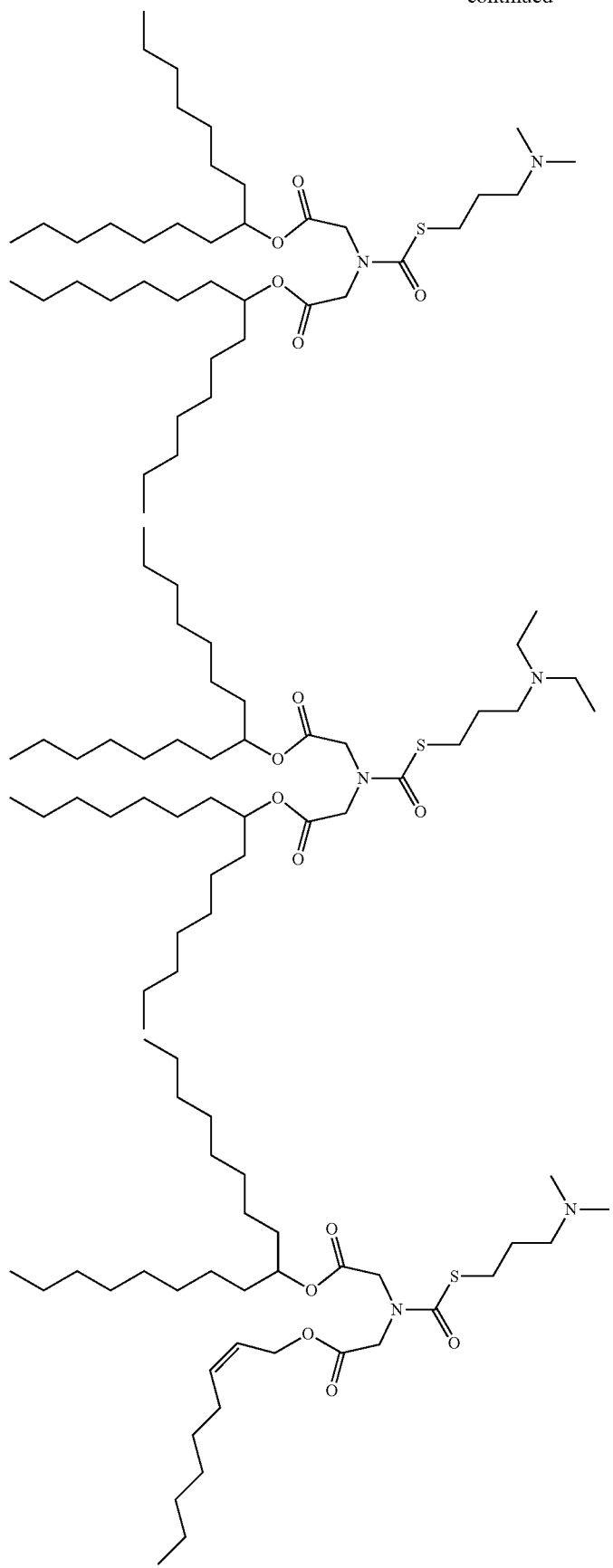

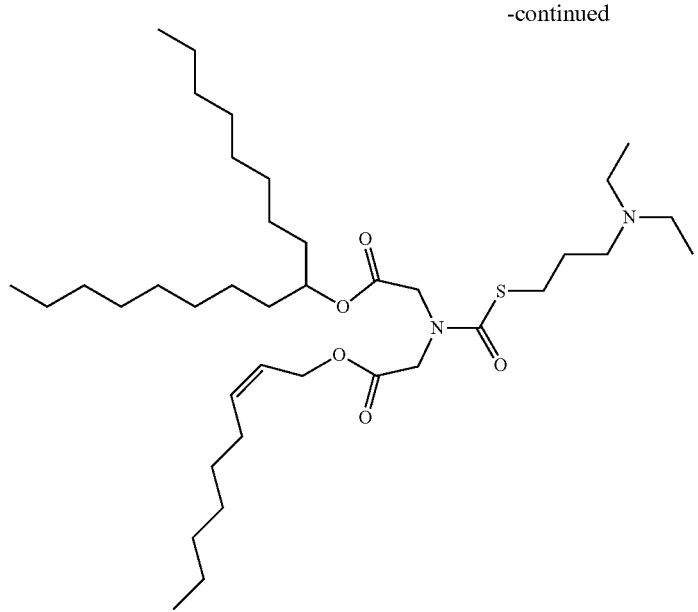
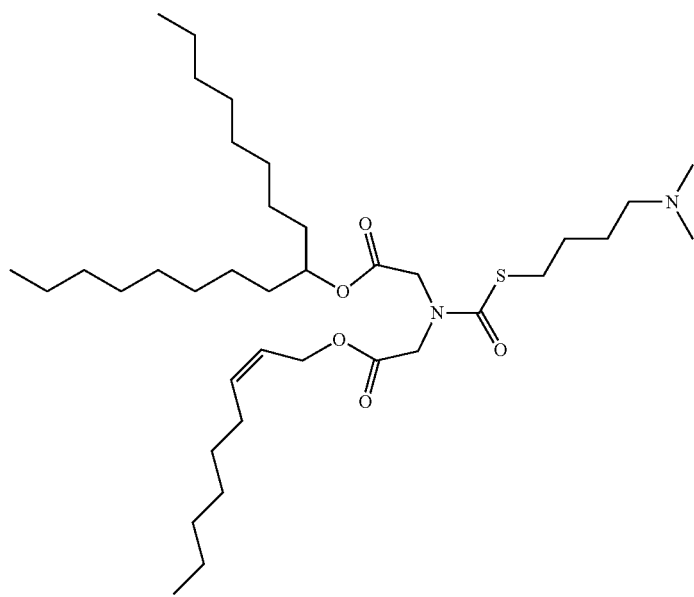

-continued
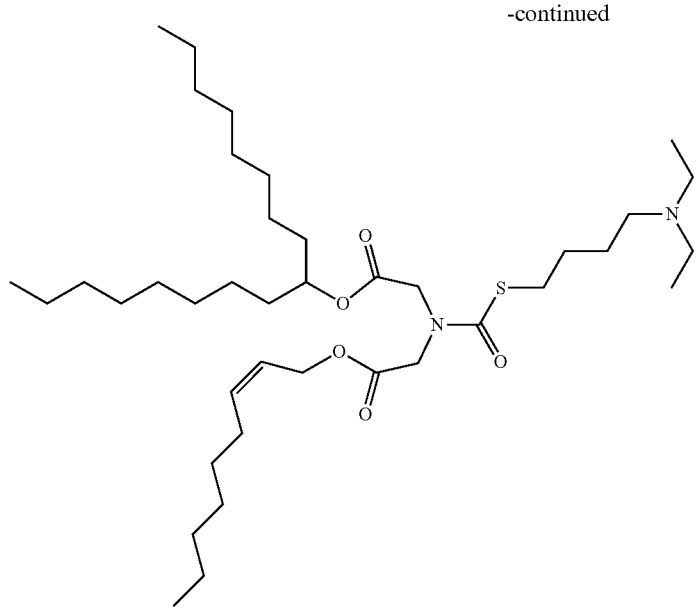
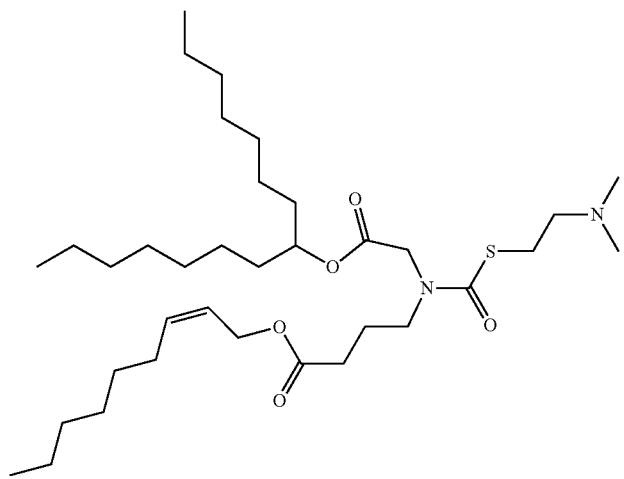
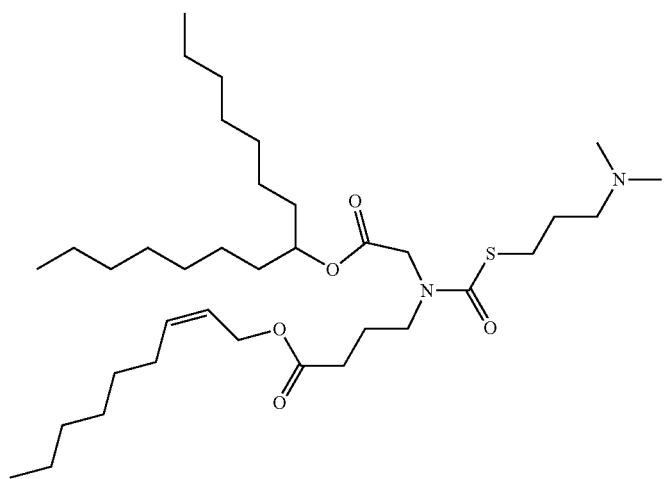

-continued
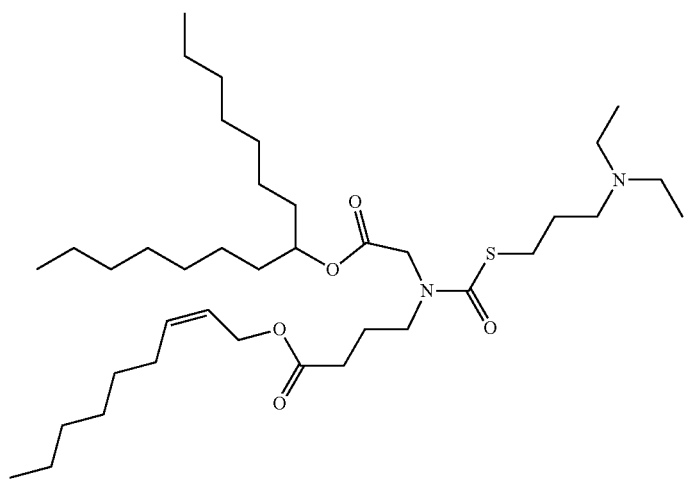
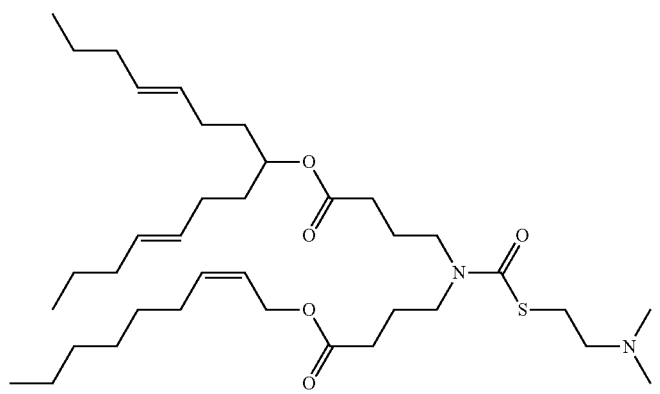
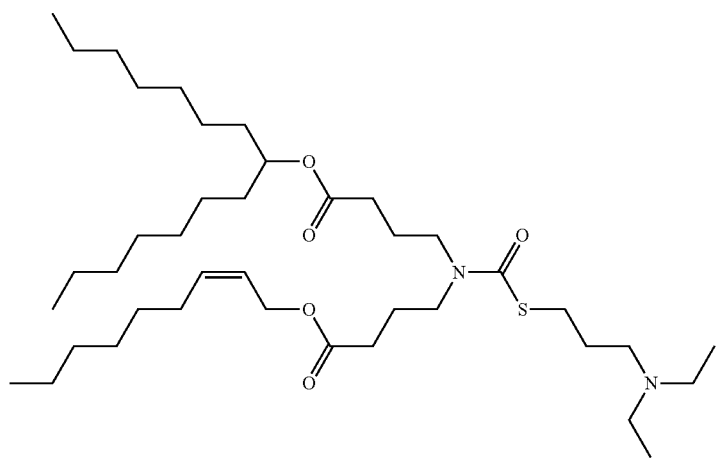

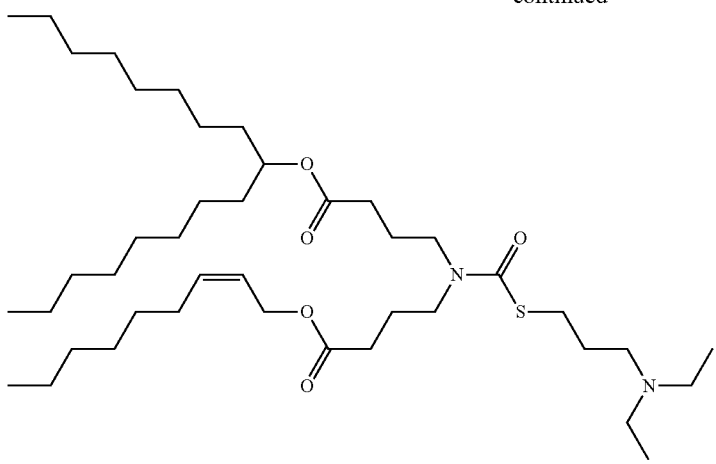
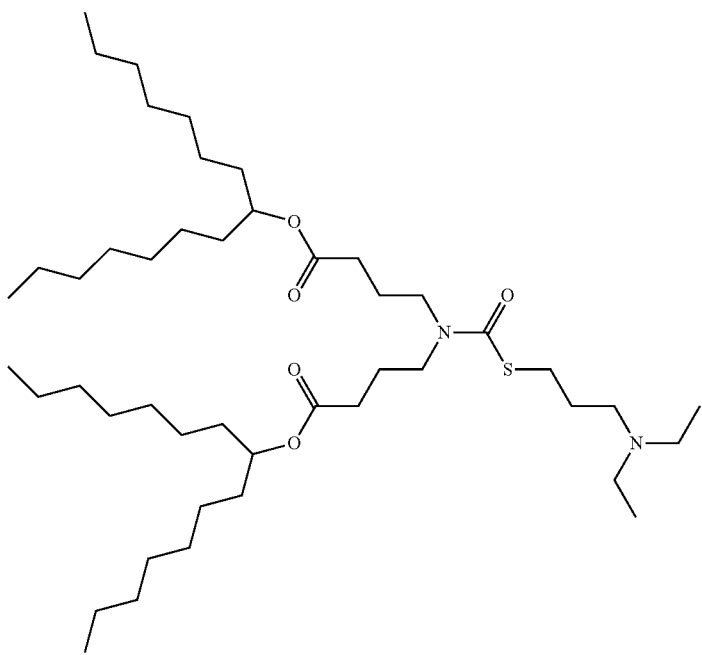
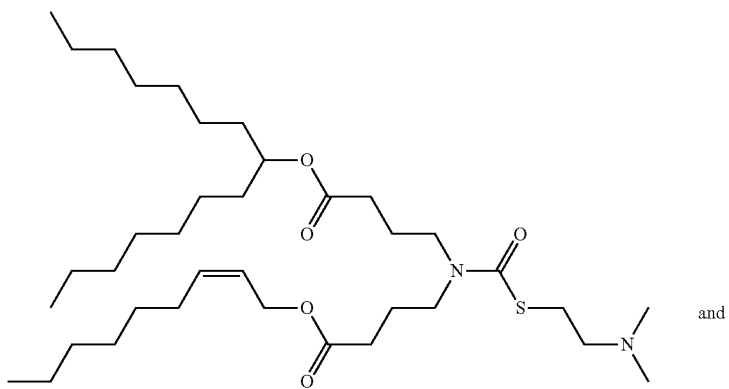 and

-continued
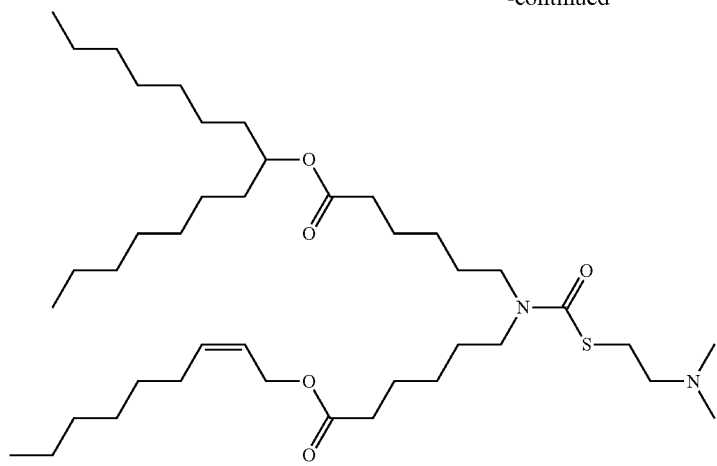
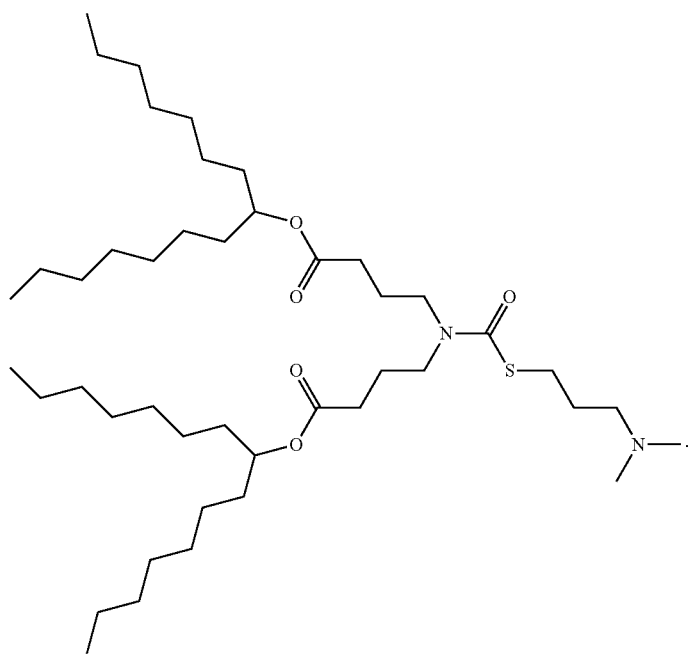
In some embodiments, the lipid formulation can comprise an ionizable cationic lipid selected from the group consisting of LIPID #1 to LIPID #9 as shown below in Table 1:
TABLE 1
| LIPID # | STRUCTURE |
|---|---|
| 1 | 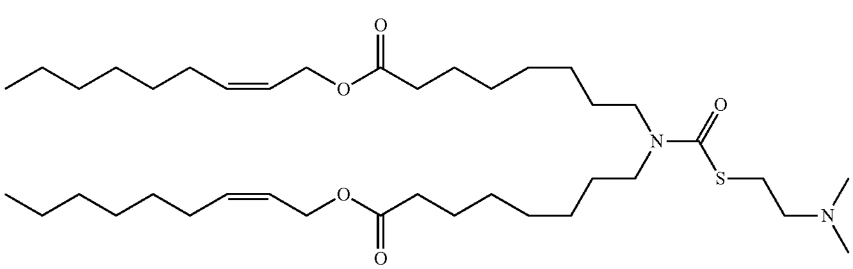 [SMILES: CCCCCC/C=C\COC(=O)CCCCCCCN(CCCCCCCC(=O)OC/C=C\CCCCCC)C(=O)SCCN(C)C] |

TABLE 1-continued
| LIPID # | STRUCTURE |
|---|---|
| 2 | 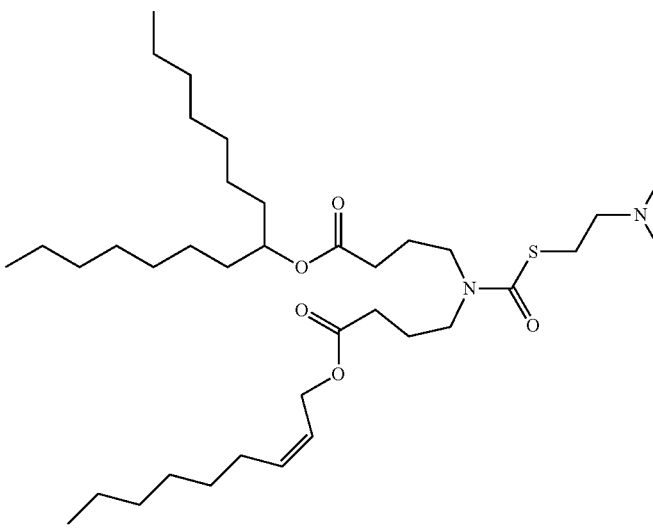 |
| 3 | 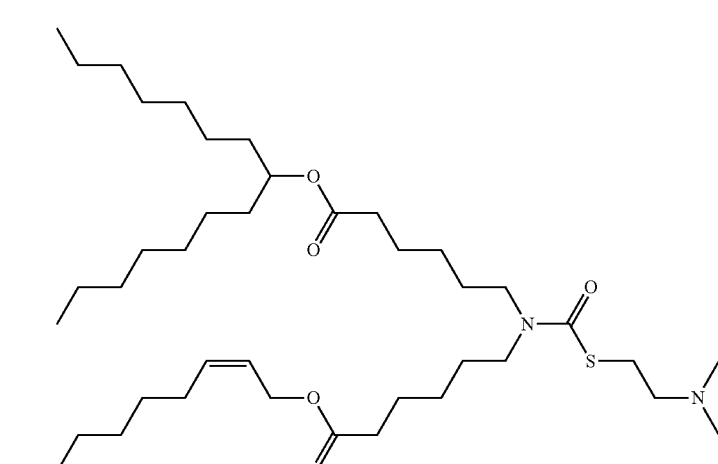 |
| 4 | 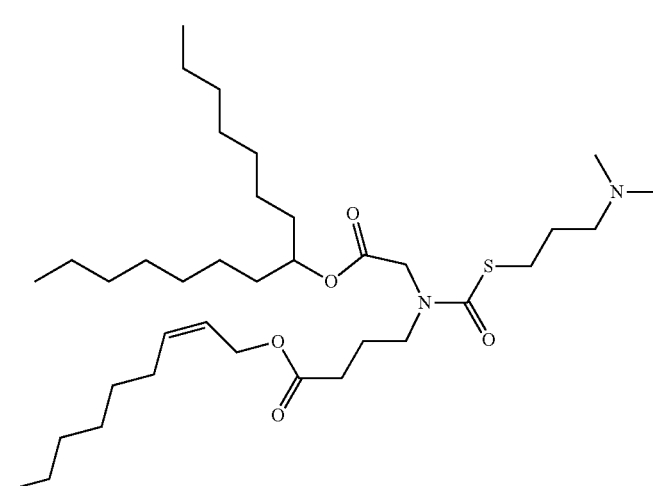 |

TABLE 1-continued
| LIPID # | STRUCTURE |
|---|---|
| 5 | 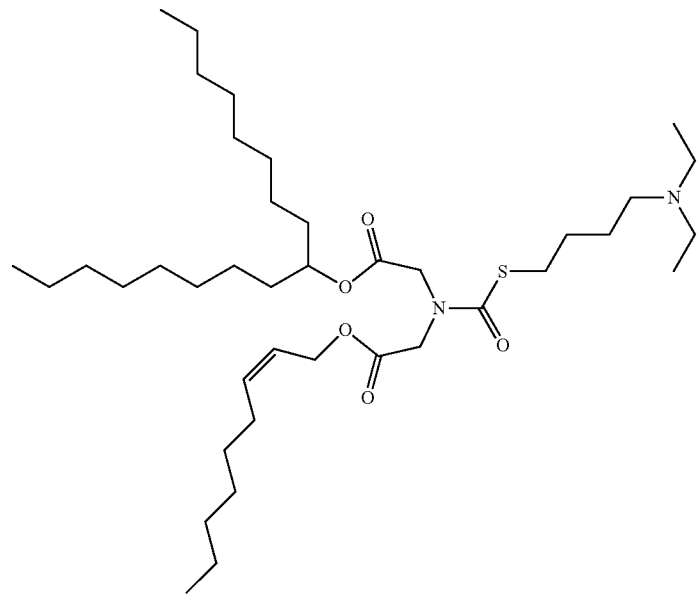 [SMILES: CCCCCC/C=C\COC(=O)CN(CC(=O)OC(CCCCCCCC)CCCCCCCC)C(=O)SCCCCN(CC)CC] |
| 6 | 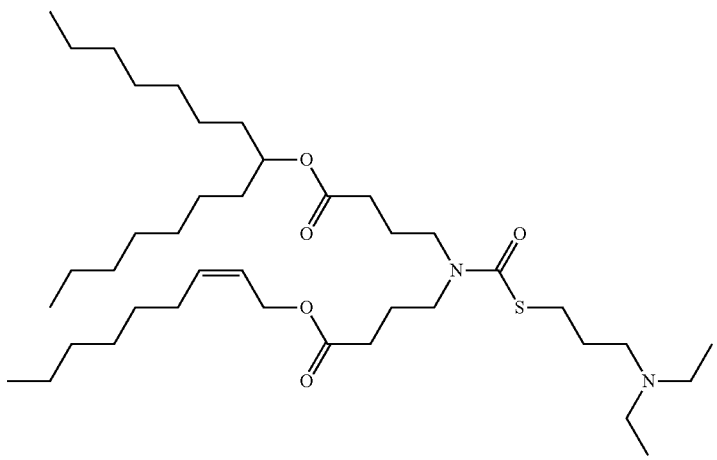 [SMILES: CCCCCC/C=C\COC(=O)CCCN(CCCC(=O)OC(CCCCCCC)CCCCCCC)C(=O)SCCCN(CC)CC] |

TABLE 1-continued
| LIPID # | STRUCTURE |
|---------|-----------|
| 7 | 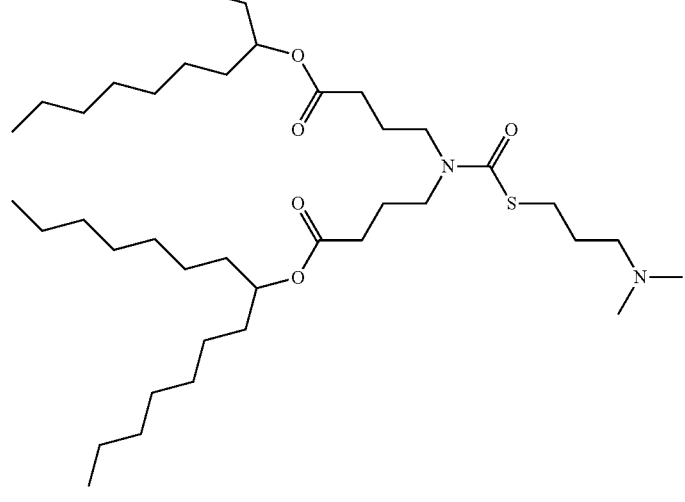 |
| 8 | 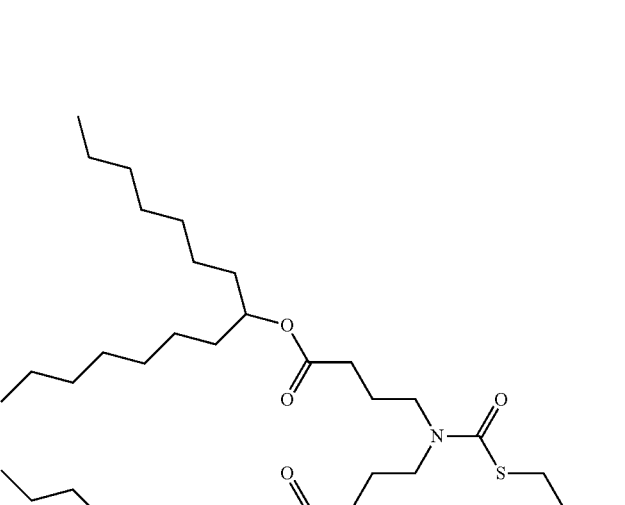 |

TABLE 1-continued
| LIPID # | STRUCTURE |
|---|---|
| 9 | 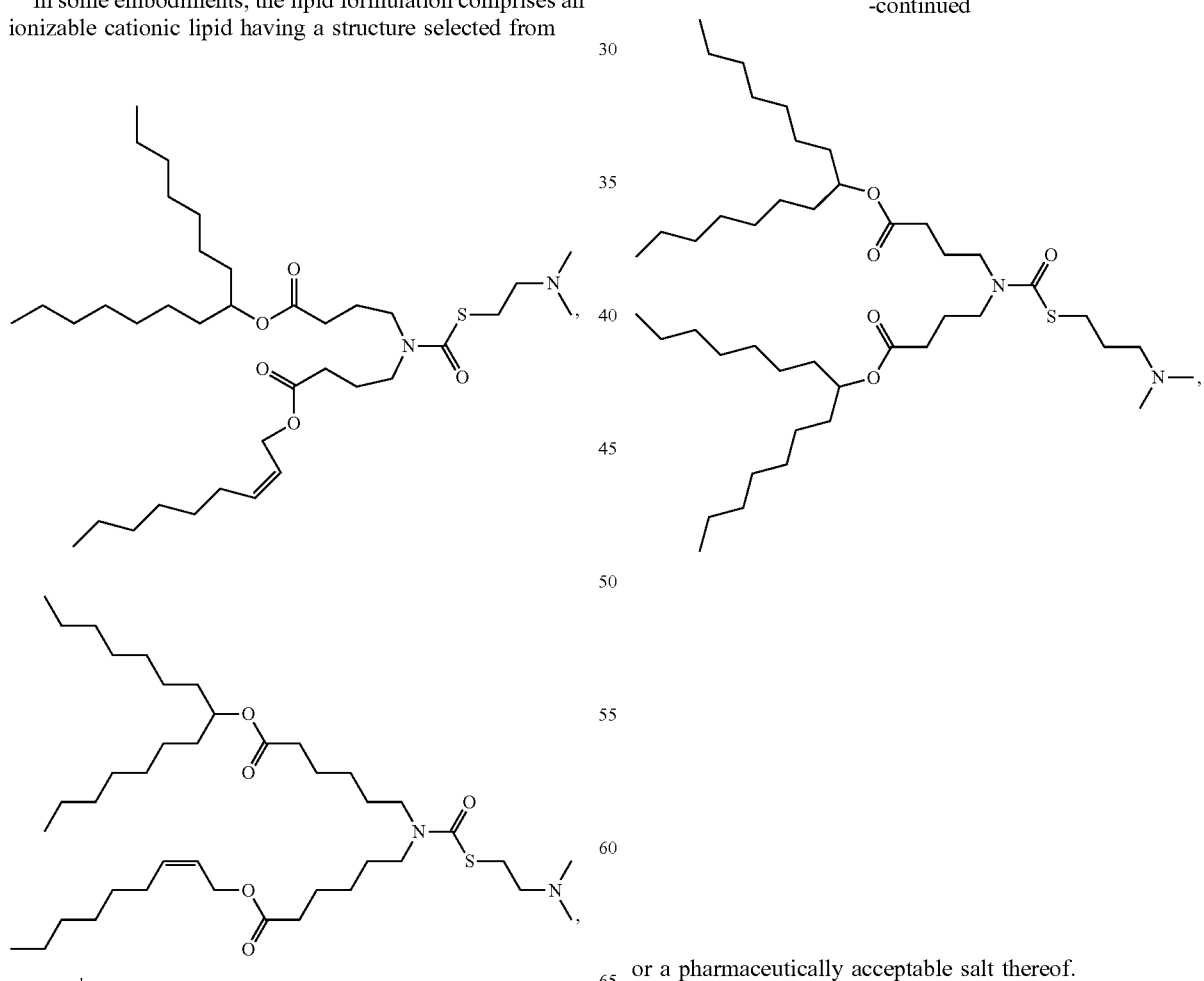 |
In some embodiments, the lipid formulation comprises an ionizable cationic lipid having a structure selected from
and
or a pharmaceutically acceptable salt thereof.
In some preferred embodiments, the lipid formulation comprises an ionizable cationic lipid having the structure

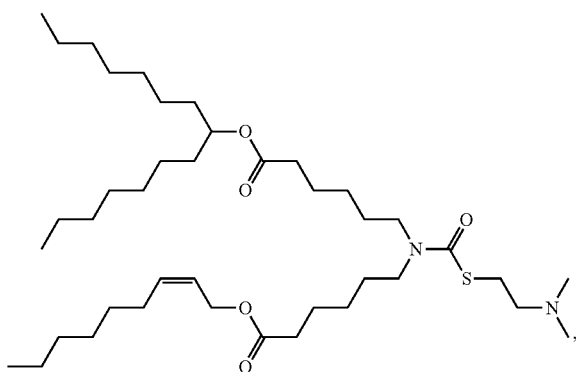

or a pharmaceutically acceptable salt thereof.

In embodiments, any one or more lipids recited herein may be expressly excluded.

Helper Lipids and Sterols

The mRNA-lipid formulations of the present disclosure and methods of producing the same can comprise a helper lipid, which can be referred to as a neutral helper lipid, non-cationic lipid, non-cationic helper lipid, anionic lipid, anionic helper lipid, or a neutral lipid. It has been found that lipid formulations, particularly cationic liposomes and lipid nanoparticles have increased cellular uptake if helper lipids are present in the formulation. (Curr. Drug Metab. 2014; 15(9):882-92). For example, some studies have indicated that neutral and zwitterionic lipids such as 1,2-dioleoylsn-glycero-3-phosphatidylcholine (DOPC), Di-Oleoyl-Phosphatidyl-Ethanoalamine (DOPE) and 1,2-DiStearoyl-sn-glycero-3-PhosphoCholine (DSPC), being more fusogenic (i.e., facilitating fusion) than cationic lipids, can affect the polymorphic features of lipid-nucleic acid complexes, promoting the transition from a lamellar to a hexagonal phase, and thus inducing fusion and a disruption of the cellular membrane. (Nanomedicine (Lond). 2014 January; 9(1):105-20). In addition, the use of helper lipids can help to reduce any potential detrimental effects from using many prevalent cationic lipids such as toxicity and immunogenicity.

Non-limiting examples of non-cationic lipids suitable for lipid formulations of the present disclosure and methods of producing the same include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, palmitoyl, stearoyl, or oleoyl.

Additional examples of non-cationic lipids include sterols such as cholesterol and derivatives thereof. One study concluded that as a helper lipid, cholesterol increases the spacing of the charges of the lipid layer interfacing with the nucleic acid making the charge distribution match that of the nucleic acid more closely. (J. R. Soc. Interface. 2012 Mar. 7; 9(68): 548-561). Non-limiting examples of cholesterol derivatives include polar analogues such as 5α-cholestanol, 5α-coprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5α-cholestanone, and cholesteryl decanoate; and mixtures thereof. In preferred embodiments, the cholesterol derivative is a polar analogue such as cholesteryl-(4'-hydroxy)-butyl ether.

In some embodiments, the helper lipid present in the lipid formulation comprises or consists of a mixture of one or more phospholipids and cholesterol or a derivative thereof. In other embodiments, the neutral lipid present in the lipid formulation comprises or consists of one or more phospholipids, e.g., a cholesterol-free lipid formulation. In yet other embodiments, the neutral lipid present in the lipid formulation comprises or consists of cholesterol or a derivative thereof, e.g., a phospholipid-free lipid formulation.

Other examples of helper lipids include nonphosphorous containing lipids such as, e.g., stearylamine, dodecylamine, hexadecylamine, acetyl palmitate, glycerol ricinoleate, hexadecyl stearate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, and sphingomyelin.

In some embodiments, the helper lipid comprises from about 2 mol % to about 20 mol %, from about 3 mol % to about 18 mol %, from about 4 mol % to about 16 mol %, about 5 mol % to about 14 mol %, from about 6 mol % to about 12 mol %, from about 5 mol % to about 10 mol %, from about 5 mol % to about 9 mol %, or about 2 mol %, about 3 mol %, about 4 mol %, about 5 mol %, about 6 mol %, about 7 mol %, about 8 mol %, about 9 mol %, about 10 mol %, about 11 mol %, or about 12 mol % (or any fraction thereof or the range therein) of the total lipid present in the lipid formulation.

The cholesterol or cholesterol derivative in the lipid formulation and methods of producing the same may comprise up to about 40 mol %, about 45 mol %, about 50 mol %, about 55 mol %, or about 60 mol % of the total lipid present in the lipid formulation. In some embodiments, the cholesterol or cholesterol derivative comprises about 15 mol % to about 45 mol %, about 20 mol % to about 40 mol %, about 25 mol % to about 35 mol %, or about 28 mol % to about 35 mol %; or about 25 mol %, about 26 mol %, about 27 mol %, about 28 mol %, about 29 mol %, about 30 mol %, about 31 mol %, about 32 mol %, about 33 mol %, about 34 mol %, about 35 mol %, about 36 mol %, or about 37 mol % of the total lipid present in the lipid formulation.

In some embodiments, the phospholipid component in the mixture may comprise from about 2 mol % to about 20 mol %, from about 3 mol % to about 18 mol %, from about 4 mol % to about 16 mol %, about 5 mol % to about 14 mol %, from about 6 mol % to about 12 mol %, from about 5 mol % to about 10 mol %, from about 5 mol % to about 9 mol %, or about 2 mol %, about 3 mol %, about 4 mol %, about 5 mol %, about 6 mol %, about 7 mol %, about 8 mol %, about 9 mol %, about 10 mol %, about 11 mol %, or about 12 mol % (or any fraction thereof or the range therein) of the total lipid present in the lipid formulation.

The percentage of helper lipid present in the lipid formulation and methods of producing the same is a target amount, and the actual amount of helper lipid present in the formulation may vary, for example, by +5 mol %.

A lipid formulation containing a cationic lipid compound or ionizable cationic lipid compound may be on a molar basis about 30-70% cationic lipid compound, about 25-40% cholesterol, about 2-15% helper lipid, and about 0.5-5% of a polyethylene glycol (PEG) lipid, wherein the percent is of the total lipid present in the formulation. In some embodiments, the composition is about 40-65% cationic lipid compound, about 25-35% cholesterol, about 3-9% helper lipid, and about 0.5-3% of a PEG-lipid, wherein the percent is of the total lipid present in the formulation.

The formulation may be a lipid particle formulation, for example containing 8-30% nucleic acid compound, 5-30% helper lipid, and 0-20% cholesterol; 4-25% cationic lipid, 4-25% helper lipid, 2-25% cholesterol, 10-35% cholesterol-PEG, and 5% cholesterol-amine; or 2-30% cationic lipid, 2-30% helper lipid, 1-15% cholesterol, 2-35% cholesterol-PEG, and 1-20% cholesterol-amine; or up to 90% cationic lipid and 2-10% helper lipids, or even 100% cationic lipid.

Lipid Conjugates

The lipid-encapsulated RNA nanoparticles described herein may further comprise a lipid conjugate. The conjugated lipid is useful in that it prevents the aggregation of particles. Suitable conjugated lipids include, but are not limited to, PEG-lipid conjugates, cationic-polymer-lipid conjugates, and mixtures thereof. Furthermore, lipid delivery vehicles can be used for specific targeting by attaching ligands (e.g., antibodies, peptides, and carbohydrates) to its surface or to the terminal end of the attached PEG chains (Front Pharmacol. 2015 Dec. 1; 6:286).

In a preferred embodiment, the lipid conjugate is a PEG-lipid. The inclusion of polyethylene glycol (PEG) in a lipid formulation as a coating or surface ligand, a technique referred to as PEGylation, helps to protects nanoparticles from the immune system and their escape from reticuloendothelial system (RES) uptake (Nanomedicine (Lond). 2011 June; 6(4):715-28). PEGylation has been widely used to stabilize lipid formulations and their payloads through physical, chemical, and biological mechanisms. Detergent-like PEG lipids (e.g., PEG-DSPE) can enter the lipid formulation to form a hydrated layer and steric barrier on the surface. Based on the degree of PEGylation, the surface layer can be generally divided into two types, brush-like and mushroom-like layers. For PEG-DSPE-stabilized formulations, PEG will take on the mushroom conformation at a low degree of PEGylation (usually less than 5 mol %) and will shift to brush conformation as the content of PEG-DSPE is increased past a certain level (Journal of Nanomaterials. 2011; 2011:12). It has been shown that increased PEGylation leads to a significant increase in the circulation half-life of lipid formulations (Annu. Rev. Biomed. Eng. 2011 Aug. 15; 130:507-30; J. Control Release. 2010 Aug. 3; 145(3):178-81).

Suitable examples of PEG-lipids include, but are not limited to, PEG coupled to dialkyloxypropyls (PEG-DAA), PEG coupled to diacylglycerol (PEG-DAG), PEG coupled to phospholipids such as phosphatidylethanolamine (PEG-PE), PEG conjugated to ceramides, PEG conjugated to cholesterol or a derivative thereof, and mixtures thereof.

PEG is a linear, water-soluble polymer of ethylene PEG repeating units with two terminal hydroxyl groups. PEGs are classified by their molecular weights and include the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH$_2$), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g., HO-PEG-S, HO-PEG-S-NHS, HO-PEG-NH$_2$).

The PEG moiety of the PEG-lipid conjugates described herein may comprise an average molecular weight ranging from about 550 daltons to about 10,000 daltons. In certain instances, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons). In preferred embodiments, the PEG moiety has an average molecular weight of about 2,000 daltons or about 750 daltons. The average molecular weight may be any value or subvalue within the recited ranges, including endpoints.

In certain instances, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester-containing linker moieties and ester-containing linker moieties. In a preferred embodiment, the linker moiety is a non-ester-containing linker moiety. Suitable non-ester-containing linker moieties include, but are not limited to, amido (—C(O)NH—), amino (—NR—), carbonyl (—C(O)—), carbamate (—NHC(O)O—), urea (—NHC(O)NH—), disulfide (—S—S—), ether (—O—), succinyl (—(O)CCH$_2$CH$_2$C(O)—), succinamidyl (—NHC(O)CH$_2$CH$_2$C(O)NH—), ether, as well as combinations thereof (such as a linker containing both a carbamate linker moiety and an amido linker moiety). In a preferred embodiment, a carbamate linker is used to couple the PEG to the lipid.

In other embodiments, an ester-containing linker moiety is used to couple the PEG to the lipid. Suitable ester-containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the lipid conjugate. Such phosphatidylethanolamines are commercially available or can be isolated or synthesized using conventional techniques known to those of skill in the art. Phosphatidylethanolamines containing saturated or unsaturated fatty acids with carbon chain lengths in the range of C10 to C20 are preferred. Phosphatidylethanolamines with mono- or di-unsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoyl-phosphatidylethanolamine (DOPE), and distearoyl-phosphatidylethanolamine (DSPE).

In some embodiments, the PEG-DAA conjugate is a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, or a PEG-distearyloxypropyl ($C_{18}$) conjugate. In these embodiments, the PEG preferably has an average molecular weight of about 750 or about 2,000 daltons. In particular embodiments, the terminal hydroxyl group of the PEG is substituted with a methyl group.

In addition to the foregoing, other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl, methacrylamide, polymethacrylamide, and polydimethylacrylamide, polylactic acid, polyglycolic acid, and derivatized celluloses such as hydroxymethylcellulose or hydroxyethylcellulose.

In some embodiments, the lipid conjugate (e.g., PEG-lipid) comprises from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 0.9 mol % to about 1.6 mol %, from about 0.9 mol % to about 1.8 mol %, from about 1 mol % to about 1.8 mol %, from about 1 mol % to about 1.7 mol %, from about 1.2 mol % to about 1.8 mol %, from about 1.2 mol % to about 1.7 mol %, from about 1.3 mol % to about 1.6 mol %, or from about 1.4 mol % to about 1.6 mol % (or any fraction thereof or range therein) of the total lipid present in the lipid formulation. In other embodiments, the lipid conjugate (e.g., PEG-lipid) comprises about 0.5%, 0.6%, 0.7%, 0.8%, 0.9%, 1.0%, 1.2%, 1.3%, 1.4%, 1.5%, 1.6%, 1.7%, 1.8%, 1.9%, 2.0%, 2.5%, 3.0%, 3.5%, 4.0%, 4.5%, or 5%, (or any fraction thereof or range therein) of the total lipid present in the lipid formulation and methods of producing the same. The amount may be any value or subvalue within the recited ranges, including endpoints.

The percentage of lipid conjugate (e.g., PEG-lipid) present in the lipid formulations of the disclosure and methods of producing the same is a target amount, and the actual amount of lipid conjugate present in the formulation may vary, for example, by +0.5 mol %. One of ordinary skill in the art will appreciate that the concentration of the lipid conjugate can be varied depending on the lipid conjugate employed and the rate at which the lipid formulation is to become fusogenic.

Lipid-Encapsulated RNA Nanoparticle Formation

Figure 1:
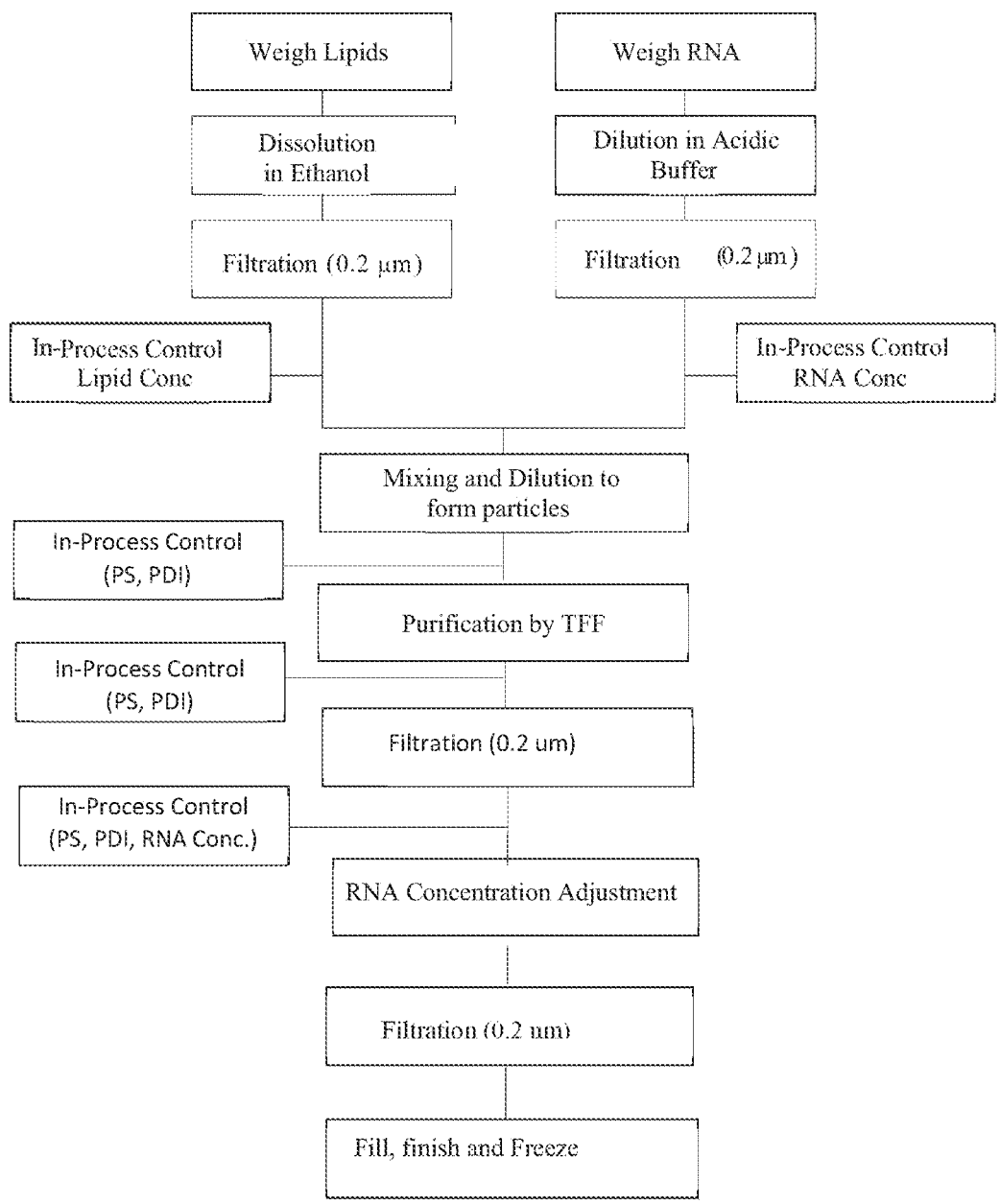
FIG. 1 shows a flow chart diagram for one embodiment of a process of producing lipid nanoparticles. Lipids are dissolved in ethanol, RNA is dissolved in an aqueous acidic buffer (e.g. citrate buffer), both are filter sterilized. The solutions are mixed by the process described herein to form particles, which are analyzed for PDI and particle size (PS). The particles are concentrated and purified by tangential flow filtration (TFF) to remove ethanol and unbound RNA, and PDI and PS is again monitored. The concentration of the particles is then adjusted according to measured total RNA concentration. The particles are filter sterilized, filled, finished, and frozen.

FIG. 1 is an example of a representative flow chart of a method described herein of producing lipid-encapsulated RNA nanoparticles.

The geometry of the mixing layer consists of a first tube for transporting the aqueous solution having an inner diameter (ID) of greater than 0.1", preferably an ID greater than 0.132"; and a second tube for transporting the ethanol solution consisting of a ID greater than 0.005", preferably greater than 0.01"; in which the second (organic) tube intersects the first (aqueous) tube at or near a perpendicular angle. The output flow rate during mixing is at least 200 ml/min, preferably at least 300 ml/min.

The method described herein provides an aqueous RNA solution comprising a therapeutic RNA, e.g., prepared under Good Manufacturing Practice (GMP), solubilized in an aqueous solution comprising a buffer, e.g., citrate. The present method also provides an organic solution comprising one or more lipids, e.g., clinical grade lipids synthesized under GMP, produced by solubilizing lipid in a water-miscible organic solvent. In the method described herein, the water-miscible organic solvent, preferably is a lower alkanol, e.g., ethanol. Preferably, both solutions are filter sterilized and their concentrations are adjusted.

The organic lipid solution is mixed with the aqueous solution comprising a nucleic acid to form a lipid-encapsulated RNA nanoparticle having a lamellar morphology, i.e., including a lipid bilayer. In one aspect, the nucleic acid is encapsulated in the lipid-encapsulated RNA nanoparticles with formation of the lamellar structure.

The method described herein is directed to continuously introducing a lipid solution into the aqueous solution in a mixing environment, preferably perpendicularly in a mixing module. The mixing dilutes the lipid solution with the aqueous solution to 20%, 22.5%, 25%, 27.5%, or 30% ethanol, preferably 25% ethanol, and causes formation of lipid-encapsulated RNA nanoparticles in a turbulent flow.

After formation of the lipid-encapsulated RNA nanoparticles, the mixture is continuously diluted by a buffer to 7.5%, 10%, 12.5%, or 15%, preferably to less than 12.5% ethanol, which further stabilizes the lipid-encapsulated RNA nanoparticles and increases encapsulation of nucleic acid.

The lipid-encapsulated RNA nanoparticles are concentrated by tangential flow filtration, preferably by hollow fiber filters. The concentrated lipid-encapsulated RNA nanoparticles are subjected to an ultrafiltration step to remove the alkanol and substitute the buffer. The nucleic acid concentration is adjusted by dilution. The resulting formulation is filter sterilized and filled in vials. The process will now be discussed in more detail herein below using the steps as set forth in FIG. 1.

Lipid Solubilization and RNA Dissolution

In one embodiment, the lipid-encapsulated RNA nanoparticles produced by the method described herein are in the form of multimolecular assemblies of RNA and lipids, in which the RNA is encapsulated at least in part by ionic pairing with cationic lipids.

The preferred size for lipid-encapsulated nanoparticles comprising RNA made by the method described herein are about 50-200 nm in diameter, preferably, with a size distribution in which the mean size (e.g., diameter) is about 70 nm to about 150 nm, and more preferably the mean size is less than about 100 nm.

In certain aspects, the lipid nanoparticles of the description herein include four lipid components: a helper lipid; cholesterol; a PEG-lipid; and an ionizable cationic lipid. Preferably, the helper lipid is DSPC, the PEG-lipid is PEG-DMG and the ionizable cationic lipid is an ionizable cationic lipid. In certain embodiments, the organic solvent concentration in which the lipids are solubilized is about 45% v/v to about 90% v/v. In certain preferred aspects, the organic solvent is a lower alkanol. Suitable lower alkanols include, e.g., methanol, ethanol, propanol, butanol, pentanol, their isomers and combinations thereof. The solvent is preferably ethanol with a concentration of about 50-90% v/v. Preferably, the lipids occupy a volume of about 1 mL/g to about 5 mL/g.

The lipids are solubilized using for example, an overhead stirrer at a suitable temperature. In one aspect, the total lipid concentration of the solution is about 49.4 mg/mL. In certain preferred aspects, the RNA is included in an aqueous solution (e.g., buffer) and is diluted to a final concentration. Preferably, the final concentration is about 0.55 mg/mL in citrate buffer, with a pH of about 3.5.

The RNA is preferably a double-stranded RNA (dsRNA), a mRNA, or a self-replicating RNA. The size of the dsRNA is between 10 base pairs to several hundred bases, preferably less than 30 base pairs, most preferably less than 25 base pairs. The size of the mRNA is between 10 and several thousand bases in a single strand.

Lipid-Encapsulated RNA Nanoparticle Formation Step

After the organic solution and the aqueous solutions are prepared, they are mixed together using the apparatus described in detail below. Briefly, the apparatus consists of a first tube for transporting the aqueous RNA solution and a second tube for transporting the organic lipid solution, in which the second tube intersects the first tube perpendicularly within the mixing module. The two solutions are pumped through the respective tubes by separate HPLC pumps and mixed in the region of the first tube perpendicularly within the mixing module. Preferably, the aqueous RNA solution is pumped at a rate 2.0-, 2.5-, 3.0-, 3.25-, or 3.5-fold, preferably 3.0-fold, greater than the organic lipid solution. Upon mixing the two solutions in the mixing area, lipid-encapsulated RNA nanoparticles are formed.

The pump speeds and the size of the first tube in the region of the mixing module provides for a mixing process that involves turbulent flow. In fluid dynamics, turbulence or turbulent flow is fluid motion characterized by chaotic changes in pressure and flow velocity. It is in contrast to a laminar flow, which occurs when a fluid flows in parallel layers, with no disruption between those layers. Turbulent flows are always highly irregular, and the readily available supply of energy in turbulent flows tends to accelerate the homogenization (mixing) of fluid mixtures. The characteristic which is responsible for the enhanced mixing and increased rates of mass, momentum and energy transports in a flow is called "diffusivity". Other characteristics of a turbulent flow include "rotationality" as turbulent flows have a strong three-dimensional vortex generation mechanism known as vortex stretching and "dissipation" as turbulence dissipates rapidly as the kinetic energy is converted into internal energy by viscous shear stress. Turbulent mixing is dominated by small scale (compared to the parent flow) random movements of parcels within a fluid that bring them into closer or more distant relationship and may more finely divide and intermingle them. The processes described herein for mixing of the lipid solution and the aqueous solution provides for encapsulation of RNA in the lipid nanoparticles formed coincident with their formation with an encapsulation efficiency of greater than 95%.

Lipid nanoparticles are typically formed at room temperature, but lipid nanoparticles may be formed at elevated temperatures according to the present disclosure. There are no general requirements for buffer composition. In fact, the processes and apparatus of the present disclosure can formulate a lipid vesicle by mixing lipid in ethanol with RNA in an aqueous solution.

In one embodiment, lipid nanoparticles form when lipids dissolved in an organic solvent, e.g., ethanol, are diluted in a stepwise manner by mixing with a buffered aqueous solution, first by mixing the aqueous and lipid streams together in the mixing module to a final concentration of organic solvent preferably between 25-40%. The resultant lipid, solvent and solute concentrations can be kept constant throughout the vesicle formation process. Following the initial formation, the initial lipid-RNA mixture is further diluted by addition of buffer, preferably to about 6.0%, 6.25%, 7.0% 7.5%, 10%, 12.5%, or 15% organic solvent, most preferably 6.25% 6.25%, 7.0% 7.5%, 10%, or 12.5%.

The continuous process described herein is fully scalable. In one aspect, lipid-encapsulated RNA nanoparticles are formed having a mean diameter of less than about 80 nm, without mechanical-energy processes such as membrane extrusion, sonication or microfluidization.

Lipid-Encapsulated RNA Nanoparticles

The lipid-encapsulated RNA nanoparticles disclosed herein comprise a nanoparticle or a bilayer of lipid molecules. In addition to the cationic lipid e.g., an ionizable cationic lipid), the lipid-encapsulated RNA nanoparticle comprises a neutral lipid or a polymer.

In some embodiments, the RNA is fully encapsulated within the lipid portion of the lipid nanoparticle such that the RNA in the lipid-encapsulated RNA nanoparticles is resistant in aqueous solution to nuclease degradation. In other embodiments, the lipid-encapsulated RNA nanoparticles described herein are substantially non-toxic to mammals such as humans. The lipid-encapsulated RNA nanoparticles typically have a mean diameter of from 30 nm to 150 nm, from 40 nm to 150 nm, from 50 nm to 150 nm, from 60 nm to 130 nm, from 70 nm to 110 nm, or from 70 to 90 nm. The lipid-encapsulated RNA nanoparticles described herein also typically have a lipid:RNA ratio (mass/mass ratio) of from 1:1 to 100:1, from 1:1 to 50:1, from 2:1 to 25:1, from 3:1 to 20:1, from 5:1 to 15:1, or from 5:1 to 10:1, or from 10:1 to 14:1, or from 9:1 to 20:1. In some embodiments, the composition has a total lipid:RNA weight ratio of between about 50:1 and 10:1. In some embodiments, the composition has a total lipid:RNA weight ratio of between about 40:1 and 20:1. In some embodiments, the composition has a total lipid:RNA weight ratio of between about 35:1 and 25:1. In some embodiments, the composition has a total lipid:RNA weight ratio of between about 28:1 and 32:1.

In preferred embodiments, the lipid particles comprise an RNA, a cationic lipid (e.g., one or more cationic lipids or salts thereof described herein), a phospholipid, and a conjugated lipid that inhibits aggregation of the particles (e.g., one or more PEG-lipid conjugates). The lipid-encapsulated RNA nanoparticles can also include cholesterol. The lipid-encapsulated RNA nanoparticles may comprise at least 1, 2, 3, 4, 5, 6, 7, 8, 9, 10, or more different RNA that express one or more polypeptides.

In the lipid-encapsulated RNA nanoparticles the RNA may be fully encapsulated within the lipid portion of the particle, thereby protecting the RNA from nuclease degradation. In preferred embodiments, the lipid-encapsulated RNA nanoparticles comprise an RNA that is fully encapsulated within the lipid portion of the particle, thereby protecting the RNA from nuclease degradation. In certain instances, the RNA in the lipid particle is not substantially degraded after exposure of the particle to a nuclease at 37° C. for at least 20, 30, 45, or 60 minutes. In certain other instances, the RNA in the lipid particle is not substantially degraded after incubation of the particle in serum at 37° C. for at least 30, 45, or 60 minutes or at least 2, 3, 4, 5, 6, 7, 8, 9, 10, 12, 14, 16, 18, 20, 22, 24, 26, 28, 30, 32, 34, or 36 hours. In other embodiments, the RNA is complexed with the cationic lipid of the lipid-encapsulated RNA nanoparticles. One of the benefits of the formulations of the present disclosure is that the lipid-encapsulated RNA nanoparticles are substantially non-toxic to mammals such as humans.

In other embodiments, the present disclosure provides a nucleic acid-lipid particle composition comprising a plurality of nucleic acid-lipid particles.

The lipid particle comprises RNA that is fully encapsulated within the lipid portion of the particles, such that from 30% to 100%, from 40% to 100%, from 50% to 100%, from 60% to 100%, from 70% to 100%, from 80% to 100%, from 90% to 100%, from 30% to 95%, from 40% to 95%, from 50% to 95%, from 60% to 95%, from 70% to 95%, from 80% to 95%, from 85% to 95%, from 90% to 95%, from 30% to 90%, from 40% to 90%, from 50% to 90%, from 60% to 90%, from 70% to 90%, from 80% to 90%, or at least 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the particles have the RNA encapsulated therein.

Depending on the intended use of the lipid-encapsulated RNA nanoparticles, the proportions of the components can be varied and the delivery efficiency of a particular formulation can be measured using assays know in the art.

Dilution of the Lipid-Encapsulated RNA Nanoparticles

After mixing the organic lipid solution into the aqueous RNA solution, the extent of RNA encapsulation can be enhanced if the suspension of lipid-encapsulated RNA nanoparticles is further diluted prior to removal of free RNA. In one embodiment the buffer can be two volumes of 15 mM Tris, 50 mM NaCl, 9% sucrose, pH 7.5 to reduce the ethanol concentration to 8.25%. In another embodiment the buffer can be three volumes of 10 mM Tris, 50 mM NaCl, 9% sucrose, pH 7.5 to reduce the ethanol concentration to 6.25%. In another embodiment the buffer can be one volume of 50 mM phosphate buffer, pH 6.0 to reduce ethanol concentration to 12.5%. In another embodiment the buffer can be two volumes of 50 mM phosphate buffer, pH 6.0 to reduce ethanol concentration to 8.3%. In another embodiment the buffer can be three volumes of 50 mM phosphate buffer, pH 6.0 to reduce ethanol concentration to 6.25%. In another embodiment the buffer can be three volumes of 20 mM HEPES, 50 mM NaCl, 9% sucrose, pH 7.4 to reduce the ethanol concentration to 6.25%. In another embodiment the buffer can be 1-3 volumes of 50 mM phosphate buffer, pH 6.0, three volumes of 10 mM Tris, 50 mM NaCl, 9% sucrose, pH 7.5 to reduce the ethanol concentration to 6.25%.

The diluted lipid-encapsulated RNA nanoparticles are then optionally collected in a vessel maintained at 15-20° C. and allowed to incubate from a few minutes to two hours prior to a second dilution step with 10 mM Tris, 50 mM NaCl, 9% sucrose, pH 7.5 or a concentration step.

Sample Concentration

Diluted lipid-encapsulated RNA nanoparticles can be concentrated, e.g., by tangential flow filtration (TFF) using hollow fiber membranes (mPES Kros membranes, Spectrum Laboratories, Inc., Rancho Dominguez, Calif.), optionally via a peristaltic pump or a 4-piston-diaphragm pump or a centrifugal pump (based on principle of magnetic levitation). Methods for such concentration techniques are known in the art and would be readily apparent to a person of ordinary skill.

Removal of Free RNA and Buffer Replacement

Concentration can be followed by diafiltration against 7-10 volumes of 10 mM Tris, 50 mM NaCl, 9% sucrose, pH 7.5 to remove organic solvent and unbound RNA. Preferably, the diafiltration buffer is added via a heat exchanger such that product temperature is maintained at 15-20° C. The formulation can be further concentrated to target a total formulated RNA concentration of >3 mg/mL.

Sterile Filtration

The RNA concentration in the formulation of lipid-encapsulated RNA nanoparticles can then be measured by IPRP-HPLC (Ion Pair Reverse Phase-High Performance Liquid Chromatography) and adjusted to ~2 mg/mL (1.85 to 2.3 mg/mL) by diluting with 10 mM Tris, 50 mM NaCl, 9% sucrose, pH 7.5 containing glycerol such that the final concentration of glycerol in the formulation is 5%. The diafiltered lipid-encapsulated RNA nanoparticles are sterile filtered through a 0.2 μm sterilizing grade filter (PES) at lipid concentrations of 56-69 mg/mL.

Sterile Fill

The filtered formulation can then be aseptically filled into glass vials, stoppered, capped and placed at −20 or −70±5° C.

Apparatus

Figure 4:
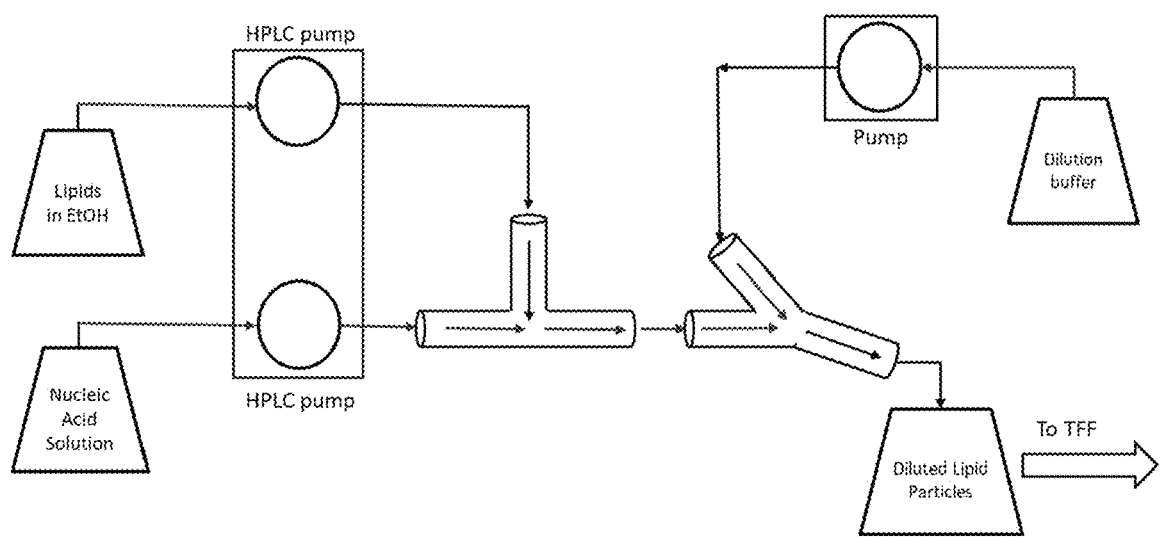
FIG. 4 shows an apparatus for producing lipid-encapsulated RNA nanoparticles.

The description herein provides an apparatus for carrying out the processes described above. FIG. 4 is an example of a representative schematic of an apparatus according to one embodiment of the description herein.

The aqueous solution comprising RNA is transported by an HPLC pump through tubing, e.g., comprising regions of 0.03" ID PEEK tubing, 0.05" ID PEEK connector, 0.0625" silicon tubing, and 0.122" ID silicon tubing, and 0.132" ID stainless steel. The organic solution comprising lipids is transported by an HPLC pump through tubing comprising, e.g., regions of 0.03" ID PEEK tubing, 0.02" ID PEEK connector, 0.01" ID stainless steel. The organic solution is pumped into the aqueous solution at a 90 degree angle in the mixing module. Thus, the organic solution comprising lipids is introduced into the aqueous solution with flow that is perpendicular to the flow of the aqueous solution. This introduction at right angles of flow direction occurs in a mixing module such as that illustrated in FIG. 5, and results in a turbulent mixing, under conditions that are carefully tuned to ensure that lipid nanoparticle encapsulation of the RNA is formed in an acceptable manner regarding particle size, dispersion, and encapsulation efficiency. The tubing containing the mixed lipid-RNA then transports the lipid-encapsulated RNA nanoparticles to a second mixing region, e.g., via 0.25" ID polypropylene tubing which merges at a 45 degree angle with dilution buffer in the dilution area, and the diluted lipid-encapsulated RNA nanoparticles are collected in a stainless steel-jacketed vessel maintained at 15-20° C. The particles are further processed, e.g., by tangential flow filtration using a diaphragm or centrifugal pump.

The mixing area is in one embodiment, a mixing module in which the organic lipid solution is delivered into a stream of the aqueous RNA solution, preferably at an angle of about 90°. A first 0.132" (3.35 mm) ID stainless steel tube transporting the aqueous RNA solution has a hole in its wall midway between its ends. A second 0.01" ID, 0.0625" OD, tube is perpendicularly mounted by a filling through the hole in the wall of the first tube that allows transport of liquid from the second tube to the interior of the first tube (See FIG. 5). In preferred aspects, the lipid-encapsulated RNA nanoparticles' well-defined shape and reproducible size are prepared using a flow rate of the aqueous RNA solution that is preferably three times the flow rate of the organic lipid solution. Vesicles having a well-defined shape and reproducible size are also prepared by changing the flow rate of the fluid lines, e.g., to ensure sufficient mixing in some cases.

FIG. 5 shows a mixing module and associated flow dynamics according to one embodiment. In comparison with prior systems, the present disclosure provides turbulent flow and increased shear rates. For example, the present disclosure advantageously provides turbulent flow ($N_{re}$>2000) in the mixing environment with a shear rate between about 500/s and about 3300/s at a flow rate (both flow lines) of between about 0.1 L/min and about 0.3 L/min.

The description herein provides an apparatus having tangential flow filtration using hollow fiber membranes (mPES Kros membranes, Spectrum Laboratories, Inc., Rancho Dominguez, Calif.) and 4-piston-diaphragm pumps or centrifugal pump.

Pharmaceutical Compositions

Lipid-encapsulated RNA nanoparticles described herein are useful as components in pharmaceutical compositions. These compositions will typically include a pharmaceutically acceptable carrier in addition to the lipid-encapsulated RNA nanoparticles. A thorough discussion of pharmaceutically acceptable carriers is available in Gennaro (2000)

*Remington: The Science and Practice of Pharmacy.* 20th edition, ISBN: 0683306472, incorporated herein by reference in its entirety.

Pharmaceutical compositions described herein may include the lipid nanoparticles in plain water (e.g. Water For Injection) or in a buffer, e.g., a phosphate buffer, a Tris buffer, a borate buffer, a succinate buffer, a histidine buffer, or a citrate buffer. Buffer salts will typically be included in the 5-20 mM range.

Pharmaceutical compositions as described herein may have a pH between 5.0 and 9.5, e.g., between 6.0 and 8.0.

Pharmaceutical compositions as described herein may include sodium salts (e.g. sodium chloride) to give tonicity. The sodium salt can be NaCl at a concentration of 10±2 mg/ml, e.g., about 9 mg/ml.

Pharmaceutical compositions as described herein may include metal ion chelators. These can prolong RNA stability by removing ions that can accelerate phosphodiester hydrolysis, e.g., one or more of EDTA, EGTA, BAPTA, or pentetic acid. Such chelators are preferably at a concentration between 10-500 μM, e.g., 0.1 mM. A citrate salt, such as sodium citrate, can also act as a chelator, while advantageously also providing buffering activity.

Pharmaceutical compositions as described herein preferably have an osmolality of between 200 mOsm/kg and 400 mOsm/kg, e.g., between 240-360 mOsm/kg, or between 290-310 mOsm/kg.

Pharmaceutical compositions as described herein preferably include one or more preservatives, such as thiomersal or 2-phenoxyethanol. Mercury-free compositions are most preferred.

Pharmaceutical compositions as described herein are preferably sterile.

Pharmaceutical compositions as described herein are preferably non-pyrogenic e.g. containing <1 EU (endotoxin unit, a standard measure) per dose, and preferably <0.1 EU per dose.

Pharmaceutical compositions as described herein are preferably gluten free.

Pharmaceutical compositions as described herein may be prepared in unit dose form. In some embodiments a unit dose may have a volume of between 0.1-1.0 mL e.g. about 0.5 mL.

The compositions may be prepared as injectables, either as solutions or suspensions. The composition may be prepared for pulmonary administration, e.g. by an inhaler, using a fine spray. The composition may be prepared for nasal, aural or ocular administration, e.g. as spray or drops.

Pharmaceutical compositions comprise an immunologically effective amount of lipid nanoparticles, as well as any other components, as needed.

Pharmaceutical compositions as described herein are also suitable for administration via a delivery device, e.g., syringe, nebulizer, sprayer, inhaler, or dermal patch, which can be used to administer the composition to a vertebrate subject.

Lipid-encapsulated RNA nanoparticles as described herein do not contain ribosomes.

Definitions

The terms "approximately" or "about," as applied to one or more values of interest, refers to a value that is similar to a stated reference value. In certain embodiments, the term "approximately" or "about" refers to a range of values that fall within +/−10% of the recited value unless otherwise stated or otherwise evident from the context (except where such number would exceed 100% of a possible value).

The terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization-based connectivity sufficiently stable such that the "associated" entities remain physically associated.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

The term "acyl," as used herein, represents a hydrogen or an alkyl group (e.g., a haloalkyl group), as defined herein, that is attached to the parent molecular group through a carbonyl group, as defined herein, and is exemplified by formyl (i.e., a carboxyaldehyde group), acetyl, trifluoroacetyl, propionyl, butanoyl and the like. Exemplary unsubstituted acyl groups include from 1 to 7, from 1 to 11, or from 1 to 21 carbons. In some embodiments, the alkyl group is further substituted with 1, 2, 3, or 4 substituents as described herein.

The term "alkenyl," as used herein, represents monovalent straight or branched chain groups of, unless otherwise specified, from 2 to 20 carbons (e.g., from 2 to 6 or from 2 to 10 carbons) containing one or more carbon-carbon double bonds and is exemplified by ethenyl, 1-propenyl, 2-propenyl, 2-methyl-1-propenyl, 1-butenyl, 2-butenyl, and the like. Alkenyls include both cis and trans isomers. Alkenyl groups may be optionally substituted with 1, 2, 3, or 4 substituent groups that are selected, independently, from amino, aryl, cycloalkyl, or heterocyclyl (e.g., heteroaryl), as defined herein, or any of the exemplary alkyl substituent groups described herein.

The term "alkoxy" represents a chemical substituent of formula —OR, where R is a $C_{1-20}$ alkyl group (e.g., $C_{1-6}$ or $C_{1-10}$ alkyl), unless otherwise specified. Exemplary alkoxy groups include methoxy, ethoxy, propoxy (e.g., n-propoxy and isopropoxy), t-butoxy, and the like. In some embodiments, the alkyl group can be further substituted with 1, 2, 3, or 4 substituent groups as defined herein (e.g., hydroxy or alkoxy).

The term "alkyl," as used herein, is inclusive of both straight chain and branched chain saturated groups from 1 to 20 carbons (e.g., from 1 to 10 or from 1 to 6), unless otherwise specified. Alkyl groups are exemplified by methyl, ethyl, n- and iso-propyl, n-, sec-, iso- and tert-butyl, neopentyl, and the like. The term "lower alkyl" means a group having one to six carbons in the chain which chain may be straight or branched. Non-limiting examples of suitable alkyl groups include methyl, ethyl, n-propyl, isopropyl, n-butyl, t-butyl, n-pentyl, and hexyl.

The term "alkynyl," as used herein, represents monovalent straight or branched chain groups from 2 to 20 carbon atoms (e.g., from 2 to 4, from 2 to 6, or from 2 to 10 carbons) containing a carbon-carbon triple bond and is exemplified by ethynyl, 1-propynyl, and the like. Alkynyl groups may be optionally substituted with 1, 2, 3, or 4 substituent groups that are selected, independently, from aryl, cycloalkyl, or heterocyclyl (e.g., heteroaryl), as defined herein, or any of the exemplary alkyl substituent groups described herein.

The term "amphipathic lipid" or "amphiphilic lipid" means the material in which the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

The term "anionic lipid" means a lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

"Antisense" is a polynucleotide that interferes with the function of DNA and/or RNA. This may result in suppression of expression.

"Aqueous solution" refers to a composition comprising in whole, or in part, water.

The term "back pressure" refers to a resistance or force opposing the desired flow of fluid through a conduit, leading to friction loss and pressure drop. The fluid is directed, tending to flow away from high-pressure regions and toward low-pressure regions.

The term "comprising" is intended to be open and permits but does not require the inclusion of additional elements or steps. When the term "comprising" is used herein, the term "consisting of" is thus also encompassed and disclosed.

The term "composition" means a product comprising the specified ingredients in the specified amounts, as well as any product that results, directly or indirectly, from combination of the specified ingredients in the specified amounts.

The term "commercially available chemicals" and the chemicals used in the Examples set forth herein may be obtained from standard commercial sources, where such sources include, for example, Acros Organics (Pittsburgh, Pa.), Sigma-Adrich Chemical (Milwaukee, Wis.), Avocado Research (Lancashire, U.K.), Bionet (Cornwall, U.K.), Boron Molecular (Research Triangle Park, N.C.), Combi-Blocks (San Diego, Calif.), Eastman Organic Chemicals, Eastman Kodak Company (Rochester, N.Y.), Fisher Scientific Co. (Pittsburgh, Pa.), Frontier Scientific (Logan, Utah), ICN Biomedicals, Inc. (Costa Mesa, Calif.), Lancaster Synthesis (Windham, N. H.), Maybridge Chemical Co. (Cornwall, U.K.), Pierce Chemical Co. (Rockford, Ill.), Riedel de Haen (Hannover, Germany), Spectrum Quality Product, Inc. (New Brunswick, N.J.), TCI America (Portland, Oreg.), and Wako Chemicals USA, Inc. (Richmond, Va.).

The term "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

"Fully encapsulated" means that the RNA in the nucleic acid-lipid particle is not significantly degraded after exposure to serum or a nuclease assay that would significantly degrade free RNA. When fully encapsulated, preferably less than 25% of the nucleic acid in the particle is degraded in a treatment that would normally degrade 100% of free nucleic acid, more preferably less than 10%, and most preferably less than 5% of the nucleic acid in the particle is degraded. "Fully encapsulated" also means that the nucleic acid-lipid particles do not rapidly decompose into their component parts upon in vivo administration.

In the context of nucleic acids, full encapsulation may be determined by performing a membrane-impermeable fluorescent dye exclusion assay, which uses a dye that has enhanced fluorescence when associated with nucleic acid. Encapsulation is determined by adding the dye to a liposomal formulation, measuring the resulting fluorescence, and comparing it to the fluorescence observed upon addition of a small amount of nonionic detergent. Detergent-mediated disruption of the liposomal bilayer releases the encapsulated nucleic acid, allowing it to interact with the membrane-impermeable dye. Nucleic acid encapsulation may be calculated as $E=(I_0-I)/I_0$, where I and $I_0$ refers to the fluorescence intensities before and after the addition of detergent.

"Gene" refers to a nucleic acid (e.g., DNA) sequence that comprises coding sequences necessary for the production of a polypeptide or precursor (e.g., herpes simplex virus). The polypeptide can be encoded by a full-length coding sequence or by any portion of the coding sequence so long as the desired activity or functional properties (e.g., enzymatic activity, ligand binding, signal transduction, and the like) of the full-length polypeptide or fragment thereof are retained.

The term "hydrophobic lipids" means compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacyloxy-3-aminopropane, and 1,2-dialkyl-3-aminopropane.

An "immunologically effective" amount or dose is one that is sufficient to induce an immunological reaction in a subject whereby immunity is established in the subject. Immunity can be verified, for example, by an antibody titer test to determine if enough antibodies against a certain infectious disease are detected in the subject.

"Lamellar morphology" refers to a bilayer structure. The lamellar morphology, bilayer structure of the lipid particles disclosed herein can be determined using analytical techniques, e.g., by cryo-TEM images.

The term "lipid" means an organic compound that comprises an ester of fatty acid and is characterized by being insoluble in water, but soluble in many organic solvents. Lipids are usually divided into at least three classes: (1) "simple lipids", which include fats and oils as well as waxes;

(2) "compound lipids", which include phospholipids and glycolipids; and (3) "derived lipids" such as steroids.

The term "lipid conjugate" means a conjugated lipid that inhibits aggregation of lipid particles. Such lipid conjugates include, but are not limited to, PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides, cationic PEG lipids, polyoxazoline (POZ)-lipid conjugates, polyamide oligomers, and mixtures thereof. PEG or POZ can be conjugated directly to the lipid or may be linked to the lipid via a linker moiety. Any linker moiety suitable for coupling the PEG or the POZ to a lipid can be used including, e.g., non-ester-containing linker moieties and ester-containing linker moieties. In certain preferred embodiments, non-ester-containing linker moieties, such as amides or carbamates, are used.

The term "lipid delivery vehicle" means a lipid formulation that can be used to deliver a therapeutic nucleic acid (e.g., mRNA) to a target site of interest (e.g., cell, tissue, organ, and the like). The lipid delivery vehicle can be a nucleic acid-lipid particle, which can be formed from a cationic lipid, a non-cationic lipid (e.g., a phospholipid), a conjugated lipid that prevents aggregation of the particle (e.g., a PEG-lipid), and optionally cholesterol. Typically, the therapeutic nucleic acid (e.g., mRNA) may be encapsulated in the lipid portion of the particle, thereby protecting it from enzymatic degradation.

"Lipid nanoparticle" is any lipid composition that can be used to deliver a compound including, but not limited to, liposomes, which comprise a lipid bilayer, either as unilamellar or multilamellar structure, in which the RNA is encapsulated at least in part by ionic pairing with cationic lipids. When a lipid nanoparticle is a liposome, it is considered to have an aqueous interior. Other lipid nanoparticles have a solid interior in which the lipid layer (which can be a bilayer or a monolayer) is directly associated with the encapsulated material (e.g., nucleic acid).

"Lipid-encapsulated" can refer to a lipid formulation which provides a compound with full encapsulation, partial encapsulation, or both, in which RNA (or another nucleic acids) is not accessible to RNase-mediated hydrolysis or to intercalation of dyes.

The term "messenger RNA" (mRNA) refers to any polynucleotide which encodes a protein or polypeptide of interest and which is capable of being translated to produce the encoded protein or polypeptide of interest in vitro, in vivo, in situ or ex vivo.

The term "neutral lipid" means a lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" means an amphipathic lipid, a neutral lipid or anionic lipid as described herein.

The term "nucleic acid" means deoxyribonucleotides or ribonucleotides and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2'-O-methyl ribonucleotides, peptide-nucleic acids (PNAs).

The term "nucleotide" is meant to include nucleotides that have natural bases (standard) or modified bases well known in the art. Such bases are generally located at the 1' position of a nucleotide sugar moiety. Nucleotides generally comprise a base, sugar, and a phosphate group. The nucleotides can be unmodified or modified at the sugar, phosphate, and/or base moiety, (also referred to interchangeably as nucleotide analogs, modified nucleotides, non-natural nucleotides, non-standard nucleotides and other; see, for example, Usman and McSwiggen, supra; Eckstein, et al., International PCT Publication No. WO 92/07065; Usman, et al., International PCT Publication No. WO 93/15187; Uhlman & Peyman, supra, all are hereby incorporated by reference herein). There are several examples of modified nucleic acid bases known in the art as summarized by Limbach, et al, Nucleic Acids Res. 22:2183, 1994. Some of the non-limiting examples of base modifications that can be introduced into nucleic acid molecules include: inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g., 6-methyluridine), propyne, and others (Burgin, et al., Biochemistry 35:14090, 1996; Uhlman & Peyman, supra). By "modified bases" in this aspect is meant nucleotide bases other than adenine, guanine, cytosine, and uracil at 1' position or their equivalents.

"Organic lipid solution" refers to a composition comprising in whole, or in part, an organic solvent having a lipid. The organic lipid solution preferably comprises an alkanol, most preferably ethanol.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

The phrase "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, Pharmaceutical Salts: Properties, Selection, and Use, P. H. Stahl and C. G. Wermuth (eds.), Wiley-VCH, 2008, and Berge et al., Journal of Pharmaceutical Science, 66, 1-19 (1977), each of which is incorporated herein by reference in its entirety.

"Ribonucleic acid" or "RNA" refers to a polymer containing at least two ribonucleotides. "Ribonucleotides" contain a sugar ribose, a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkyl halides.

RNA may be in the form of oligonucleotide RNA, tRNA (transfer RNA), snRNA (small nuclear RNA), rRNA (ribosomal RNA), mRNA (messenger RNA), antisense RNA, siRNA (small interfering RNA), self-replicating RNA, ribozymes, chimeric sequences, or derivatives of these groups. The RNA can include (in addition to any 5' cap structure) one or more nucleotides having a modified nucleobase, including m5C (5-methylcytidine), m5U (5-methyluridine), m6A (N6-methyladenosine), s2U (2-thiouridine), Um (2'-O-methyluridine), m1A (1-methyladenosine); m2A (2-methyladenosine); Am (2'-O-methyladenosine); ms2m6A (2-methylthio-N6-methyladenosine); i6A (N6-isopentenyladenosine); ms2i6A (2-methylthio-N6isopentenyladenosine); io6A (N6-(cis-hydroxyisopentenyl)adenosine); ms2io6A (2-methylthio-N6-(cis-hydroxyisopentenyl) adenosine); g6A (N6-glycinylcarbamoyladenosine); t6A (N6-threonyl carbamoyladenosine); ms2t6A (2-methylthio-N6-threonyl carbamoyladenosine); m6t6A (N6-methyl-N6-threonylcarbamoyladenosine); hn6A(N6.-hydroxynorvalylcarbamoyl adenosine); ms2hn6A (2-methylthio-N6-hydroxynorvalyl carbamoyladenosine); Ar(p) (2'-O-ribosyladenosine (phosphate)); I (inosine); ml 1 (1-methylinosine); m'Im (1,2'-O-dimethylinosine); m3C (3-methylcytidine); Cm (2T-O-methylcytidine); s2C (2-thiocytidine); ac4C (N4-acetylcytidine); f5C (5-fonnylcytidine); m5Cm (5,2-O-dimethylcytidine); ac4Cm (N4acetyl2TOmethylcytidine); k2C (lysidine); m1G (1-methylguanosine); m2G (N2-methylguanosine); m7G (7-methylguanosine); Gm (2'-O-methylguanosine); m22G (N2,N2-dimethylguanosine); m2Gm (N2,2'-O-dimethylguanosine); m22Gm (N2,N2,2'-O-trimethylguanosine); Gr(p) (2'-O-ribosylguanosine (phosphate)); yW (wybutosine); o2yW (peroxywybutosine); OHyW (hydroxywybutosine); OHyW* (undermodified hydroxywybutosine); imG (wyosine); mimG (methylguanosine); Q (queuosine); oQ (epoxyqueuosine); galQ (galtactosyl-queuosine); manQ (mannosyl-queuosine); preQo (7-cyano-7-deazaguanosine); preQi (7-aminomethyl-7-deazaguanosine); G* (archaeosine); D (dihydrouridine); m5Um (5,2'-O-dimethyluridine); s4U (4-thiouridine); m5s2U (5-methyl-2-thiouridine); s2Um (2-thio-2'-O-methyluridine); acp3U (3-(3-amino-3-carboxypropyl)uridine); ho5U (5-hydroxyuridine); mo5U (5-methoxyuridine); cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonyl methyluridine); mcm5Um (S-methoxycarbonylmethyl-2-O-methyluridine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyl uridine); ncm5Um (5-carbamoylmethyl-2'-O-methyluridine); cmnm5U (5-carboxymethylaminomethyluridine); cnmm5Um (5-carboxymethylaminomethyl-2-L-O-methyluridine); cmnm5s2U (5-carboxymethylaminomethyl-2-thiouridine); m62A (N6,N6-dimethyladenosine); Tm (2'-O-methylinosine); m4C (N4-methylcytidine); m4Cm (N4,2-O-dimethylcytidine); hm5C (5-hydroxymethylcytidine); m3U (3-methyluridine); cm5U (5-carboxymethyluridine); m6Am (N6,T-O-dimethyladenosine); m62Am (N6,N6,O-2-trimethyladenosine); m2'7G (N2,7-dimethylguanosine); m2'2'7G (N2,N2,7-trimethylguanosine); m3Um (3,2T-O-dimethyluridine); m5D (5-methyldihydrouridine); f5Cm (5-formyl-2'-O-methylcytidine); m1Gm (1,2'-O-dimethylguanosine); m'Am (1,2-O-dimethyl adenosine) irinomethyluridine); tm5s2U (S-taurinomethyl-2-thiouridine)); imG-14 (4-demethyl guanosine); imG2 (isoguanosine); or ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-(C1-C6)-alkyluracil, 5-methyluracil, 5-(C2-C6)-alkenyluracil, 5-(C2-C6)-alkynyluracil, 5-(hydroxymethyl)uracil, 5-chlorouracil, 5-fluorouracil, 5-bromouracil, 5-hydroxycytosine, 5-(C1-C6)-alkylcytosine, 5-methylcytosine, 5-(C2-C6)-alkenylcytosine, 5-(C2-C6)-alkynylcytosine, 5-chlorocytosine, 5-fluorocytosine, 5-bromocytosine, N2-dimethylguanine, 7-deazaguanine, 8-azaguanine, 7-deaza-7-substituted guanine, 7-deaza-7-(C2-C6)alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, or an abasic nucleotide.

The RNA may comprise one or more UNA molecules, e.g., as disclosed in U.S. Pat. Nos. 8,314,227, 9,051,570, 9,303,260, 9,297,009, and 9,340,789, and U.S. Patent Publication No. 2016/0168567, incorporated herein in their entirety.

The RNA or self-replicating RNA can include one or more modified pyrimidine nucleobases, such as pseudouridine and/or 5-methylcytosine residues.

"Self-replicating RNA" refers to RNAs which can, when released to a cell from a mammal even without any protein, lead to the production of multiple child RNAs by transcription of itself (by an antisense copy that generates itself). A self-replicating RNA molecule is usually a positive-strand molecule that can be translated directly upon release to a cell, and this translation provides an RNA-dependent RNA polymerase that then produces both antisense and sense transcripts of the released RNA. The child RNAs, as well as the collinear subgenomic transcripts, can be translated by themselves to provide in situ the expression of an encoded protein (e.g., and antigen or immunogen), or they can be transcribed to provide additional transcripts in the same sense as the released RNA that are translated to provide on-site the protein expression. The overall result of this transcription sequence is a large amplification in the number of RNA replicons introduced and in this way the encoded protein becomes a main product of the transfected cells. Examples of self-replicating RNA are described in WO 2012/006369 and US 2018/0104359, the contents of which are incorporated by reference.

"Turbulence" is defined herein in terms of the geometry of the mixing area, and the flow rates of the aqueous solution comprising RNA and the ethanol solution comprising a lipid mixture. During mixing the Reynolds number is at least 2000, in which the Reynolds number Re is defined as $$Re = DV\rho/\mu$$

where: $\rho$ is the density of a solution comprising 0 to 25% ethanol in water (g/cm$^3$), V is the velocity of the solution with respect to the tubing (cm/s), D is the ID of the tubing (cm), t is the dynamic viscosity of the solution (g/(cm·s)). Tilton, *Fluid and Particle Dynamics*, PERRY'S CHEMICAL ENGINEERS' HANDBOOK (Green ed., 8$^{th}$ ed. 2008) (incorporated herein in its entirety) at page 6-51. Transitions to turbulent flow occur with Reynolds number Re in the range of 2000 to 2500 (Tilton at 6-14). For example, at 300 ml/min flow rate in tubing with ID=0.132", Re is 2,100 (D=0.30 cm, V=70 cm/sec, $\rho$=96 g/cm$^3$, and $\mu$=0.01 gm/(cm sec) (Poling, *Physical and Chemical Data*, in PERRY'S, at 2-117 and 2-448, respectively). Taking the velocity profile of the tube into account, centerline velocity v as a function of radial position r in a circular pipe of radius R (D/2) is defined as $$v = 2V(1 - r^2/R^2)$$

where the maximum velocity is twice the effective velocity for a parabolic profile (Tilton, at 6-11). For example, at a flow rate of 300 ml/min, the Reynolds number in the center of the tube is 4,200. For this reason, it is possible to determine a flow rate in which turbulence is produced at least in the center of the tubing, and to a considerable extent toward the walls.

EXAMPLES

Example 1: Effect of Flow Rate on Particle Size

A reservoir containing siRNA at a concentration of 0.55 mg/mL and another reservoir with total lipid at a concentration of 49.4 mg/mL were prepared, as shown in FIG. 1.

The lipid compositions were formulated in the range cationic lipid:DSPC:Cholesterol:PEG-DMG, 48-60:5-10:28-38:0.5-3.0 mol %. The ratio of total lipid to RNA was 25:1 to 30:1, wt:wt.

The lipid solution was pumped from the reservoir through a mixing module by an HPLC pump through tubing having a 0.01" lipid inlet at flow rates from 25 to 87.5 ml/min. The siRNA solution was pumped from the reservoir through a module by an HPLC pump through tubing having 0.132" siRNA inlet. The flow rate of the siRNA was three-times the flow rate of the lipids, and the output of the mixing was a 25% EtOH solution. The output solution was further diluted in buffer, and free RNA and ethanol was removed by Tangential Flow Filtration (TFF). FIGS. 1, 4, and 5 schematically shows the overall process with FIG. 1 outlining the steps of the production, FIG. 4 showing an apparatus schematic, and FIG. 5 providing an illustration of a mixing module of the present disclosure.

Various properties of the lipid-encapsulated RNA nanoparticles were measured, including average particle size (nm), polydispersity index (PDI), and percentage encapsulation. Formulation yields were >80% for all conditions tested. The results are shown in Table 2.

TABLE 2

Varying flow rates during mixing

| Flow Rate, ml//min | | | Average Particle Size (nm) | PDI | % Encapsulated | Yield (%) | RNA to Lipid Ratio (wt/wt) |
| --- | --- | --- | --- | --- | --- | --- | --- |
| Lipid | siRNA | Total | | | | | |
| 25 | 75 | 100 | 106.9 | 0.09 | 99.1 | 76 | 0.03 |
| 50 | 150 | 200 | 75.7 | 0.08 | 99.4 | 82 | 0.03 |
| 75 | 225 | 300 | 71.2 | 0.07 | 99.3 | 85 | 0.03 |
| 87.5 | 262.5 | 350 | 66.4 | 0.08 | 98.7 | 80 | 0.03 |

The results showed that increasing the flow rate of the lipid and RNA decreased the average particle size while maintaining the PDI at <0.1, and encapsulation at around 99%.

Example 2: Process Scalability and Reproducibility

The conditions of Example 1 were followed using a combined flow rate of 300 ml/min for a batch volume from 1 liter to 220 liters. The results are shown in Table 3.

TABLE 3

Scalability and reproducibility of physicochemical properties

| Batch Volume (L) | Average Particle Size (nm) | PDI | % Encapsulated siRNA | RNA/Lipid Ratio (wt/wt) |
| --- | --- | --- | --- | --- |
| 1.8 | 75.4 | 0.07 | 96.9 | 0.03 |
| 3.5 | 73.6 | 0.04 | 98.7 | 0.03 |

TABLE 3-continued

Scalability and reproducibility of physicochemical properties

| Batch Volume (L) | Average Particle Size (nm) | PDI | % Encapsulated siRNA | RNA/Lipid Ratio (wt/wt) |
|---|---|---|---|---|
| 7.3 | 73.7 | 0.04 | 99.1 | 0.03 |
| 22 | 76.1 | 0.04 | 99.1 | 0.03 |
| 110 | 76.0 | 0.06 | 99.0 | 0.03 |
| 220 | 76.0 | 0.06 | 99.0 | 0.03 |
| 220 | 75.3 | 0.05 | 99.0 | 0.03 |
| 220 | 75.0 | 0.04 | 99.0 | 0.03 |

The results demonstrate that the process disclosed herein using turbulence can be scaled from 1.8 liters to 220 liters. The key physicochemical and biological properties are unchanged through the scaling. FIG. 7 provides cryo-TEM (transmission electron microscopy) micrographs that show that particles produced are uniform in size at 220 L batch, with a unilamellar morphology.

The scalability of the process disclosed herein was measured using the conditions disclosed in Example 1 by varying the amount RNA processed from 0.05 to 30 grams at a flow rate of 300 ml/min, and measuring particle size, PDI and % encapsulation. The results are shown in FIG. 6A. The results demonstrate that the size of the particles remains between 70 and 80 nm during the scale up from 0.5 grams to 30 grams.

The reproducibility of the process was measured by preparing several batches of 30 g RNA lipid nanoparticles independently. The results are shown in FIG. 6B. The results demonstrate inter-batch reproducibility, in which particle size of 70-80 nm was obtained.

Final formulation yields were >80% across all scales from 1.8-220 L.

The effect of the particles produced in the 220 L batches by the process disclosed herein by injection i.v. into tail vein of Balb/c mice. The results are shown in Table 4.

TABLE 4

| Process | Dose 15 mg/kg | Dose 20 mg/kg |
|---|---|---|
| Turbulence | Well Tolerated | Well Tolerated |

The results show that the lipid-encapsulated RNA nanoparticles produced by turbulent flow were tolerated at a dose of up to at least 20 mg/kg.

Example 3: Effect of Changing siRNA Concentration

The method of Example 1 was used with a lipid flow rate of 75 ml/min, an siRNA flow rate of 225 ml/min and a total flow rate, 300 ml/min. The in-process concentration of siRNA before dilution was varied from 0.083 mg/ml to 0.41 mg/ml, and the concentration of lipid was increased proportionally to maintain the RNA:lipid ratio. The results are shown in Table 5.

TABLE 5

Varying in-process concentrations during mixing

| Batch ID | siRNA concentration (mg/ml) | Total Lipid concentration (ug/ml) | Average Particle Size (nm) | PDI | % Encapsulated | RNA/Lipid Ratio (wt/wt) |
|---|---|---|---|---|---|---|
| 5 | 0.41 | 12.22 | 70.3 | 0.08 | 96.8 | 0.03 |
| 6 | 0.33 | 9.84 | 67.9 | 0.08 | 98.3 | 0.03 |
| 7 | 0.25 | 7.46 | 67.1 | 0.09 | 97.8 | 0.03 |
| 8 | 0.17 | 5.07 | 68.1 | 0.10 | 97.0 | 0.03 |
| 9 | 0.083 | 2.48 | 68.2 | 0.10 | 97.3 | 0.03 |

The results showed that the in-process concentration of RNA can be varied without changing the particle size or percentage of RNA encapsulated.

Example 4: Effect of Module Size

The conditions of Example 1 were followed using a ratio of RNA:lipid of 0.03, wt:wt. The effect of varying the module inlet diameters were measured varying the flow rate from 40 to 600 ml/min, total, as shown with results in Table 6. Inlet pressure was monitored, and the size PDI and percentage encapsulation of the resulting lipid-encapsulated RNA particles were measured.

TABLE 6

Varying module inlet diameters

| Batch ID | inlet ID (inch) Lipid | inlet ID (inch) siRNA | inlet pressure (psi) Lipid | inlet pressure (psi) siRNA | Flow Rate (ml/min) Lipid | Flow Rate (ml/min) siRNA | Flow Rate (ml/min) Total | Average Particle Size (nm) | PDI | % Encapsulated | RNA/Lipid Ratio (wt/wt) |
|---|---|---|---|---|---|---|---|---|---|---|---|
| 10 | 0.005 | 0.132 | 209 | 0 | 10 | 30 | 40 | 131 | 0.09 | 98.1 | 0.03 |
| 11 | | | 386 | 0 | 15 | 45 | 60 | 94.07 | 0.14 | 98.5 | 0.03 |
| 12 | | | 622 | 0 | 20 | 60 | 80 | 70.83 | 0.10 | 98.2 | 0.03 |
| 13 | 0.007 | | 172 | 0 | 25 | 75 | 100 | 97.74 | 0.12 | 98.6 | 0.03 |
| 14 | | | 244 | 3 | 30 | 90 | 120 | 84.88 | 0.14 | 98.6 | 0.03 |
| 15 | | | 439 | 8 | 35 | 105 | 140 | 72.62 | 0.12 | 98.5 | 0.03 |
| 16 | | | 617 | 14 | 40 | 120 | 160 | 64.28 | 0.09 | 97.7 | 0.03 |
| 17 | 0.01 | | 5 | 0 | 25 | 75 | 100 | 106.9 | 0.09 | 99.1 | 0.03 |
| 18 | | | 96 | 27 | 50 | 150 | 200 | 75.7 | 0.08 | 99.4 | 0.03 |
| 19 | | | 343 | 75 | 75 | 225 | 300 | 69.06 | 0.11 | 98.0 | 0.03 |
| 20 | | | 477 | 101 | 87.5 | 262.5 | 350 | 66.38 | 0.08 | 98.7 | 0.03 |
| 21 | 0.02 | | 0 | 100 | 75 | 225 | 300 | 135.6 | 0.08 | 98.8 | 0.03 |
| 22 | | | 2 | 170 | 100 | 300 | 400 | 119.6 | 0.12 | 98.2 | 0.03 |
| 23 | | | 56 | 345 | 150 | 450 | 600 | 100.4 | 0.16 | 98.6 | 0.03 |

TABLE 6-continued

Varying module inlet diameters

| Batch ID | inlet ID (inch) Lipid | inlet ID (inch) siRNA | inlet pressure (psi) Lipid | inlet pressure (psi) siRNA | Flow Rate (ml/min) Lipid | Flow Rate (ml/min) siRNA | Flow Rate (ml/min) Total | Average Particle Size (nm) | PDI | % Encapsulated | RNA/Lipid Ratio (wt/wt) |
|---|---|---|---|---|---|---|---|---|---|---|---|
| 24 | 0.005 | 0.1 | 186 | 0 | 10 | 30 | 40 | 136.8 | 0.11 | 98.0 | 0.03 |
| 25 | | | 350 | 0 | 15 | 45 | 60 | 104.6 | 0.16 | 98.1 | 0.03 |
| 26 | | | 566 | 0 | 20 | 60 | 80 | 81.24 | 0.13 | 97.5 | 0.03 |

The results show that without changing the composition, only by changing the lipid and/or siRNA inlets' IDs of the mixing module can generate different sizes of nanoparticles with >=99% encapsulation efficiency and >=80% yields.

Example 5: Producing Lipid-Encapsulated RNA Nanoparticles Containing mRNA or Self-Replicating RNA The conditions of Example 1 were followed using a module with 0.01" lipid inlet and 0.132" siRNA inlet, a lipid flow rate of 75 ml/min, an mRNA flow rate of 225 ml/min, total flow rate, 300 ml/min. Single stranded mRNA was used having varying size from 265 kDa to 3,858 kDa RNA, keeping the RNA/total lipid (wt/wt) ratio of 0.025 to 0.035. The RNA used was a mRNA or a self-replicating RNA, containing a replicon region.

TABLE 7

Varying nucleic acid size (mRNA)

| Batch ID | mRNA MW Da | mRNA Length (number of nucleotides) | Average Particle Size (nm) | PDI | % Encapsulated | RNA/Lipid Ratio (wt/wt) |
|---|---|---|---|---|---|---|
| 27 | 265,213 | 827 | 73.3 | 0.09 | 95.2 | 0.03 |
| 28 | 677,000 | 2,082 | 73.0 | 0.08 | 94.2 | 0.03 |
| 29 | 1,389,000 | 4,269 | 73.0 | 0.06 | 95.0 | 0.03 |
| 30 | 1,782,362 | 5,489 | 82.1 | 0.08 | 96.1 | 0.03 |
| 31 | 3,857,750 | 11,870 | 93.4 | 0.20 | 96.5 | 0.03 |

The results shown in Table 7 show that mRNA up to about 0.8 to 12 kilobases (kb) can be packaged with about 95-97% encapsulation using the process described herein. The size of the resulting particles increases only at mRNA lengths of greater than 5.5 kb.

Example 6: Producing Lipid-Encapsulated RNA Nanoparticles Containing mRNA or Self-Replicating RNA The conditions of Example 1 were followed using a module with 0.01" lipid inlet and 0.132" siRNA inlet, a lipid flow rate of 75 ml/min, an mRNA flow rate of 225 ml/min, total flow rate, 300 ml/min. Single stranded mRNA was used having varying size from 265 kDa to 3,858 kDa RNA, keeping the RNA/total lipid (wt/wt) ratio of 0.025 to 0.035. The RNA used was a mRNA or a self-replicating RNA, containing a replicon region.

Example 6: Bioactivity of Lipid-Encapsulated Nanoparticles In Vivo

Lipid-encapsulated RNA nanoparticles containing either EPO mRNA or FVII siRNA were formulated using the process described herein, followed by injection to Balb/c mice (6-8 week-old) mice respectively. Levels of Erythropoietin (EPO) protein and FVII protein in mice serum or plasma were evaluated afterwards to determine the bioactivity of these nanoparticles.

Using a liver-directed in vivo screen of the lipid libraries, a series of compounds were tested that facilitate high levels of siRNA mediated gene silencing in hepatocytes, the cells comprising the liver parenchyma. Factor VII, a blood clotting factor, is a suitable target gene for assaying functional siRNA delivery to liver. Because this factor is produced specifically in hepatocytes, gene silencing indicates successful delivery to parenchyma, as opposed to delivery to the cells of the reticulo-endothelial system (e.g., Kupffer cells). Furthermore, Factor VII is a secreted protein that can be readily measured in serum, obviating the need to euthanize animals. Silencing at the mRNA level can be readily determined by measuring levels of protein. This is because the protein's short half-life (2-5 hour). Compositions with siRNA directed to Factor VII were formulated. Female C57BL/6 mice (6-8 week old) were used for FVII siRNA knockdown (KD) experiments.

The process of Example 1 was followed. In vivo bioactivity in mice were measured as described above. The results are shown in Table 8.

TABLE 8

In vivo results for lipid-encapsulated RNA nanoparticles

| RNA Type | Lipid mol % | Target API/tot. lipid (wt/wt) | Flow Rate (ml/min) Lipid | Flow Rate (ml/min) RNA | Flow Rate (ml/min) Total | Average Particle Size (nm) | PDI | % Encapsulated | In vivo Bioactivity in mice |
|---|---|---|---|---|---|---|---|---|---|
| epo mRNA | 50:7:40:3 | 0.028 | 75 | 225 | 300 | 81.6 | 0.11 | 96.1 | 47 ng/ml EPO protein @ 0.3 mg/kg mRNA |

TABLE 8-continued

In vivo results for lipid-encapsulated RNA nanoparticles

| RNA Type | Lipid mol % | Target API/tot. lipid (wt/wt) | Flow Rate (ml/min) | | | Average Particle Size (nm) | PDI | % Encapsulated | In vivo Bioactivity in mice |
|---|---|---|---|---|---|---|---|---|---|
| | | | Lipid | RNA | Total | | | | |
| FVII siRNA | 58:7:33.5:1.5 | 0.034 | 50 | 150 | 200 | 68.9 | 0.08 | 93.7 | 92.5% FVII mRNA knockdown @ 0.2 mg/kg siRNA |

The results showed that both EPO mRNA-mediated expression and FVII siRNA-mediated knock down (KD) of FVII expression were potent in the Lipid-enabled RNA nanoparticles containing either EPO mRNA or FVII siRNA formulated using the process described herein.

Example 7: In Vivo Bioactivity of Lipid-Encapsulated mRNA Particles Using Different Lipid Compositions Lipid-enabled RNA nanoparticles with varied lipid compositions containing EPO mRNA were formulated respectively using the process described herein. The ionizable cationic lipid was varied: Lipid 1 from Table 1 was compared to Lipid 2, Lipid 3 and Lipid 9. The structure of ionizable cationic lipids are shown below. The compositions of the formulation are shown in Table 9.

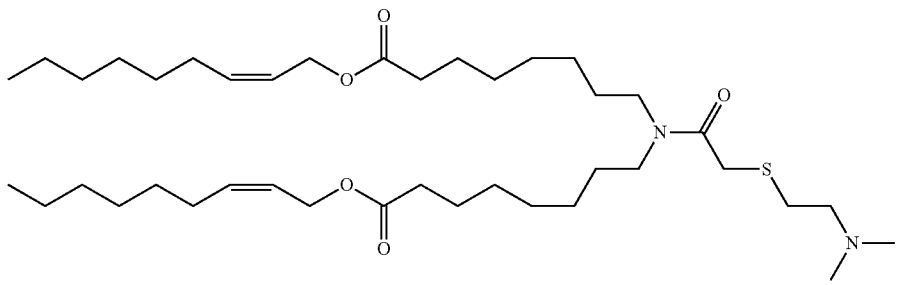

Lipid 1

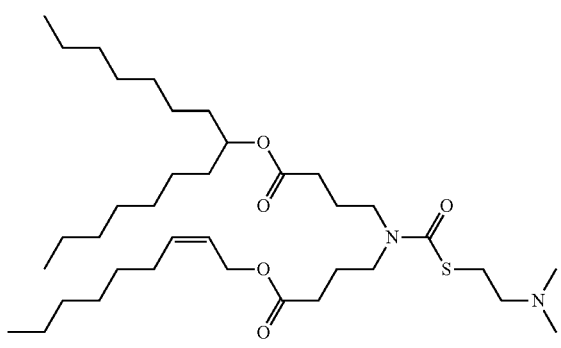

Lipid 2

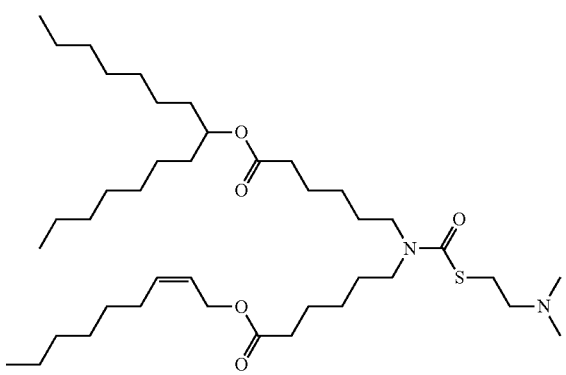

Lipid 3

-continued

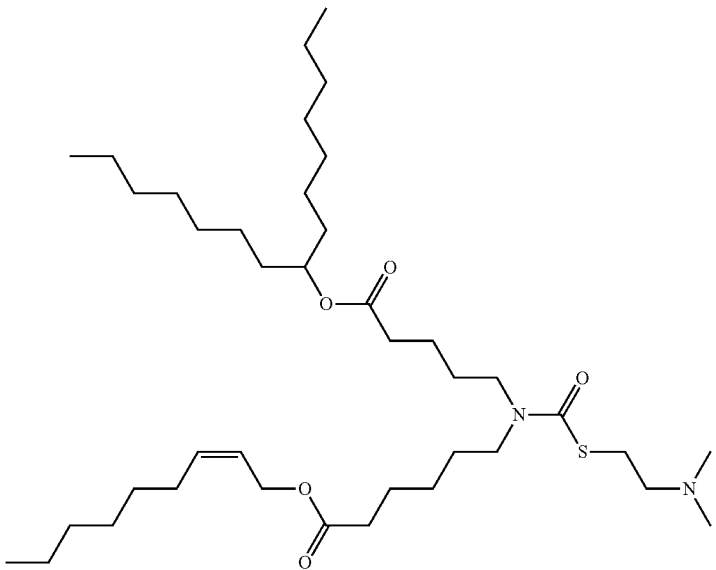 [SMILES: CCCCCC/C=C\COC(=O)CCCCCN(CCCCC(=O)OC(CCCCCCC)CCCCCCC)C(=O)SCCN(C)C]

Lipid 9

EPO protein expression (ng/ml) in serum was measured after a 0.3 mg/kg mRNA single dose in Female Balb/c mice (6-8 week-old). A PBS negative control gave EPO expression of 2 ng/ml. The results of the comparison are shown in Table 9.

TABLE 9

In vivo results for lipid-encapsulated RNA nanoparticles

| Lipid Composition | Lipid Mol % | RNA/lipid (wt/wt) | RNA (mg/ml) | Average Particle Size (nm) | PDI | % Encapsulated | EPO Protein expression (ng/ml) |
|---|---|---|---|---|---|---|---|
| Lipid 1: DSPC:PEG_DMG | 48-60:5-10:35-45:1-4 | 0.03 | 0.14 | 81.4 | 0.07 | 92.1 | 95 |
| Lipid 2: DSPC:PEG_DMG | 48-60:5-10:28-38:0.5-3.0 | 0.03 | 0.17 | 68.1 | 0.16 | 93.4 | 92 |
| Lipid 3: DSPC:PEG_DMG | | 0.03 | | 73.7 | 0.08 | 94.9 | 146 |
| Lipid 9: DSPC:PEG_DMG | | 0.03 | | 71.1 | 0.10 | 94.9 | 154 |

The results showed that although particle size was comparable, EPO protein expression substantially varied among the lipid-enabled EPO mRNA nanoparticles with different ionizable cationic lipids and compositions. Using the process described herein, all lipid-enabled EPO mRNA nanoparticles made were potent. Yields of >85% were observed for compositions tested.

Further Considerations

The foregoing description is provided to enable a person skilled in the art to practice the various configurations described herein. There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed:

1. A method of producing a lipid-encapsulated RNA nanoparticle, comprising the steps a) flowing an aqueous solution comprising an RNA through a $1^{st}$ tube having an inner diameter (ID) of between about 0.1" and 0.132";
b) flowing an ethanol solution comprising lipids through a $2^{nd}$ tube having an ID of between about 0.005" and 0.02" at one third the flow rate of the aqueous solution through the $1^{st}$ tube, wherein the lipids comprise a cationic lipid; and
c) mixing the ethanol solution with the aqueous solution by flowing the ethanol solution and the aqueous solution into a mixing module consisting of the $2^{nd}$ tube perpendicularly joined to the $1^{st}$ tube;

wherein the mixing produces an output solution flowing in the $1^{st}$ tube comprising a turbulent flow of the RNA and the lipids in between about 10% to 75% ethanol v/v;
wherein the lipid-encapsulated RNA nanoparticles have a bilayer structure;
wherein the RNA is encapsulated at greater than 98%;
wherein the polydispersity index is less than 0.09; and,
wherein the cationic lipid has a pKa of about 6 to about 7 and a structure of Formula I:

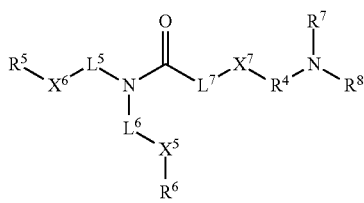

or a pharmaceutically acceptable salt or solvate thereof, wherein
$R^5$ and $R^6$ are each independently selected from the group consisting of a linear or branched $C_1$-$C_{31}$ alkyl, $C_2$-$C_{31}$ alkenyl or $C_2$-$C_{31}$ alkynyl and cholesteryl;
$L^5$ and $L^6$ are each independently selected from the group consisting of a linear $C_1$-$C_{20}$ alkyl and $C_2$-$C_{20}$ alkenyl;
$X^5$ is —C(O)O— or —OC(O)—;
$X^6$ is —C(O)O— or —OC(O)—;
$X^7$ is S or O;
$L^7$ is absent or lower alkyl;
$R^4$ is a linear or branched $C_1$-$C_6$ alkyl; and
$R^7$ and $R^8$ are each independently selected from the group consisting of a hydrogen and a linear or branched $C_1$-$C_6$ alkyl.

2. The method of claim 1, wherein the output has a flow rate of at least 200 ml/min.

3. The method of claim 1, wherein the flow rate of the output has a Reynolds number of at least 2,000.

4. The method of claim 1, wherein the aqueous solution is pumped through the $1^{st}$ tube by a $1^{st}$ HPLC pump with a back pressure of at least 10 psi, 25 psi, 50 psi, 75 psi, or 100 psi and the ethanol solution is pumped through the $2^{nd}$ tube by a $2^{nd}$ HPLC pump with a back pressure of at least 40 psi, 80 psi, 150 psi, 300 psi, or 400 psi.

5. The method of claim 1, wherein the $1^{st}$ tube has an ID of 0.132" and the $2^{nd}$ tube has an ID of 0.007", 0.01", or 0.02".

6. The method of claim 1, wherein the aqueous solution is pumped at a flow rate of at least 30 ml/min, 45 ml/min, 60 ml/min, 75 ml/min, 90 ml/min, 105 ml/min, 120 ml/min, 150 ml/min, 225 ml/min, 262.5 ml/min, 300 ml/min, or 450 ml/min; and the ethanol solution is pumped at a flow rate of at least 10 ml/min, 15 ml/min, 20 ml/min, 25 ml/min, 30 ml/min, 35 ml/min, 40 ml/min, 50 ml/min, 60 ml/min, or 75 ml/min, 87.5 ml/min, 100 ml/min, or 150 ml/min.

7. The method of claim 1, wherein the aqueous, ethanol, output solutions are maintained at 15-20° C.

8. The method of claim 1, wherein the mixing module is made of stainless steel and consists of the $2^{nd}$ tube mounted perpendicularly on the $1^{st}$ tube, wherein the $1^{st}$ tube has an opening through a wall, wherein the opening is the size of the outside diameter of the $2^{nd}$ tube, and wherein the $2^{nd}$ tube is fitted over the opening to permit continuous movement of the ethanol solution in the $2^{nd}$ tube into the aqueous solution in the $1^{st}$ tube.

9. The method of claim 1, further comprising pumping a dilution buffer through a $3^{rd}$ tube, and mixing the dilution buffer with the output solution by introducing the dilution buffer to the output solution in the region of a Y-connector connecting the $3^{rd}$ tube to the $1^{st}$ tube to produce a diluted output solution.

10. The method of claim 9, wherein the dilution buffer comprises
a) between about 10 mM and 20 mM Tris buffer, between about 45 mM and 55 mM NaCl, and between about 8% and 10% sucrose, at a pH between about 7.4 and 8.5; or
b) between 40 mM and 90 mM phosphate buffer, at a pH between about 6.0 and 6.5; and (i) the $3^{rd}$ dilution buffer comprises between about 20 mM and 50 mM HEPES buffer; or
(ii) the $3^{rd}$ dilution buffer comprises between 20 mM and 50 mM HEPES buffer, between about 50 mM and 300 mM NaCl, between about 0% and 15% sucrose, at a pH between about 7.4 and 8.5.

11. The method of claim 9, wherein the diluted output solution comprises 6.25% ethanol; 8.25% ethanol; 8.3% ethanol; or 12.5% ethanol.

12. The method of claim 9, wherein the dilution buffer is pumped through the $3^{rd}$ tube at a flow rate of 400-900 mL/min.

13. The method of claim 9, wherein the $3^{rd}$ tube has an ID of 0.25".

14. The method of claim 1, wherein the lipid-encapsulated RNA nanoparticle has an average particle size of less than about 100 nm.

15. The method of claim 1, wherein the lipid portion of the lipid-encapsulated RNA nanoparticle comprises about 48 mol % to about 66 mol % of a cationic lipid, about 2 mol % to about 12 mol % DSPC, about 25 mol % to about 42 mol % cholesterol, and about 0.5 mol % to about 3 mol % PEG2000-DMG.

16. The method of claim 1, wherein the lipid-encapsulated RNA nanoparticle has a total lipid:RNA weight ratio of about 50:1 to about 3:1.

17. The method of claim 1, wherein the lipid-encapsulated RNA nanoparticle comprises a molar ratio of cationic lipid: DOTAP (1,2-dioleoyl-3-trimethylammonium-propane): DSPC:cholesterol:PEG selected from 25:25:10:38.5:1.5, 25:25:10:37:3, 25:25:10:35:5, 20:20:7:51.5:1.5, 25:20:10: 42:3, 20:30:13:32:5, 25:20:10:40:5, 25:25:13:35.5:1.5, 25:30:7:35:3, 30:20:13:34:3, 30:25:7:33:3, 30:30:10:25.8: 1.5, 15:20:13:49:3, 20:20:13:44:3, 20:25:13:39:3, 15:25:13: 44:3, 20:25:13:39:3, 25:25:13:34:3, 30:20:13:34:3, or 30:30: 13:29:3.

18. The method of claim 1, wherein the lipid-encapsulated RNA nanoparticle comprises between about 20 w/w % and 60 w/w % of the cationic lipid, between about 5 w/w % and 30 w/w % of a helper lipid, between about 0 w/w % and 60 w/w % of a cholesterol, and between about 0.5 w/w % and 15 w/w % of a polyethylene glycol-lipid conjugate (PEG).

19. The method of claim 1, wherein the RNA is selected from the group consisting of a transfer RNA, small nuclear RNA, ribosomal RNA, messenger RNA, antisense RNA, small interfering RNA and self-replicating RNA.

* * * * *

UNITED STATES PATENT AND TRADEMARK OFFICE
CERTIFICATE OF CORRECTION

| | | |
|---|---|---|
| PATENT NO. | : 11,737,979 B2 | |
| APPLICATION NO. | : 16/823212 | |
| DATED | : August 29, 2023 | |
| INVENTOR(S) | : Priya Karmali et al. | |

It is certified that error appears in the above-identified patent and that said Letters Patent is hereby corrected as shown below:

On the Title Page

Under item (72) of "Inventors" the inventors should appear as follows:
--Priya Karmali, San Diego, CA (US);
Padmanabh Chivukula, San Diego, CA (US);
Joseph E. Payne, San Diego, CA (US);
Yanjie Bao, San Diego, CA (US);
Michael Figa, San Mateo, CA (US);
Scott A. Roberts, San Diego, CA (US);
Andreas Wagner, Klosterneuburg (AT)--

Signed and Sealed this
Twelfth Day of March, 2024

Katherine Kelly Vidal
*Director of the United States Patent and Trademark Office*